United States Patent
Liu et al.

(10) Patent No.: US 12,071,430 B2
(45) Date of Patent: *Aug. 27, 2024

(54) ITRACONAZOLE ANALOGS AND USE THEREOF

(71) Applicant: The Johns Hopkins University, Baltimore, MD (US)

(72) Inventors: Jun Liu, Baltimore, MD (US); Yingjun Li, Baltimore, MD (US); Kalyan Kumar Pasunooti, Baltimore, MD (US); Wukun Liu, Baltimore, MD (US); Wei Shi, Baltimore, MD (US); Ruojing Li, Baltimore, MD (US); Sarah Head, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 460 days.

This patent is subject to a terminal disclaimer.

(21) Appl. No.: 17/282,378

(22) PCT Filed: Oct. 3, 2019

(86) PCT No.: PCT/US2019/054583
§ 371 (c)(1),
(2) Date: Apr. 1, 2021

(87) PCT Pub. No.: WO2020/072830
PCT Pub. Date: Apr. 9, 2020

(65) Prior Publication Data
US 2022/0106302 A1  Apr. 7, 2022

Related U.S. Application Data

(63) Continuation-in-part of application No. 16/152,008, filed on Oct. 4, 2018, now Pat. No. 11,028,078, which
(Continued)

(51) Int. Cl.
C07D 405/14 (2006.01)
A61K 31/496 (2006.01)
(Continued)

(52) U.S. Cl.
CPC ............ C07D 405/14 (2013.01); A61P 35/00 (2018.01); A61K 31/496 (2013.01); A61K 31/506 (2013.01)

(58) Field of Classification Search
CPC ..... A61K 31/496; A61K 31/506; A61P 35/00; C07D 405/06; C07D 405/14
See application file for complete search history.

(56) References Cited

U.S. PATENT DOCUMENTS 6,346,518 B1  2/2002  Heeres et al.
9,839,636 B2  12/2017  Hadden et al.
(Continued)

FOREIGN PATENT DOCUMENTS

WO  WO 94/16700 A1  8/1994

OTHER PUBLICATIONS

Wermuth, Molecular variations based in isosteric replacements, The Practice of Medicinal Chemistry, 1996, 203-237 (Year: 1996) (Year: 1996).*

(Continued)

*Primary Examiner* — Kortney L. Klinkel
*Assistant Examiner* — Padmaja S Rao
(74) *Attorney, Agent, or Firm* — DLA Piper LLP (US)

(57) ABSTRACT

Itraconazole, a widely used antifungal drug, has been found to possess potent anti-angiogenic and anti-hedgehog activities, exhibiting promising antitumor activity in several human clinical studies. The wider use of itraconazole in the treatment of cancer, however, has been limited by its potent inhibition of the drug metabolic enzyme CYP3A4 which causes drug-drug interactions. In an effort to eliminate the
(Continued)

CYP3A4 inhibition of itraconazole while retaining its anti-angiogenic activity, we synthesized a series of itraconazole derivatives. The newly synthesized analogs of itraconazole were evaluated for their cytotoxicity against human umbilical vein endothelial cells (HUVEC) and their inhibitory activity against CYP3A4 enzyme.

13 Claims, 7 Drawing Sheets

Related U.S. Application Data is a continuation-in-part of application No. 15/162,524, filed on May 23, 2016, now abandoned, which is a continuation of application No. 14/343,040, filed as application No. PCT/US2012/054306 on Sep. 7, 2012, now Pat. No. 9,346,791.

(60) Provisional application No. 62/742,046, filed on Oct. 5, 2018, provisional application No. 61/531,819, filed on Sep. 7, 2011.

(51) Int. Cl.
*A61K 31/506* (2006.01)
*A61P 35/00* (2006.01)

(56) References Cited

U.S. PATENT DOCUMENTS

| 2016/0264556 A1 | 9/2016 | Liu et al. |
| 2017/0209436 A1 | 7/2017 | Hadden et al. |
| 2019/0040046 A1 | 2/2019 | Liu et al. |

OTHER PUBLICATIONS

Shi et al., Itraconazole Side Chain Analogues: Structure-Activity Relationship Studies for Inhibition of Endothelial Cell Proliferation, Vascular Endothelial Growth Factor Receptor 2 (VEGFR2) Glycosylation, and Hedgehog Signaling, Journal of Medicinal Chemistry, vol. 54, 7363-7374, Oct. 27, 2011 (Year: 2011).*

Liu et al., Design and synthesis of pyridine-substituted itraconazole analogues with improved antifungal activities, water solubility and bioavailability, Bioorganic and Medicinal Chemistry Letters, Jul. 2, 2011 (Year: 2011).*

* cited by examiner

ITRACONAZOLE ANALOGS AND USE THEREOF

CROSS-REFERENCE TO RELATED APPLICATIONS

This application is a 35 USC § 371 National Stage application of International Application No. PCT/US2019/054583 filed Oct. 3, 2019, now pending; which claims the benefit under 35 USC § 119(e) to U.S. Application Ser. No. 62/742,046 filed Oct. 5, 2018. PCT/US2019/054583 filed Oct. 3, 2019, now pending, is also a continuation-in-part application of U.S. application Ser. No. 16/152,008 filed Oct. 4, 2018, now pending; which is a continuation-in-part application of U.S. application Ser. No. 15/162,524 filed May 23, 2016, now abandoned; which is a continuation application of U.S. application Ser. No. 14/343,040 filed Apr. 10, 2014, now issued as U.S. Pat. No. 9,346,791; which is a 35 USC § 371 National Stage application of International Application No. PCT/US2012/054306 filed Sep. 7, 2012, now expired; which claims the benefit under 35 USC § 119(e) to U.S. Application Ser. No. 61/531,819 filed Sep. 7, 2011. The disclosure of each of the prior applications is considered part of and is incorporated by reference in the disclosure of this application.

STATEMENT REGARDING FEDERALLY SPONSORED RESEARCH OR DEVELOPMENT

This invention was made with government support under Grant Nos. CA122814 and CA184103 awarded by the National Institutes of Health. The government has certain rights in the invention.

FIELD

The present disclosure relates generally to derivatives of itraconazole and more specifically to itraconazole analogs and compositions as pharmaceuticals for the treatment of disease.

BACKGROUND

Itraconazole is known for its use as a clinical agent for the treatment of a broad spectrum of fungal infections. However, it has been shown that itraconazole also possesses potent in vitro and in vivo anti-angiogenic activity, and additionally inhibits both Hedgehog (Hh) signaling and the growth of murine medulloblastoma (MB) allografts with deregulated Hh activity. These observations have led to expansion of the potential therapeutic application of itraconazole and have even sparked evaluation of this compound in four ongoing cancer clinical trials.

Itraconazole has been found to possess potent anti-angiogenic and anti-hedgehog activities, exhibiting promising antitumor activity in several human clinical studies. The wider use of itraconazole in the treatment of cancer, however, has been limited by its potent inhibition of the drug metabolic enzyme, human liver cytochrome P450 3A4 (CYP3A4), which causes drug-drug interactions. A major limitation of itraconazole as a novel anticancer drug is it is a strong inhibitor of CYP3A4. CYP3A4 is the major xenobiotics metabolic enzyme and it contributes the metabolism of approximately 50% of prescribed drugs and the majority of anticancer drugs. Inhibition of CYP3A4 could lead to reduced metabolism of other drugs that might lead to unwanted side effects, thus prevents the combination of itraconazole with those drugs in cancer therapy. Many anticancer drugs, especially those that inhibit angiogenesis, are most effective when used in combination with other drugs. Thus, there is a need to develop novel itraconazole analogs with reduced or no CYP3A4 inhibition while retaining its anti-angiogenic activity.

SUMMARY

The present disclosure is based on the seminal discovery of a series of itraconazole analog compounds as potent anti-angiogenic agents with reduced CYP3A4 inhibition.

Provided herein are compounds having structure Formula (I), or an optically pure stereoisomer or pharmaceutically acceptable salt, hydrate, solvate, or prodrug thereof, Formula (I)

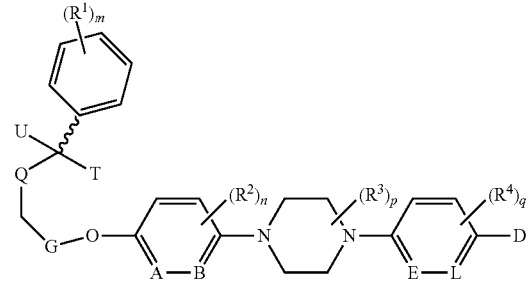

or an optically pure stereoisomer or pharmaceutically acceptable salt thereof, wherein U is selected from the group consisting of hydrogen, alkyl, arylalkyl, alkoxyalkyl, arylalkoxy, alkynylalkyl, alkylalkynylalkyl, alkenylalkyl, alkylalkenylalkyl, cycloalkyl, cyanoalkyl, cycloalkylalkyl, heteroalkyl, heterocycloalkyl, heteroaryl, heteroarylalkyl, heterocycloalkylalkyl, haloalkyl, halogen, amino, amido, nitro, and cyano, any of which may be optionally substituted;

$R^1$, $R^2$, $R^3$, and $R^4$ are each independently selected from the group consisting of alkoxy, alkyl, alkynyl, amino, amido, halogen, hydroxyl, haloalkyl, perhaloalkyl, perhaloalkoxy, nitro, and cyano, any of which may be optionally substituted;

A is $CR^5$ or N;
B is $CR^6$ or N;
E is $CR^7$ or N;
L is $CR^8$ or N;
Q is O or $CH_2$;
$R^5$, $R^6$, $R^7$, and $R^8$ are each independently selected from the group consisting of hydrogen, alkoxy, alkyl, alkynyl, amino, halogen, hydroxyl, haloalkyl, perhaloalkyl, perhaloalkoxy, nitro, and cyano, any of which may be optionally substituted;

T is $OR^9$ or hydrogen;
R9 is hydrogen or alkyl optionally substituted;
G is $(CH2)z$ or G and R9 together with the atom(s) to which they are attached may optionally be joined together to form a monocyclic heterocyclic including, but not limited to, dioxolane;
z is an integer between 0 and 2;
m is an integer between 0 and 5;
n and q are each independently an integer between 0 and 2;
p is an integer between 0 and 4;

D is selected from the group consisting of:

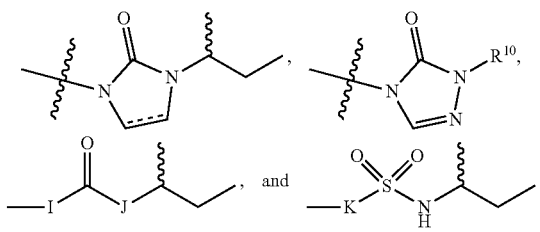

wherein, ----- is a single or double bond;

R10 is selected from the group consisting of hydrogen, alkyl, arylalkyl, alkoxyalkyl, arylalkoxy, alkynylalkyl, alkylalkynylalkyl, alkenylalkyl, alkylalkenylalkyl, cycloalkyl, cyanoalkyl, cycloalkylalkyl, heteroalkyl, heterocycloalkyl, heteroaryl, heteroarylalkyl, heterocycloalkylalkyl, and alkylsulfonyl, any of which can be optionally substituted;

I is (CH2)r or NH;
J is (CH2)s or NH;
K is (CH2)t or NH;
r, s, and t are each independently an integer between 0 and 4.

In a specific embodiment, U is not

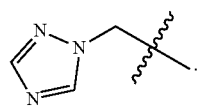 [SMILES: *Cn1cncn1]

Also provided herein are compounds having structure Formula (II), or an optically pure stereoisomer or pharmaceutically acceptable salt, hydrate, solvate, or prodrug thereof, $R^1$ and $R^2$ are each independently selected from the group consisting of alkoxy, alkyl, alkynyl, amino, amido, halogen, hydroxyl, haloalkyl, perhaloalkyl, perhaloalkoxy, nitro, and cyano, any of which may be optionally substituted;

n is an integer between 0 and 5;

R3 is selected from the group consisting of hydrogen, alkyl, arylalkyl, alkoxyalkyl, arylalkoxy, alkynylalkyl, alkylalkynylalkyl, alkenylalkyl, alkylalkenylalkyl, cycloalkyl, cyanoalkyl, cycloalkylalkyl, heteroalkyl, heterocycloalkyl, heteroaryl, heteroarylalkyl, heterocycloalkylalkyl, and alkylsulfonyl, any of which can be optionally substituted.

Also provided herein are compounds having structure Formula (III), or an optically pure stereoisomer or pharmaceutically acceptable salt, hydrate, solvate, or prodrug thereof, Formula (III)

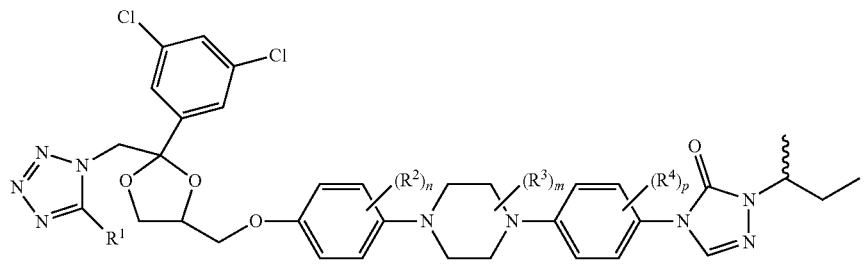

R1 selected from the group consisting of alkoxy, alkyl, alkynyl, amino, amido, halogen, hydroxyl, haloalkyl, perhaloalkyl, perhaloalkoxy, nitro, and cyano, any of which may be optionally substituted;

R2, R3, and R4 are each independently selected from the group consisting of alkoxy, alkyl, alkynyl, amino, amido, halogen, hydroxyl, haloalkyl, perhaloalkyl, perhaloalkoxy, nitro, and cyano, any of which may be optionally substituted;

n and p are each independently an integer between 0 and 2;

m is an integer between 0 and 4.

Further provided herein are compounds having structure Formula (IV), or an optically pure stereoisomer or pharmaceutically acceptable salt, hydrate, solvate, or prodrug thereof, Formula (II)

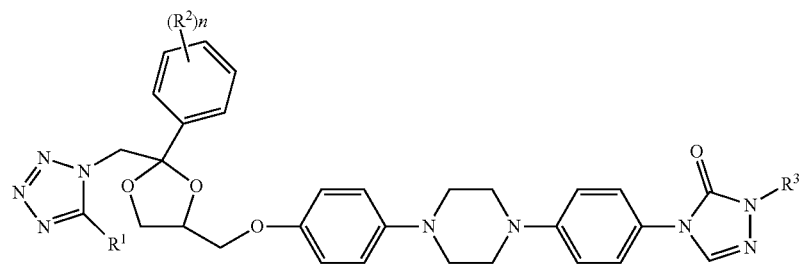

Formula (IV)

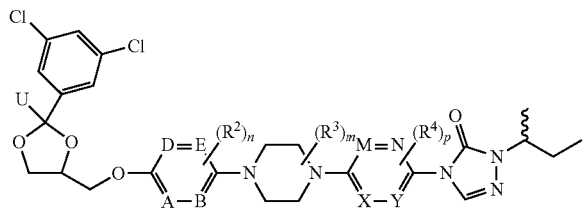

or an optically pure stereoisomer or pharmaceutically acceptable salt thereof.

Wherein U is selected from the group consisting of

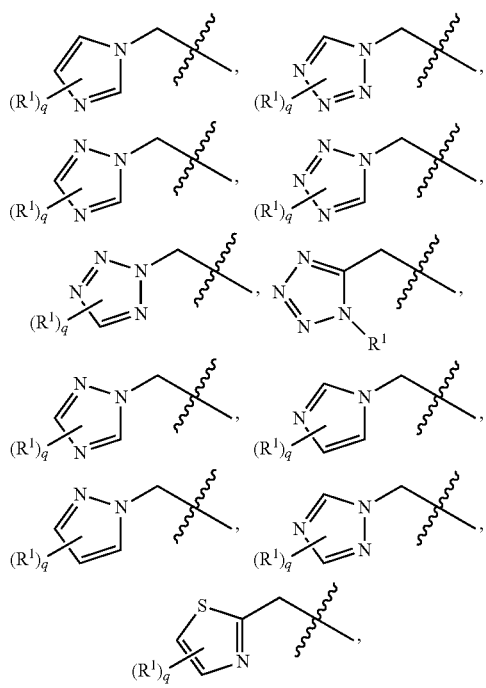

and optionally substituted phenyl;

R1, R2, R3, and R4 are each independently selected from the group consisting of hydrogen, trifluoromethyl, alkoxy, alkyl, alkynyl, amino, amido, halogen, hydroxyl, haloalkyl, perhaloalkyl, perhaloalkoxy, nitro, and cyano, any of which may be optionally substituted;

Each A, B, D, E, M, N, X, and Y is independently CH or N;

m is an integer between 0 and 5;

n and p is each independently an integer between 0 and 2;

q is 0, 1, 2, or 3.

Also disclosed herein is a method of treating a disease in the subject, the method comprising administering an effective amount of the compound according to Formula (I), Formula (II), Formula (III), or Formula (IV). In some embodiments, the disease is cancer. In some embodiments, the cancer is selected from the group consisting of central nervous system (CNS) cancer, lung cancer, breast cancer, colorectal cancer, prostate cancer, stomach cancer, liver cancer, cervical cancer, esophageal cancer, bladder cancer, Non-Hodgkin lymphoma, leukemia, pancreatic cancer, kidney cancer, endometrial cancer, head and neck cancer, lip cancer, oral cancer, thyroid cancer, brain cancer, ovary cancer, renal cancer, melanoma, gallbladder cancer, laryngeal cancer, multiple myeloma, nasopharyngeal cancer, Hodgkin lymphoma, testis cancer and Kaposi sarcoma.

In some embodiments, the disease can be dependent on angiogenesis. In some embodiments, the angiogenesis-dependent disease can be selected from the group consisting of macular degeneration, diabetic retinopathy, hemangiomas, colon polyps, precancerous skin lesions, uveitis, ocular melanoma, corneal neovascularization, primary pterygium, HSV stromal keratitis, HSV-1-induced corneal lymphangiogenesis, retinopathy of prematurity, retinal vein occlusion, corneal graft rejection, neovascular glaucoma, and rubeosis. In some embodiments, the method further includes administering a chemotherapeutic agent. The compound can be administered prior to, simultaneously with or following the administration of the chemotherapeutic agent.

Further disclosed herein is a pharmaceutical formulation, including the compound with a Formula (I), Formula (II), Formula (III), or Formula (IV), and a pharmaceutically acceptable carrier. In some embodiments, the compound can be formulated in a delayed release preparation, a slow release preparation, an extended release preparation, or a controlled release preparation. In some embodiments, the compound can be provided in a dosage form selected from an injectable dosage form, infusible dosage form, inhalable dosage form, edible dosage form, oral dosage form, topical dosage form, and combinations thereof. In some embodiments, the dosage form includes an enteric coating.

DETAILED DESCRIPTION

Figure 1:
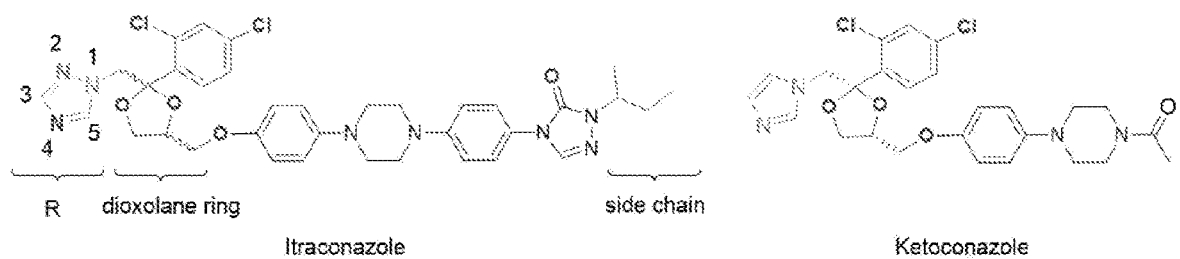
FIG. 1 shows the structures of itraconazole and ketoconazole.

Angiogenesis, the formation of new blood vessels plays a critical role in the onset and progression of cancer as well as a number of other human diseases. Inhibition of angiogenesis has become an important strategy to combat cancer as underscored by the clinical introduction of a number of inhibitors of angiogenesis. In an effort to repurpose existing drugs as new angiogenesis inhibitors, we previously found that the antifungal drug itraconazole possessed potent anti-angiogenic activity. The molecular target of itraconazole underlying its antifungal activity is lanosterol 14α-demethylase (14-DM). But itraconazole only shows weak inhibition of human 14-DM, ruling it out as a relevant target for the anti-angiogenic activity of itraconazole. Instead, we have identified Voltage-Dependent Anion Channel (VDAC)1 and Niemann Pick type C (NPC)1 as the direct targets of itraconazole. We have shown that binding of itraconazole to NPC1 leads to inhibition of cholesterol trafficking out of the endolysosome, which in turn induces NPC1 phenotype. Binding of itraconazole to VDAC1 blocks ATP biosynthesis in the mitochondria, increasing cytosolic AMP/ATP ratio and activating AMPK. Inhibition of cholesterol trafficking and activation of AMPK lead to synergistic inhibition of mTOR signaling. The unique mechanism of action of itraconazole distinguishes it from rapamycin, a direct inhibitor of mTOR and most other triazole antifungal drugs such as ketoconazole, which do not have angiogenesis activities. The new mechanistic insight, along with other preclinical results, have facilitated the entrance of itraconazole into multiple phase II clinical trial studies in the treatment of prostate cancer, non-small cell lung cancer, basal cell carcinoma and other cancers.

A major limitation of itraconazole as a novel anticancer drug is its strong inhibitor of human liver cytochrome P450 3A4 (CYP3A4). CYP3A4 is the major xenobiotics metabolic enzyme and it contributes the metabolism of approximately 50% of prescribed drugs and the majority of anticancer drugs. Inhibition of CYP3A4 could lead to reduced metabolism of other drugs that might lead to unwanted side effects, thus prevents the combination of itraconazole with those drugs in cancer therapy. Many anticancer drugs, especially those that inhibit angiogenesis, are most effective when used in combination with other drugs. Thus, there is a need to develop novel itraconazole analogs with reduced or with no CYP3A4 inhibition while retaining its anti-angiogenic activity.

Previously work, we identified an itraconazole stereoisomer with cis-stereo (cis-2R,4S) chemistry of dioxalane moiety with an increased anti-angiogenesis activity and significantly reduced hepatotoxicity. See U.S. Pat. No. 9,346,791. We also found that a sec-butyl side chain or those with similar length is required for antiangiogenic activity. The triazole moiety of itraconazole is a critical pharmacophore required for the binding of itraconazole to the heme group of the antifungal target 14-DM as well as the heme group of CYP3A4. However, little is known about the importance of the triazole moiety in anti-angiogenic activity of itraconazole.

In an effort to identify novel analogs of itraconazole with reduced or no CYP3A4 inhibition while retaining its anti-angiogenic potency, we systematically modified the structure of the 1,2,4-triazole (R1) moiety. Herein, we report the SAR (structure and activity relationship) study of new triazole analogs of itraconazole for their anti-angiogenic activity and CYP3A4 inhibition and successful identification of a class of itraconazole analogs with potent anti-angiogenic activity but significantly reduced CYP3A4 inhibitory activity compared to itraconazole.

Provided herein are compounds having structure Formula (I), or an optically pure stereoisomer or pharmaceutically acceptable salt, hydrate, solvate, or prodrug thereof,

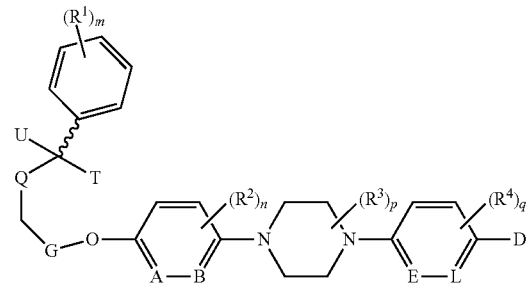

Formula (I)

or an optically pure stereoisomer or pharmaceutically acceptable salt thereof, wherein U is selected from the group consisting of hydrogen, alkyl, arylalkyl, alkoxyalkyl, arylalkoxy, alkynylalkyl, alkylalkynylalkyl, alkenylalkyl, alkylalkenylalkyl, cycloalkyl, cyanoalkyl, cycloalkylalkyl, heteroalkyl, heterocycloalkyl, heteroaryl, heteroarylalkyl, heterocycloalkylalkyl, haloalkyl, halogen, amino, amido, nitro, and cyano, any of which may be optionally substituted;

R1, R2, R3, and R4 are each independently selected from the group consisting of alkoxy, alkyl, alkynyl, amino, amido, halogen, hydroxyl, haloalkyl, perhaloalkyl, perhaloalkoxy, nitro, and cyano, any of which may be optionally substituted;

A is CR5 or N;
B is CR6 or N;
E is CR7 or N;
L is CR8 or N;
Q is O or CH2;

R5, R6, R7, and $R^8$ are each independently selected from the group consisting of hydrogen, alkoxy, alkyl, alkynyl, amino, halogen, hydroxyl, haloalkyl, perhaloalkyl, perhaloalkoxy, nitro, and cyano, any of which may be optionally substituted;

T is OR9 or hydrogen;

R9 is hydrogen or alkyl optionally substituted;

G is (CH2)z or G and R9 together with the atom(s) to which they are attached may optionally be joined together to form a monocyclic heterocyclic including, but not limited to, dioxolane;

z is an integer between 0 and 2;

m is an integer between 0 and 5;

n and q are each independently an integer between 0 and 2;

p is an integer between 0 and 4;

heterocycloalkyl, heteroaryl, heteroarylalkyl, heterocycloalkylalkyl, and alkylsulfonyl, any of which can be optionally substituted;

I is (CH2)r or NH;

J is (CH2)s or NH;

K is (CH2)t or NH;

r, s, and t are each independently an integer between 0 and 4.

In a specific embodiment, U is not

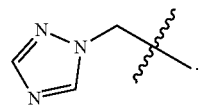

Also provided herein are compounds having structure Formula (II), or an optically pure stereoisomer or pharmaceutically acceptable salt, hydrate, solvate, or prodrug thereof, Formula (II)

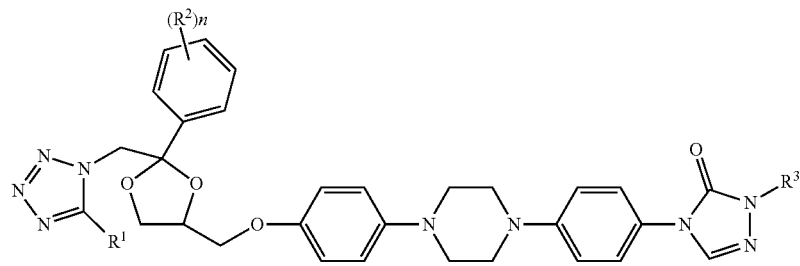

D is selected from the group consisting of:

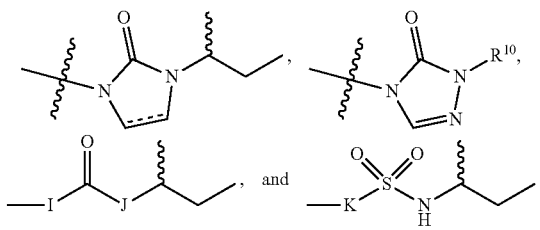

wherein, ----- is a single or double bond;

R10 is selected from the group consisting of hydrogen, alkyl, arylalkyl, alkoxyalkyl, arylalkoxy, alkynylalkyl, alkylalkynylalkyl, alkenylalkyl, alkylalkenylalkyl, cycloalkyl, cyanoalkyl, cycloalkylalkyl, heteroalkyl, R1 and R2 are each independently selected from the group consisting of alkoxy, alkyl, alkynyl, amino, amido, halogen, hydroxyl, haloalkyl, perhaloalkyl, perhaloalkoxy, nitro, and cyano, any of which may be optionally substituted;

n is an integer between 0 and 5;

R3 is selected from the group consisting of hydrogen, alkyl, arylalkyl, alkoxyalkyl, arylalkoxy, alkynylalkyl, alkylalkynylalkyl, alkenylalkyl, alkylalkenylalkyl, cycloalkyl, cyanoalkyl, cycloalkylalkyl, heteroalkyl, heterocycloalkyl, heteroaryl, heteroarylalkyl, heterocycloalkylalkyl, and alkylsulfonyl, any of which can be optionally substituted.

Also provided herein are compounds having structure Formula (III), or an optically pure stereoisomer or pharmaceutically acceptable salt, hydrate, solvate, or prodrug thereof, Formula (III)

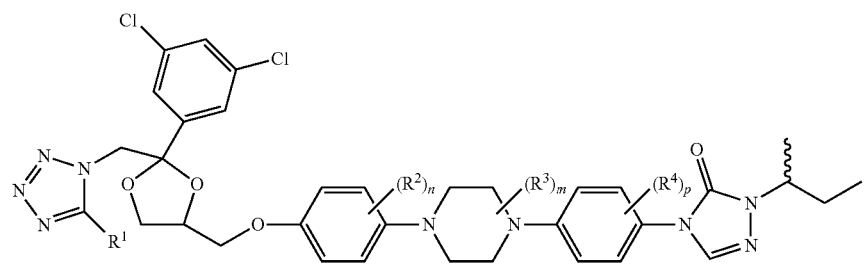

R1 selected from the group consisting of alkoxy, alkyl, alkynyl, amino, amido, halogen, hydroxyl, haloalkyl, perhaloalkyl, perhaloalkoxy, nitro, and cyano, any of which may be optionally substituted;

R2, R3, and R4 are each independently selected from the group consisting of alkoxy, alkyl, alkynyl, amino, amido, halogen, hydroxyl, haloalkyl, perhaloalkyl, perhaloalkoxy, nitro, and cyano, any of which may be optionally substituted.

n and p are each independently an integer between 0 and 2;

m is an integer between 0 and 4.

Further provided herein are compounds having structure Formula (IV), or an optically pure stereoisomer or pharmaceutically acceptable salt, hydrate, solvate, or prodrug thereof,

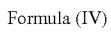

Formula (IV)

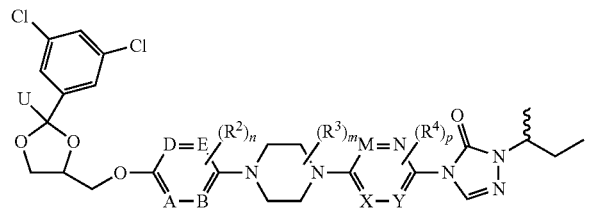

or an optically pure stereoisomer or pharmaceutically acceptable salt thereof.

Wherein U is selected from the group consisting of

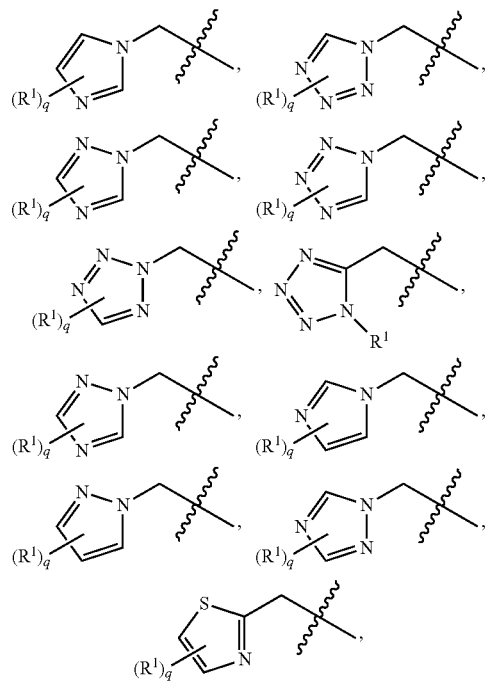

and optionally substituted phenyl;

$R^1$, $R^2$, $R^3$, and $R^4$ are each independently selected from the group consisting of hydrogen, trifluoromethyl, alkoxy, alkyl, alkynyl, amino, amido, halogen, hydroxyl, haloalkyl, perhaloalkyl, perhaloalkoxy, nitro, and cyano, any of which may be optionally substituted;

Each A, B, D, E, M, N, X, and Y is independently CH or N;

m is an integer between 0 and 5;

n and p is each independently an integer between 0 and 2;

q is 0, 1, 2, or 3.

As used herein, the terms below have the meanings indicated.

When ranges of values are disclosed, and the notation "from n1 . . . to n2" or "between n1 . . . and n2" is used, where n1 and n2 are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.). When n is set at 0 in the context of "0 carbon atoms", it is intended to indicate a bond or null.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety where the atom attached to the carbonyl is carbon. An "acetyl" group refers to a —C(O)CH3 group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon group having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—), (—C:C—)]. Examples of suitable alkenyl groups include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether group, wherein the term alkyl is as defined below. Examples of suitable alkyl ether groups include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl group containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl groups include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—$CH_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) group wherein the term alkyl is as defined above and wherein the sulfur may be singly or doubly oxidized. Examples of suitable alkyl thioether groups include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched-chain hydrocarbon group having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:C—, —CC—). Examples of alkynyl groups include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C amido" as used herein, alone or in combination, refers to a C(=O)NR2 group with R as defined herein. The term "N amido" as used herein, alone or in combination, refers to a RC(=O)NH group, with R as defined herein. The term "acylamino" as used herein, alone or in combination, embraces an acyl group attached to the parent moiety through an amino group. An example of an "acylamino" group is acetylamino (CH3C(O)NH—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl group derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent group C6H4= derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O carbamyl" as used herein, alone or in combination, refers to a OC(O)NRR' group with R and R' as defined herein.

The term "N carbamyl" as used herein, alone or in combination, refers to a ROC(O)NR' group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O carboxy" group refers to a RC(O)O— group, where R is as defined herein. A "C carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl group having the meaning as defined above wherein one or more hydrogens are replaced with a halogen. Specifically embraced are monohaloalkyl, dihaloalkyl and polyhaloalkyl groups. A monohaloalkyl group, for one example, may have an iodo, bromo, chloro or fluoro atom within the group. Dihalo and polyhaloalkyl groups may have two or more of the same halo atoms or a combination of different halo groups. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene.

(—CFH—), difluoromethylene (—CF2-), chloromethylene (—CHCl—) and the like.

The term "heteroalkyl," as used herein, alone or in combination, refers to a stable straight or branched chain, or cyclic hydrocarbon group, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH2-NH—OCH3.

The term "heteroaryl," as used herein, alone or in combination, refers to a 3 to 7 membered unsaturated heteromonocyclic ring, or a fused monocyclic, bicyclic, or tricyclic ring system in which at least one of the fused rings is aromatic, which contains at least one atom selected from the group consisting of O, S, and N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently selected from the group consisting of nitrogen, oxygen, and sulfur In certain embodiments, said hetercyclalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, which may be optionally substituted as provided.

The term "lower heteroaryl," as used herein, alone or in combination, means either: 1) monocyclic heteroaryl comprising five or six ring members, of which between one and four said members may be heteroatoms selected from the group consisting of O, S, and N; or 2) bicyclic heteroaryl, wherein each of the fused rings comprises five or six ring members, comprising between them one to four heteroatoms selected from the group consisting of 0, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms selected from the group consisting of O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently selected from the group consisting of hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —NO2.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer to the —SO3H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)2-.

The term "N sulfonamido" refers to a RS(=O)2NR' group with R and R' as defined herein.

The term "S sulfonamido" refers to a S(=O)2NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N thiocarbamyl" refers to an ROC(S)NR'— group, with R and R' as defined herein.

The term "O thiocarbamyl" refers to a —OC(S)NRR', group with R and R' as defined herein.

The term "thiocyanato" refers to a —CNS group.

The term "trihalomethanesulfonamido" refers to a X3CS(O)2NR— group with X is a halogen and R as defined herein.

The term "trihalomethanesulfonyl" refers to a X3CS(O)2- group where X is a halogen.

The term "trihalomethoxy" refers to a X3CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxy ester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N3, SH, SCH3, C(O)CH3, CO2CH3, CO2H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH2CH3), fully substituted (e.g., —CF2CF3), monosubstituted (e.g., —CH2CH2F) or substituted at a level anywhere in-between fully substituted and monosubstituted (e.g., —CH2CF3). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and Rn where n=(1, 2, 3, . . . n), every substituent, and every term should be understood to be independent of every other in terms of selection from a group. Should any variable, substituent, or term (e.g., aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the disclosure encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Additionally, compounds may exist as tautomers; all tautomeric isomers are provided by this disclosure. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "optically pure stereoisomer" refers to stereoisomeric, such as enantiomeric or diastereomeric excess or the absolute difference between the mole fraction of each enantiomer or diastereomer.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "inhibition" (and by extension, "inhibitor") as used herein encompasses all forms of functional protein (enzyme, kinase, receptor, channel, etc., for example) inhibition, including neutral antagonism, inverse agonism, competitive inhibition, and non-competitive inhibition (such as allosteric inhibition). Inhibition may be phrased in terms of an IC50, defined below.

"Inhibitor" is used herein to refer to a compound that exhibits an IC50 activity with respect to its target of no more than about 100 µM and more typically not more than about 50 µM, as measured in the assays described generally herein below. "IC50" is that concentration of inhibitor which reduces the activity of an enzyme to half-maximal level. Certain representative compounds of the present disclosure have been discovered to exhibit inhibition VEGFR2 or Hedgehog (Hh) pathway. In certain embodiments, compounds will exhibit an IC50 with respect to VEGFR2 or Hh pathway of no more than about 10 µM; in further embodiments, compounds will exhibit an IC50 with respect to VEGFR2 or Hh pathway of no more than about 5 µM; in yet further embodiments, compounds will exhibit an IC50 with respect VEGFR2 or Hh pathway of not more than about 1 µM, as measured in the VEGFR2 or Hh pathway assay described herein. In yet further embodiments, compounds will exhibit an IC50 with respect to VEGFR2 or Hh pathway of not more than about 200 nM.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain compounds disclosed herein may also exist as prodrugs, as described in Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like.

Abbreviations. HUVEC, human umbilical vein endothelial cell; NPC1, Niemann-Pick disease, type C1; VDAC1, voltage-dependent anion channel 1; 14-DM, lanosterol 14-alpha demethylase; mTORC, mammalian target of rapamycin complex; SAR, structure-activity relationship; IC50, half-maximal inhibitory concentration; DMSO, dimethyl sulfoxide; DMF dimethylformamide; EC50, half-maximal effective concentration; AMPK, 5' AMP-activated protein kinase; ATP, adenosine triphosphate; AMP, adenosine monophosphate; CYP3A4, cytochrome P450 3A4; THF, tetrahydrofuran; DCM, dichloromethane; TfOH, trifluoromethanesulfonic acid; NaH, sodium hydride; ACC1, acetyl CoA carboxylase 1; S6K, p70 S6 kinase.

Basic addition salts can be prepared during the final isolation and purification of the compounds by reacting a carboxyl group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

While it may be possible for the compounds of the subject disclosure to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, drageemaking, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject disclosure or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Topical ophthalmic, otic, and nasal formulations of the present disclosure may comprise excipients in addition to the active ingredient. Excipients commonly used in such formulations include, but are not limited to, tonicity agents, preservatives, chelating agents, buffering agents, and surfactants. Other excipients comprise solubilizing agents, stabilizing agents, comfort-enhancing agents, polymers, emollients, pH-adjusting agents and/or lubricants. Any of a variety of excipients may be used in formulations of the present disclosure including water, mixtures of water and water-miscible solvents, such as C1-C7-alkanols, vegetable oils or mineral oils comprising from 0.5 to 5% non-toxic water-soluble polymers, natural products, such as alginates, pectins, tragacanth, karaya gum, guar gum, xanthan gum, carrageenin, agar and acacia, starch derivatives, such as starch acetate and hydroxypropyl starch, and also other synthetic products such as polyvinyl alcohol, polyvinylpyrrolidone, polyvinyl methyl ether, polyethylene oxide, preferably cross-linked polyacrylic acid and mixtures of those products. The concentration of the excipient is, typically, from 1 to 100,000 times the concentration of the active ingredient. In preferred embodiments, the excipients to be included in the formulations are typically selected on the basis of their inertness towards the active ingredient component of the formulations.

Relative to ophthalmic, otic, and nasal formulations, suitable tonicity-adjusting agents include, but are not limited to, mannitol, sodium chloride, glycerin, sorbitol and the like. Suitable buffering agents include, but are not limited to, phosphates, borates, acetates and the like. Suitable surfactants include, but are not limited to, ionic and nonionic surfactants (though nonionic surfactants are preferred), RLM 100, POE 20 cetylstearyl ethers such as Procol® CS20 and poloxamers such as Pluronic® F68.

The formulations set forth herein may comprise one or more preservatives. Examples of such preservatives include p-hydroxybenzoic acid ester, sodium perborate, sodium chlorite, alcohols such as chlorobutanol, benzyl alcohol or phenyl ethanol, guanidine derivatives such as polyhexamethylene biguanide, sodium perborate, polyquaternium-1, amino alcohols such as AMP-95, or sorbic acid. In certain embodiments, the formulation may be self-preserved so that no preservation agent is required.

For ophthalmic, otic, or nasal administration, the formulation may be a solution, a suspension, or a gel. In preferred aspects, the formulations are for topical application to the eye, nose, or ear in aqueous solution in the form of drops. The term "aqueous" typically denotes an aqueous formulation wherein the formulation is >50%, more preferably >75% and in particular >90% by weight water. These drops may be delivered from a single dose ampoule which may preferably be sterile and thus render bacteriostatic components of the formulation unnecessary. Alternatively, the drops may be delivered from a multi-dose bottle which may preferably comprise a device which extracts any preservative from the formulation as it is delivered, such devices being known in the art.

For ophthalmic disorders, components of the disclosure may be delivered to the eye as a concentrated gel or a similar vehicle, or as dissolvable inserts that are placed beneath the eyelids.

The formulations of the present disclosure that are adapted for topical administration to the eye are preferably isotonic, or slightly hypotonic in order to combat any hypertonicity of tears caused by evaporation and/or disease. This may require a tonicity agent to bring the osmolality of the formulation to a level at or near 210-320 milliosmoles per kilogram (mOsm/kg). The formulations of the present disclosure generally have an osmolality in the range of 220-320 mOsm/kg, and preferably have an osmolality in the range of 235-300 mOsm/kg. The ophthalmic formulations will generally be formulated as sterile aqueous solutions.

In certain ophthalmic embodiments, the compositions of the present disclosure are formulated with one or more tear substitutes. A variety of tear substitutes are known in the art and include, but are not limited to: monomeric polyols, such as, glycerol, propylene glycol, and ethylene glycol; polymeric polyols such as polyethylene glycol; cellulose esters such hydroxypropylmethyl cellulose, carboxy methylcellulose sodium and hydroxy propylcellulose; dextrans such as dextran 70; vinyl polymers, such as polyvinyl alcohol; and carbomers, such as carbomer 934P, carbomer 941, carbomer 940 and carbomer 974P. Certain formulations of the present disclosure may be used with contact lenses or other ophthalmic products.

Preferred formulations are prepared using a buffering system that maintains the formulation at a pH of about 4.5 to a pH of about 8. A most preferred formulation pH is from 6 to 8.

In particular embodiments, a formulation of the present disclosure is administered once a day. However, the formulations may also be formulated for administration at any frequency of administration, including once a week, once every 5 days, once every 3 days, once every 2 days, twice a day, three times a day, four times a day, five times a day, six times a day, eight times a day, every hour, or any greater frequency. Such dosing frequency is also maintained for a varying duration of time depending on the therapeutic regimen. The duration of a particular therapeutic regimen may vary from one-time dosing to a regimen that extends for months or years. The formulations are administered at varying dosages, but typical dosages are one to two drops at each administration, or a comparable amount of a gel or other formulation. One of ordinary skill in the art would be familiar with determining a therapeutic regimen for a specific indication.

Gels for topical or transdermal administration may comprise, generally, a mixture of volatile solvents, nonvolatile solvents, and water. In certain embodiments, the volatile solvent component of the buffered solvent system may include lower (C1-C6) alkyl alcohols, lower alkyl glycols and lower glycol polymers. In further embodiments, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. In certain embodiments, propylene glycol is used. The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound may crystallize due to evaporation of volatile solvent, while an excess may result in a lack of bioavailability due to poor release of drug from solvent mixture. The buffer component of the buffered solvent system may be selected from any buffer commonly used in the art; in certain embodiments, water is used. A common ratio of ingredients is about 20% of the nonvolatile solvent, about 40% of the volatile solvent, and about 40% water. There are several optional ingredients which can be added to the topical composition. These include, but are not limited to, chelators and gelling agents. Appropriate gelling agents can include, but are not limited to, semisynthetic cellulose derivatives (such as hydroxypropylmethylcellulose), synthetic polymers, galactomannan polymers (such as guar and derivatives thereof) and cosmetic agents.

Lotions include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or *arachis* oil.

Creams, ointments or pastes are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, *arachis*, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops may comprise sterile aqueous or oily solutions or suspensions and may be prepared by dissolving the active ingredient in a suitable aqueous solution of a bactericidal and/or fungicidal agent and/or any other suitable preservative, and, in certain embodiments, including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g., orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

The term "cancer" refers to a group diseases characterized by abnormal and uncontrolled cell proliferation starting at one site (primary site) with the potential to invade and to spread to others sites (secondary sites, metastases) which differentiate cancer (malignant tumor) from benign tumor. Virtually all the organs can be affected, leading to more than 100 types of cancer that can affect humans. Cancers can result from many causes including genetic predisposition, viral infection, exposure to ionizing radiation, exposure environmental pollutant, tobacco and or alcohol use, obesity, poor diet, lack of physical activity or any combination thereof.

Exemplary cancers described by the national cancer institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood: Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths;

Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma. Childhood Brain Stem; Glioma. Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's; Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplasia Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Hi stiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood'; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland' Cancer, Childhood; Sarcoma, Ewing's Family of Tumors; Sarcoma, Kaposi's; Sarcoma (OsteosarcomaVMalignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor.

In certain aspects, cancer include Lung cancer, Breast cancer, Colorectal cancer, Prostate cancer, Stomach cancer, Liver cancer, cervical cancer, Esophageal cancer, Bladder cancer, Non-Hodgkin lymphoma, Leukemia, Pancreatic cancer, Kidney cancer, endometrial cancer, Head and neck cancer, Lip cancer, oral cancer, Thyroid cancer, Brain cancer, Ovary cancer, Melanoma, Gallbladder cancer, Laryngeal cancer, Multiple myeloma, Nasopharyngeal cancer, Hodgkin lymphoma, Testis cancer and Kaposi sarcoma.

In an additional aspect, the method further includes administering a chemotherapeutic agent. The compounds of the disclosure can be administered in combination with one or more additional therapeutic agents. The phrases "combination therapy", "combined with" and the like refer to the use of more than one medication or treatment simultaneously to increase the response. The compounds of the present disclosure might for example be used in combination with other drugs or treatment in use to treat cancer. In various aspect, the compound is administered prior to, simultaneously with or following the administration of the chemotherapeutic agent.

The term "anti-cancer therapy" refers to any therapy or treatment that can be used for the treatment of a cancer. Anti-cancer therapies include, but are not limited to, surgery, radiotherapy, chemotherapy, immune therapy and targeted therapies.

Examples of chemotherapeutic agents or anti-cancer agents include, but are not limited to, Actinomycin, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fiuorouracil, Gemcitabine, Hydroxyurea, Idarubicin, Imatinib, lrinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, Vinorelbine, panitumamab, Erbitux (cetuximab), matuzumab, IMC-IIF 8, TheraCIM hR3, denosumab, Avastin (bevacizumab), Humira (adalimumab), Herceptin (trastuzumab), Remicade (infliximab), rituximab, Synagis (palivizumab), Mylotarg (gemtuzumab oxogamicin), Raptiva (efalizumab), Tysabri (natalizumab), Zenapax (dacliximab), NeutroSpec (Technetium (99mTc) fanolesomab), tocilizumab, ProstaScint (Indium-Ill labeled Capromab Pendetide), Bexxar (tositumomab), Zevalin (ibritumomab tiuxetan (IDEC-Y2B8) conjugated to yttrium 90), Xolair (omalizumab), MabThera (Rituximab), ReoPro (abciximab), MabCampath (alemtuzumab), Simulect (basiliximab), LeukoScan (sulesomab), CEA-Scan (arcitumomab), Verluma (nofetumomab), Panorex (Edrecolomab), alemtuzumab, CDP 870, natalizumab Gilotrif (afatinib), Lynparza (olaparib), Perj eta (pertuzumab), Otdivo (nivolumab), Bosulif (bosutinib), Cabometyx (cabozantinib), Ogivri (trastuzumab-dkst), Sutent (sunitinib malate), Adcetris (brentuximab vedotin), Alecensa (alectinib), Calquence (acalbrutinib), Yescarta (ciloleucel), Verzenio (abemaciclib), Keytruda (pembrolizumab), Aliqopa (copanlisib), Nerlynx (neratinib), Imfinzi (durvalumab), Darzalex (daratumumab), Tecentriq (atezolizumab), and Tarceva (erlotinib). Examples of immunotherapeutic agent include, but are not limited to, interleukins (11-2, 11-7, 11-12), cytokines (Interferons, G-CSF, imiquimod), chemokines (CCL3, CCl26, CXCL7), immunomodulatory imide drugs (thalidomide and its analogues).

In treatment, the dose of agent optionally ranges from about 0.0001 mg/kg to about 100 mg/kg, about 0.01 mg/kg to about 5 mg/kg, about 0.15 mg/kg to about 3 mg/kg, 0.5 mg/kg to about 2 mg/kg and about 1 mg/kg to about 2 mg/kg of the subject's body weight. In other embodiments the dose ranges from about 100 mg/kg to about 5 g/kg, about 500 mg/kg to about 2 mg/kg and about 750 mg/kg to about 1.5 g/kg of the subject's body weight. For example, depending on the type and severity of the disease, about 1 µg/kg to 15 mg/kg (e.g., 0.1-20 mg/kg) of agent is a candidate dosage for administration to the patient, whether, for example, by one or more separate administrations, or by continuous infusion. A typical daily dosage is in the range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. Unit doses can be in the range, for instance of about 5 mg to 500 mg, such as 50 mg, 100 mg, 150 mg, 200 mg, 250 mg and 300 mg. The progress of therapy is monitored by conventional techniques and assays.

In some embodiments, an agent is administered to a human patient at an effective amount (or dose) of less than about 1 µg/kg, for instance, about 0.35 to about 0.75 µg/kg or about 0.40 to about 0.60 µg/kg. In some embodiments, the dose of an agent is about 0.35 µg/kg, or about 0.40 µg/kg, or about 0.45 µg/kg, or about 0.50 µg/kg, or about 0.55 µg/kg, or about 0.60 µg/kg, or about 0.65 µg/kg, or about 0.70 µg/kg, or about 0.75 µg/kg, or about 0.80 µg/kg, or about 0.85 µg/kg, or about 0.90 µg/kg, or about 0.95 µg/kg or about 1 µg/kg. In various embodiments, the absolute dose of an agent is about 2 µg/subject to about 45 µg/subject, or about 5 to about 40, or about 10 to about 30, or about 15 to about 25 µg/subject. In some embodiments, the absolute dose of an agent is about 20 µg, or about 30 µg, or about 40 µg.

In various embodiments, the dose of an agent may be determined by the human patient's body weight. For example, an absolute dose of an agent of about 2 µg for a pediatric human patient of about 0 to about 5 kg (e.g. about 0, or about 1, or about 2, or about 3, or about 4, or about 5 kg); or about 3 µg for a pediatric human patient of about 6 to about 8 kg (e.g. about 6, or about 7, or about 8 kg), or about 5 µg for a pediatric human patient of about 9 to about 13 kg (e.g. 9, or about 10, or about 11, or about 12, or about 13 kg); or about 8 µg for a pediatric human patient of about 14 to about 20 kg (e.g. about 14, or about 16, or about 18, or about 20 kg), or about 12 µg for a pediatric human patient of about 21 to about 30 kg (e.g. about 21, or about 23, or about 25, or about 27, or about 30 kg), or about 13 µg for a pediatric human patient of about 31 to about 33 kg (e.g. about 31, or about 32, or about 33 kg), or about 20 µg for an adult human patient of about 34 to about 50 kg (e.g. about 34, or about 36, or about 38, or about 40, or about 42, or about 44, or about 46, or about 48, or about 50 kg), or about 30 µg for an adult human patient of about 51 to about 75 kg (e.g. about 51, or about 55, or about 60, or about 65, or about 70, or about 75 kg), or about 45 µg for an adult human patient of greater than about 114 kg (e.g. about 114, or about 120, or about 130, or about 140, or about 150 kg).

In addition to those compounds presented in the examples, the following compounds further illustrate the scope of the present disclosure:

TABLE 1

Summary of the compounds synthesized and tested in the present disclosure.

| Structure | Compound Number |
|---|---|
| 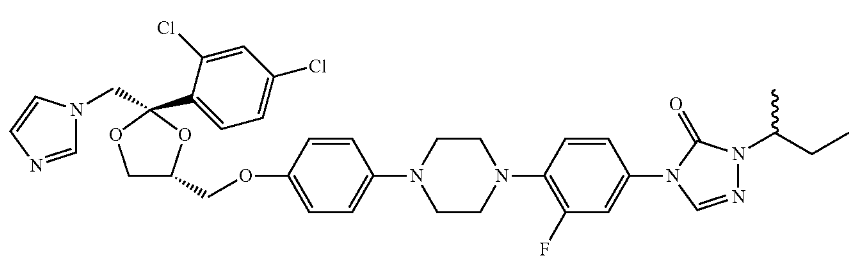 [SMILES: CCC(C)n1ncn(-c2ccc(N3CCN(c4ccc(OC[C@@H]5CO[C@@](Cn6ccnc6)(c6ccc(Cl)cc6Cl)O5)cc4)CC3)c(F)c2)c1=O] | 1 |

TABLE 1-continued
Summary of the compounds synthesized and tested in the present disclosure.
| Structure | Compound Number |
|---|---|
| 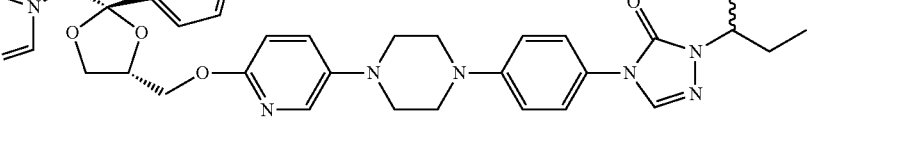 | 2 |
| 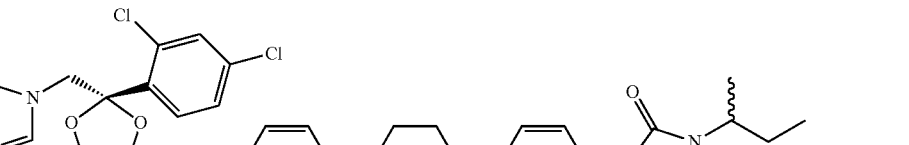 | 3 |
| 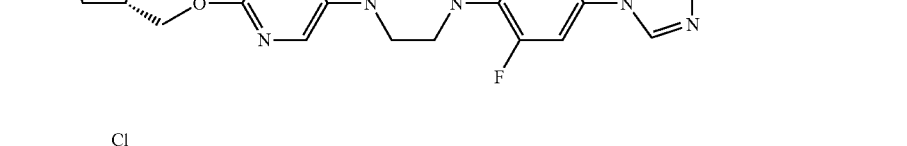 | 4 |
| 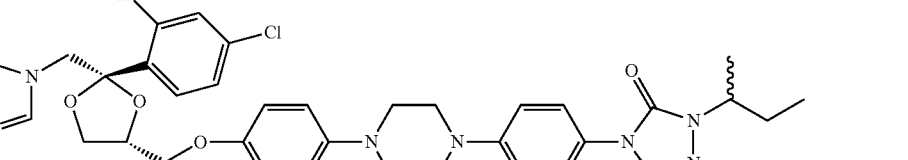 | 5 |
| 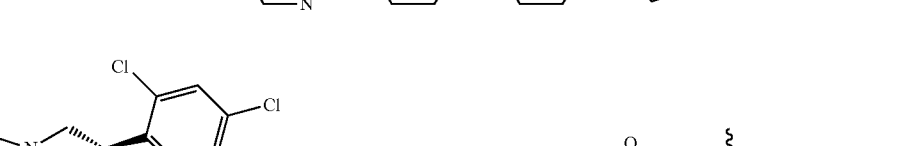 | 6 |
| 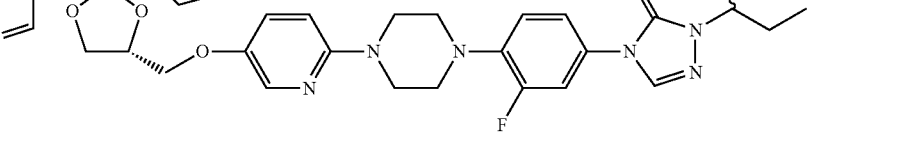 | 7 |

TABLE 1-continued
Summary of the compounds synthesized and tested in the present disclosure.
| Structure | Compound Number |
|---|---|
| 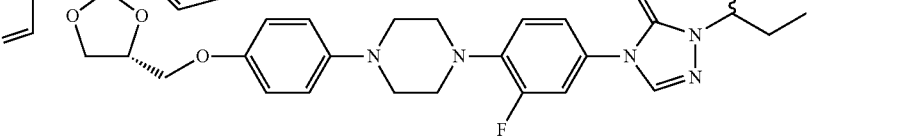 | 8 |
| 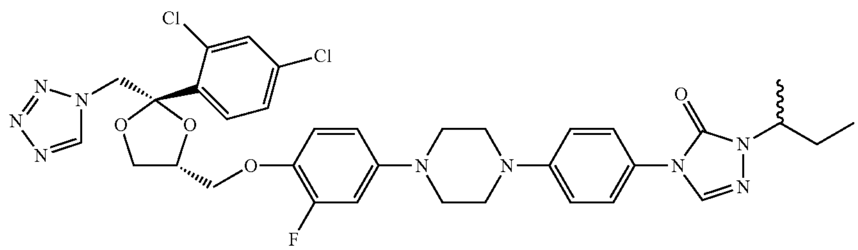 [SMILES: CCC(C)n1ncn(-c2ccc(N3CCN(c4ccc(OC[C@@H]5CO[C@@](Cn6cnnn6)(c6ccc(Cl)cc6Cl)O5)c(F)c4)CC3)cc2)c1=O] | 9 |
| 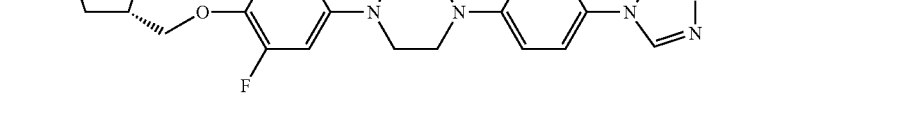 | 10 |
| 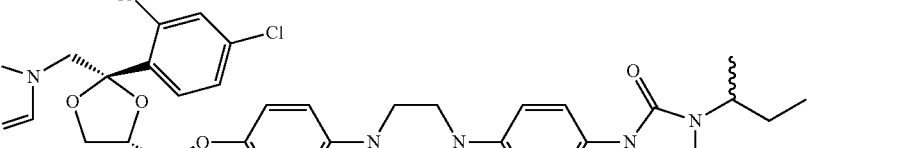 | 11 |
| 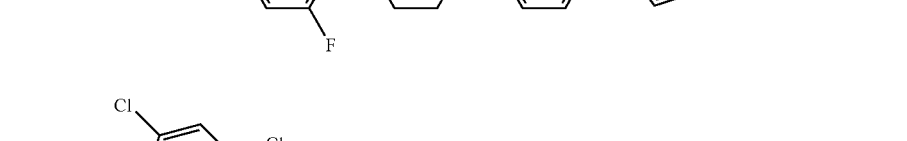 | 12 |
| 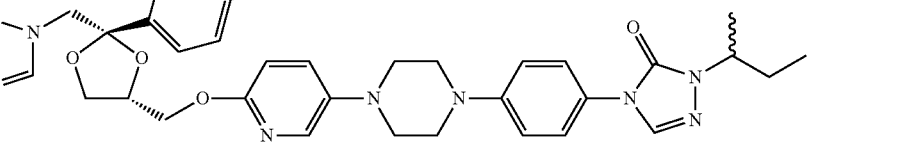 | 13 |

TABLE 1-continued

Summary of the compounds synthesized and tested in the present disclosure.

| Structure | Compound Number |
|---|---|
| 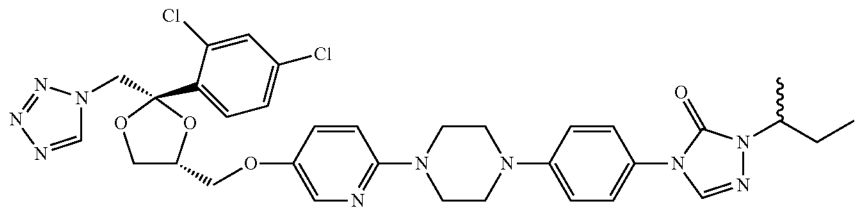 [SMILES: CCC(C)n1ncn(-c2ccc(N3CCN(c4ccc(OC[C@@H]5CO[C@@](Cn6cnnn6)(c6ccc(Cl)cc6Cl)O5)cn4)CC3)cc2)c1=O] | 14 |
| 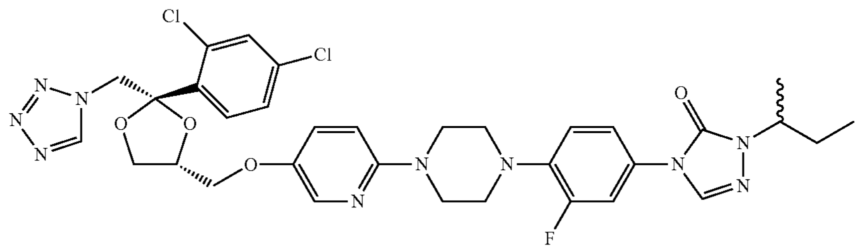 [SMILES: CCC(C)n1ncn(-c2ccc(N3CCN(c4ccc(OC[C@@H]5CO[C@@](Cn6cnnn6)(c6ccc(Cl)cc6Cl)O5)cn4)CC3)c(F)c2)c1=O] | 15 |
| 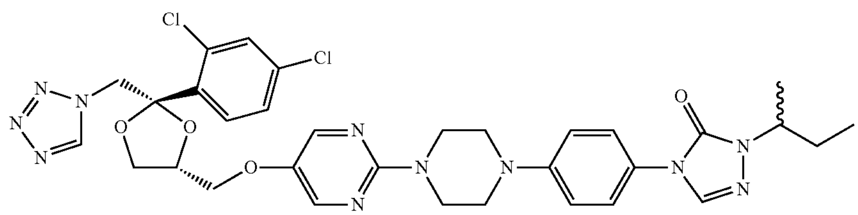 [SMILES: CCC(C)n1ncn(-c2ccc(N3CCN(c4ncc(OC[C@@H]5CO[C@@](Cn6cnnn6)(c6ccc(Cl)cc6Cl)O5)cn4)CC3)cc2)c1=O] | 16 |
| 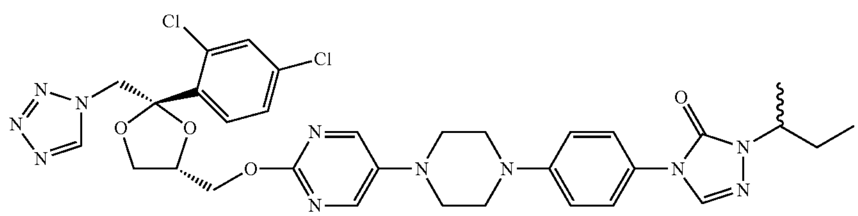 [SMILES: CCC(C)n1ncn(-c2ccc(N3CCN(c4cnc(OC[C@@H]5CO[C@@](Cn6cnnn6)(c6ccc(Cl)cc6Cl)O5)nc4)CC3)cc2)c1=O] | 17 |
| 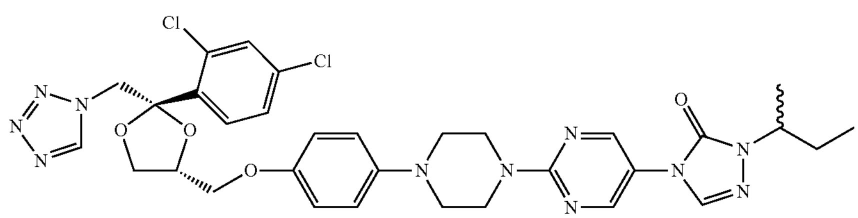 [SMILES: CCC(C)n1ncn(-c2cnc(N3CCN(c4ccc(OC[C@@H]5CO[C@@](Cn6cnnn6)(c6ccc(Cl)cc6Cl)O5)cc4)CC3)nc2)c1=O] | 18 |
| 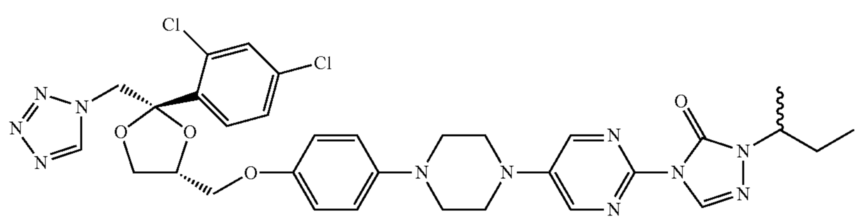 [SMILES: CCC(C)n1ncn(-c2ncc(N3CCN(c4ccc(OC[C@@H]5CO[C@@](Cn6cnnn6)(c6ccc(Cl)cc6Cl)O5)cc4)CC3)cn2)c1=O] | 19 |
| 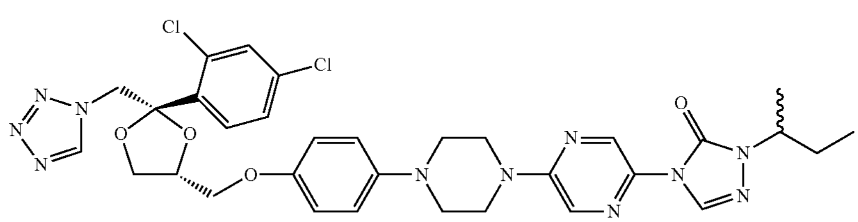 [SMILES: CCC(C)n1ncn(-c2cnc(N3CCN(c4ccc(OC[C@@H]5CO[C@@](Cn6cnnn6)(c6ccc(Cl)cc6Cl)O5)cc4)CC3)cn2)c1=O] | 20 |

TABLE 1-continued

Summary of the compounds synthesized and tested in the present disclosure.

| Structure | Compound Number |
|---|---|
| 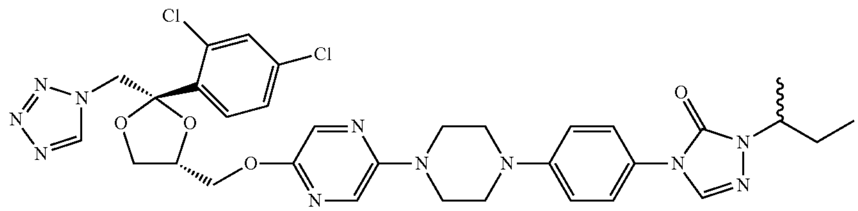 [SMILES: CCC(C)n1ncn(-c2ccc(N3CCN(c4cnc(OC[C@@H]5CO[C@@](Cn6cnnn6)(c6ccc(Cl)cc6Cl)O5)cn4)CC3)cc2)c1=O] | 21 |
| 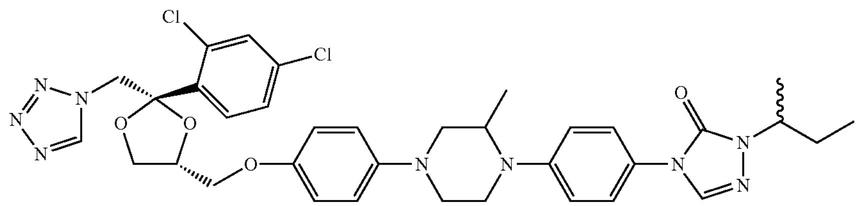 | 22 |
| 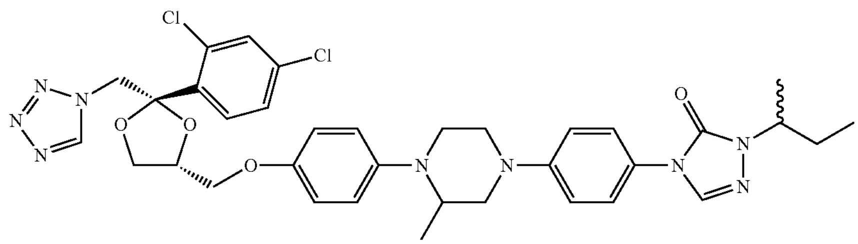 [SMILES: CCC(C)n1ncn(-c2ccc(N3CCN(c4ccc(OC[C@@H]5CO[C@@](Cn6cnnn6)(c6ccc(Cl)cc6Cl)O5)cc4)C(C)C3)cc2)c1=O] | 23 |
| 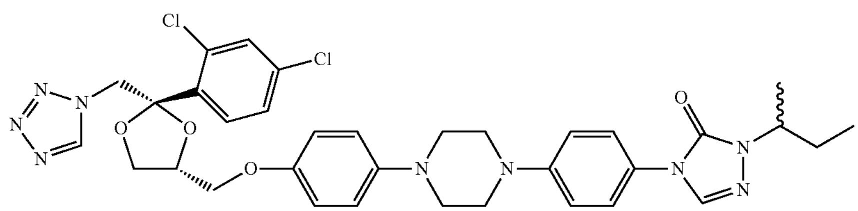 | 24 |
| 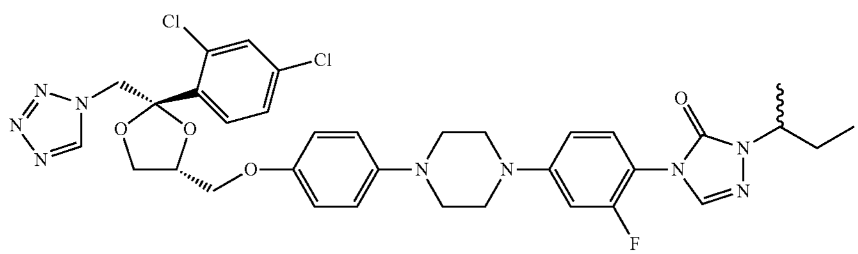 [SMILES: CCC(C)n1ncn(-c2ccc(N3CCN(c4ccc(OC[C@@H]5CO[C@@](Cn6cnnn6)(c6ccc(Cl)cc6Cl)O5)cc4)CC3)cc2F)c1=O] | 25 |
| 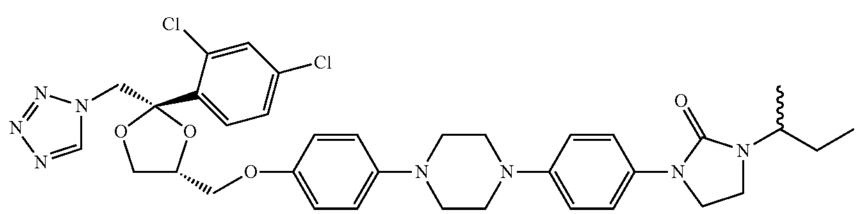 | 26 |
| 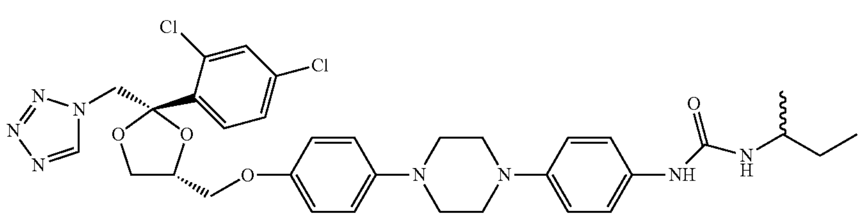 [SMILES: CCC(C)NC(=O)Nc1ccc(N2CCN(c3ccc(OC[C@@H]4CO[C@@](Cn5cnnn5)(c5ccc(Cl)cc5Cl)O4)cc3)CC2)cc1] | 27 |

TABLE 1-continued
Summary of the compounds synthesized and tested in the present disclosure.
| Structure | Compound Number |
|---|---|
| 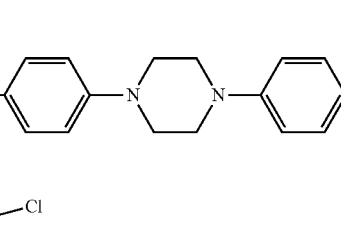 | 28 |
| 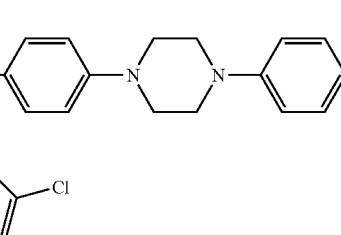 | 29 |
| 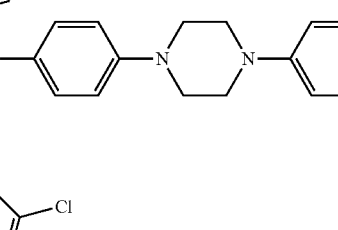 | 30 |
| 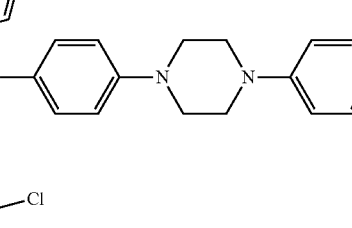 | 31 |
| 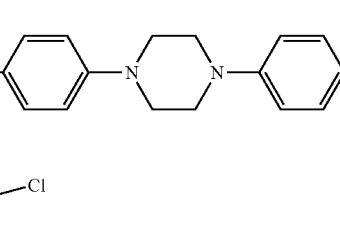 | 32 |
| 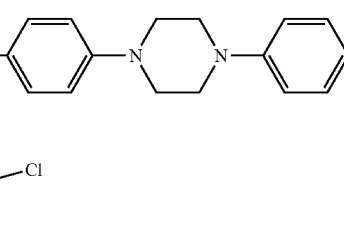 | 33 |
| 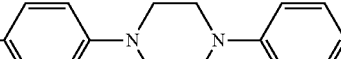 | 34 |

TABLE 1-continued
Summary of the compounds synthesized and tested in the present disclosure.
| Structure | Compound Number |
|---|---|
| 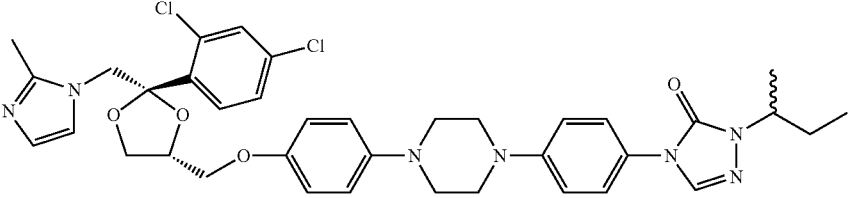 | 35 |
| 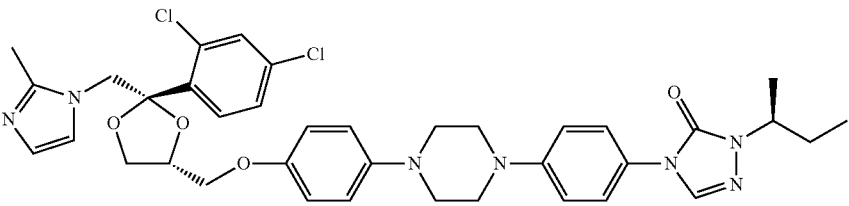 | 36 |
| 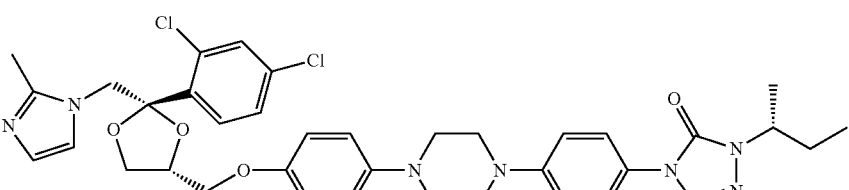 | 37 |
| 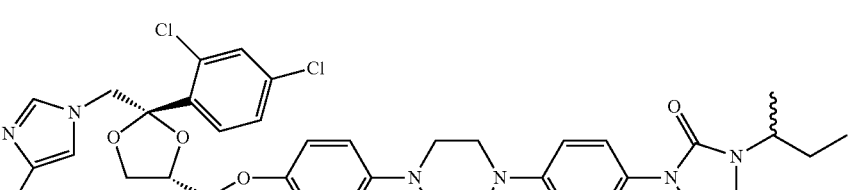 | 38 |
| 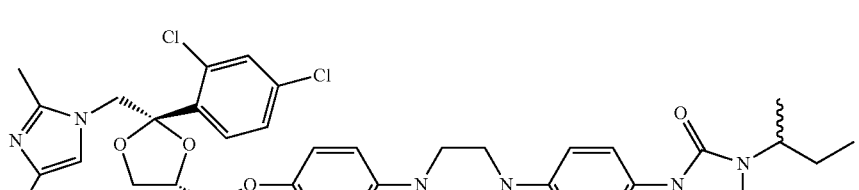 | 39 |
| 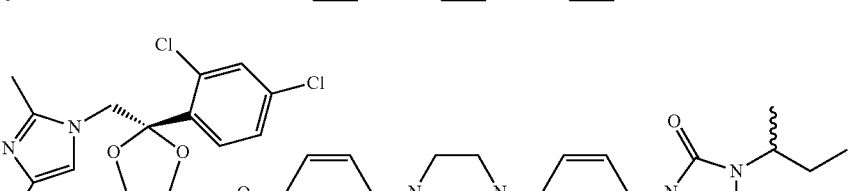 | 40 |
| 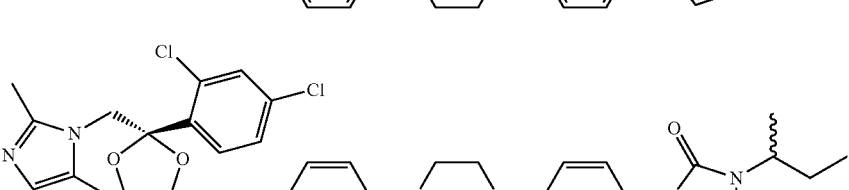 | 41 |

TABLE 1-continued
Summary of the compounds synthesized and tested in the present disclosure.
| Structure | Compound Number |
| --- | --- |
| 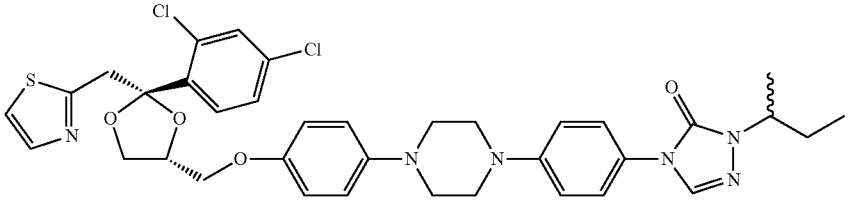 [SMILES: CCC(C)n1ncn(-c2ccc(N3CCN(c4ccc(OC[C@@H]5CO[C@@](Cc6nccs6)(c6ccc(Cl)cc6Cl)O5)cc4)CC3)cc2)c1=O] | 42 |
| 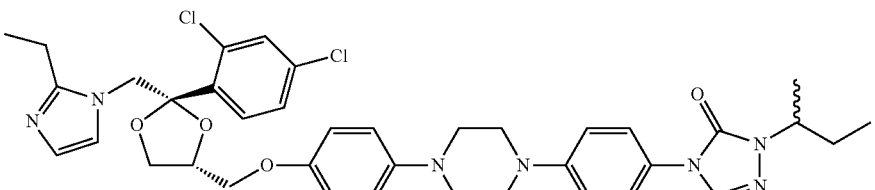 | 43 |
| 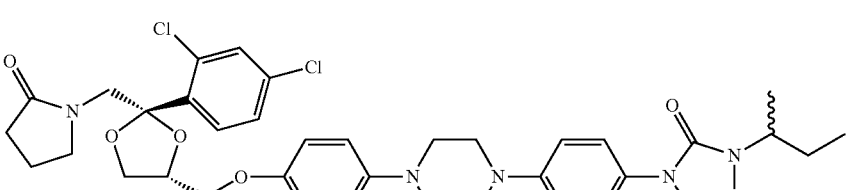 | 44 |
| 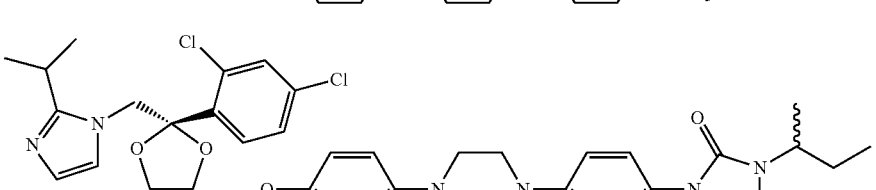 | 45 |
| 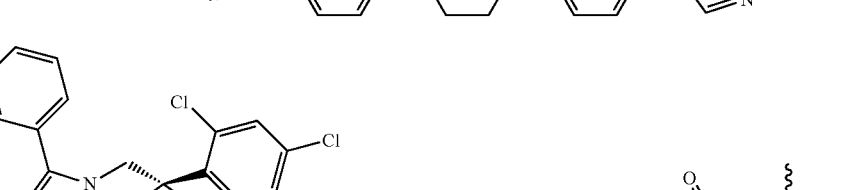 | 46 |
| 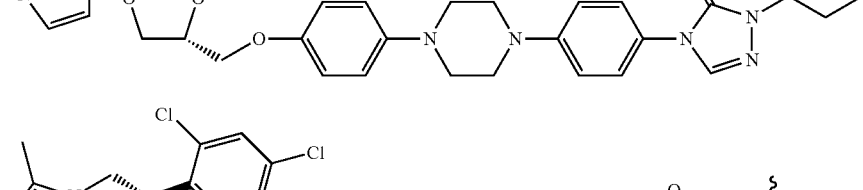 | 47 |
| 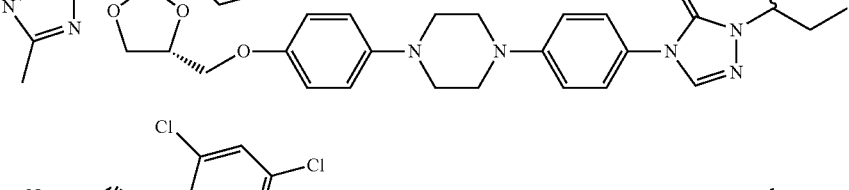 | 48 |

TABLE 1-continued

Summary of the compounds synthesized and tested in the present disclosure.

| Structure | Compound Number |
|---|---|
| 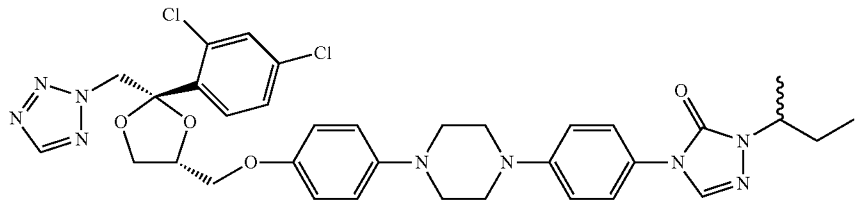 [SMILES: CCC(C)n1ncn(-c2ccc(N3CCN(c4ccc(OC[C@@H]5CO[C@@](Cn6ncnn6)(c6ccc(Cl)cc6Cl)O5)cc4)CC3)cc2)c1=O] | 49 |
| 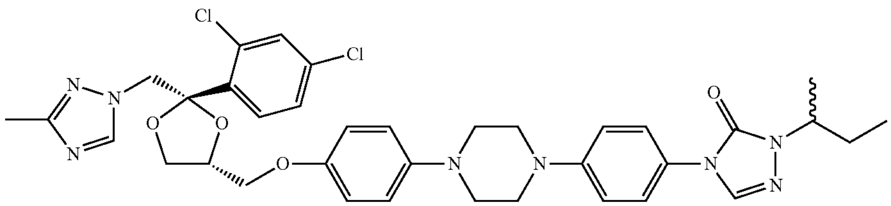 [SMILES: CCC(C)n1ncn(-c2ccc(N3CCN(c4ccc(OC[C@@H]5CO[C@@](Cn6cnc(C)n6)(c6ccc(Cl)cc6Cl)O5)cc4)CC3)cc2)c1=O] | 50 |
| 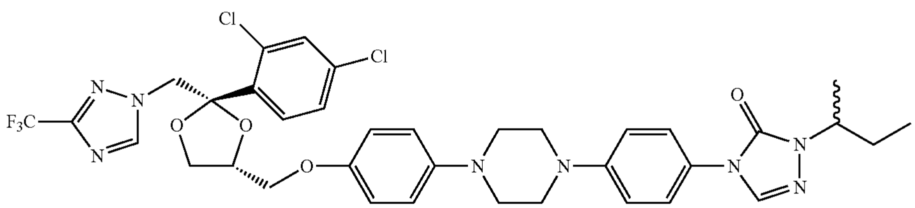 [SMILES: CCC(C)n1ncn(-c2ccc(N3CCN(c4ccc(OC[C@@H]5CO[C@@](Cn6cnc(C(F)(F)F)n6)(c6ccc(Cl)cc6Cl)O5)cc4)CC3)cc2)c1=O] | 51 |
| 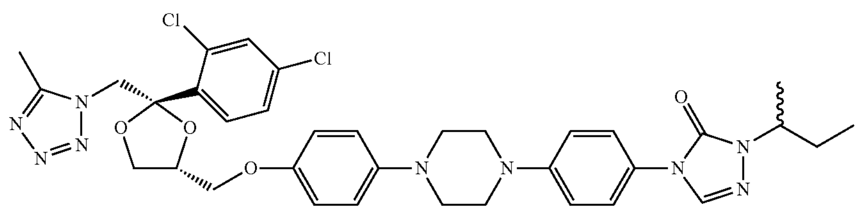 [SMILES: CCC(C)n1ncn(-c2ccc(N3CCN(c4ccc(OC[C@@H]5CO[C@@](Cn6nnnc6C)(c6ccc(Cl)cc6Cl)O5)cc4)CC3)cc2)c1=O] | 52 |
| 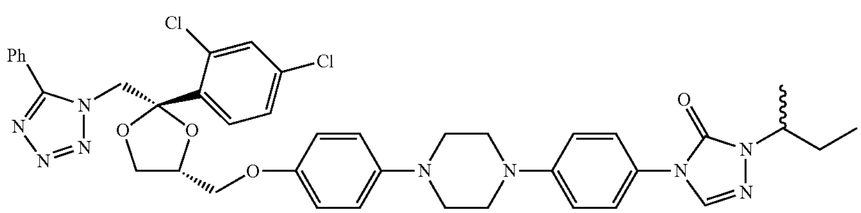 [SMILES: CCC(C)n1ncn(-c2ccc(N3CCN(c4ccc(OC[C@@H]5CO[C@@](Cn6nnnc6-c6ccccc6)(c6ccc(Cl)cc6Cl)O5)cc4)CC3)cc2)c1=O] | 53 |
| 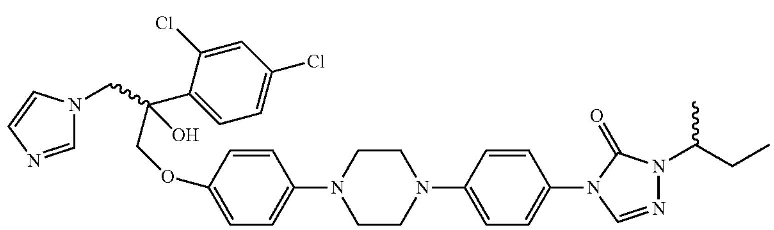 [SMILES: CCC(C)n1ncn(-c2ccc(N3CCN(c4ccc(OCC(O)(Cn5ccnc5)c5ccc(Cl)cc5Cl)cc4)CC3)cc2)c1=O] | 54 |
| 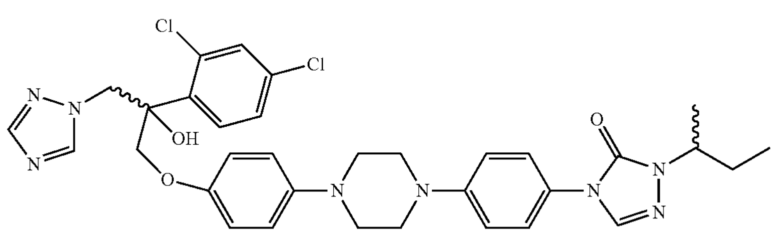 [SMILES: CCC(C)n1ncn(-c2ccc(N3CCN(c4ccc(OCC(O)(Cn5cncn5)c5ccc(Cl)cc5Cl)cc4)CC3)cc2)c1=O] | 55 |

TABLE 1-continued

Summary of the compounds synthesized and tested in the present disclosure.

| Structure | Compound Number |
| --- | --- |
| 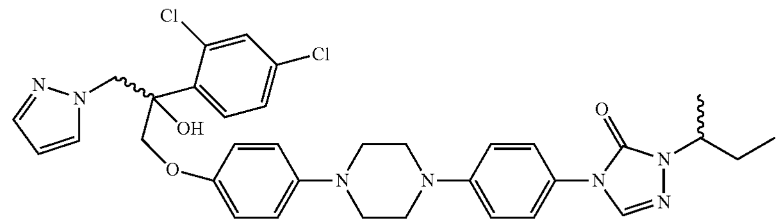 [SMILES: CCC(C)n1ncn(-c2ccc(N3CCN(c4ccc(OCC(O)(Cn5cccn5)c5ccc(Cl)cc5Cl)cc4)CC3)cc2)c1=O] | 56 |
| 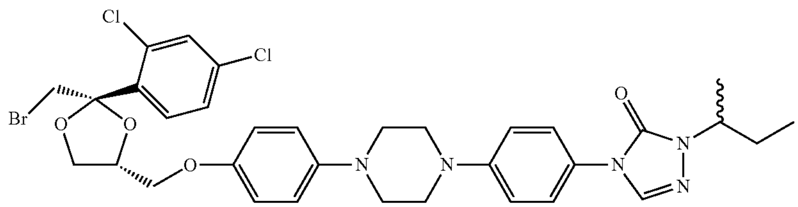 [SMILES: CCC(C)n1ncn(-c2ccc(N3CCN(c4ccc(OC[C@@H]5CO[C@@](CBr)(c6ccc(Cl)cc6Cl)O5)cc4)CC3)cc2)c1=O] | 57 |
| 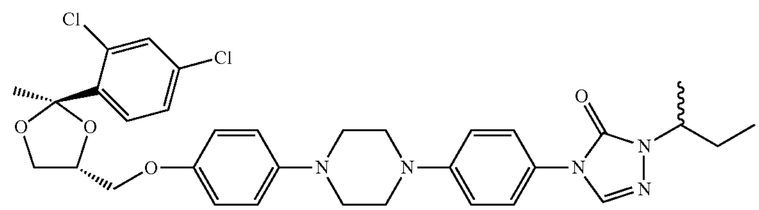 [SMILES: CCC(C)n1ncn(-c2ccc(N3CCN(c4ccc(OC[C@@H]5CO[C@@](C)(c6ccc(Cl)cc6Cl)O5)cc4)CC3)cc2)c1=O] | 58 |
| 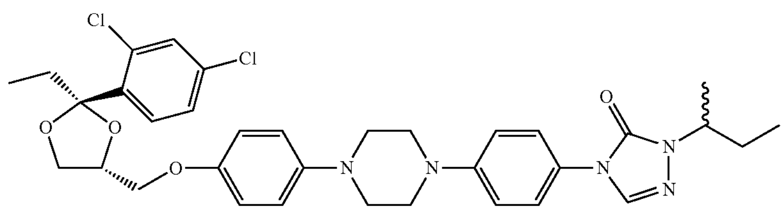 [SMILES: CCC(C)n1ncn(-c2ccc(N3CCN(c4ccc(OC[C@@H]5CO[C@@](CC)(c6ccc(Cl)cc6Cl)O5)cc4)CC3)cc2)c1=O] | 59 |
| 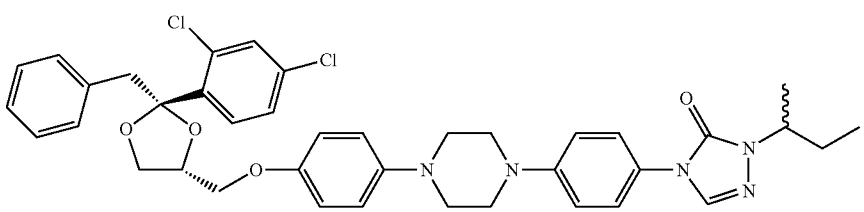 [SMILES: CCC(C)n1ncn(-c2ccc(N3CCN(c4ccc(OC[C@@H]5CO[C@@](Cc6ccccc6)(c6ccc(Cl)cc6Cl)O5)cc4)CC3)cc2)c1=O] | 60 |
| 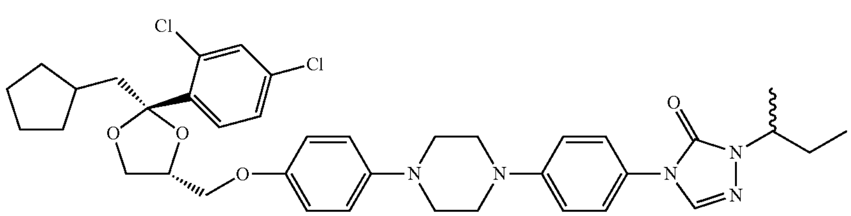 [SMILES: CCC(C)n1ncn(-c2ccc(N3CCN(c4ccc(OC[C@@H]5CO[C@@](CC6CCCC6)(c6ccc(Cl)cc6Cl)O5)cc4)CC3)cc2)c1=O] | 61 |

TABLE 1-continued

Summary of the compounds synthesized and tested in the present disclosure.

| Structure | Compound Number |
|---|---|
| 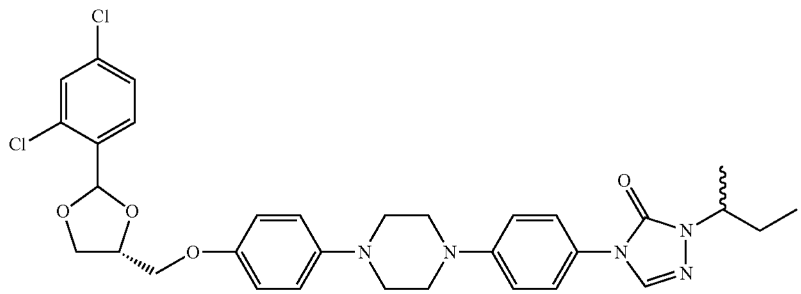 [SMILES: CCC(C)n1ncn(-c2ccc(N3CCN(c4ccc(OC[C@@H]5COC(c6ccc(Cl)cc6Cl)O5)cc4)CC3)cc2)c1=O] | 62 |
| 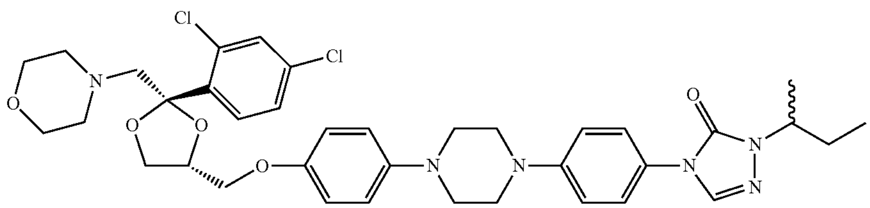 [SMILES: CCC(C)n1ncn(-c2ccc(N3CCN(c4ccc(OC[C@@H]5CO[C@@](CN6CCOCC6)(c6ccc(Cl)cc6Cl)O5)cc4)CC3)cc2)c1=O] | 63 |
| 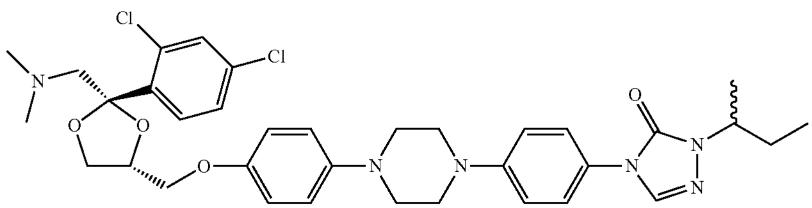 [SMILES: CCC(C)n1ncn(-c2ccc(N3CCN(c4ccc(OC[C@@H]5CO[C@@](CN(C)C)(c6ccc(Cl)cc6Cl)O5)cc4)CC3)cc2)c1=O] | 64 |
| 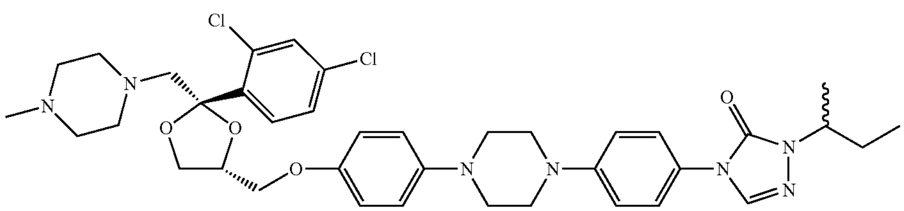 [SMILES: CCC(C)n1ncn(-c2ccc(N3CCN(c4ccc(OC[C@@H]5CO[C@@](CN6CCN(C)CC6)(c6ccc(Cl)cc6Cl)O5)cc4)CC3)cc2)c1=O] | 65 |
| 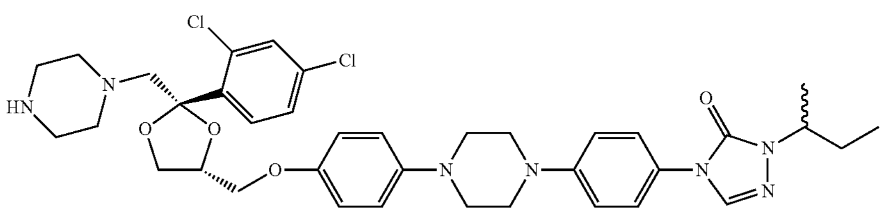 [SMILES: CCC(C)n1ncn(-c2ccc(N3CCN(c4ccc(OC[C@@H]5CO[C@@](CN6CCNCC6)(c6ccc(Cl)cc6Cl)O5)cc4)CC3)cc2)c1=O] | 66 |
| 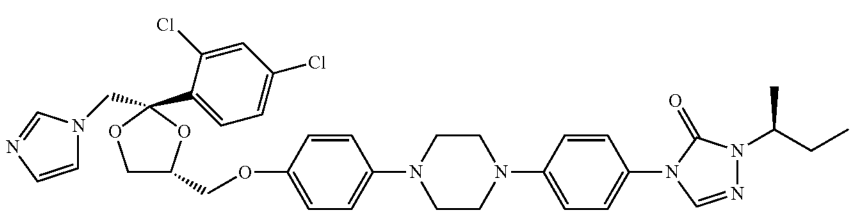 [SMILES: CC[C@H](C)n1ncn(-c2ccc(N3CCN(c4ccc(OC[C@@H]5CO[C@@](Cn6ccnc6)(c6ccc(Cl)cc6Cl)O5)cc4)CC3)cc2)c1=O] | 67 |
| 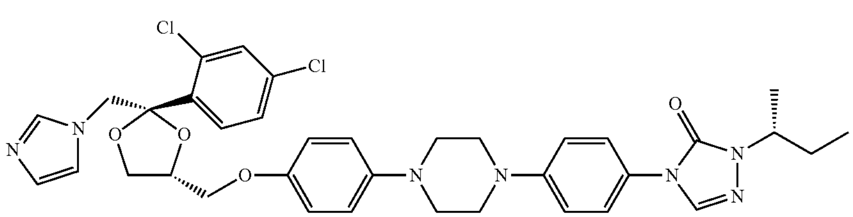 [SMILES: CC[C@@H](C)n1ncn(-c2ccc(N3CCN(c4ccc(OC[C@@H]5CO[C@@](Cn6ccnc6)(c6ccc(Cl)cc6Cl)O5)cc4)CC3)cc2)c1=O] | 68 |

TABLE 1-continued

Summary of the compounds synthesized and tested in the present disclosure.

| Structure | Compound Number |
|---|---|
| 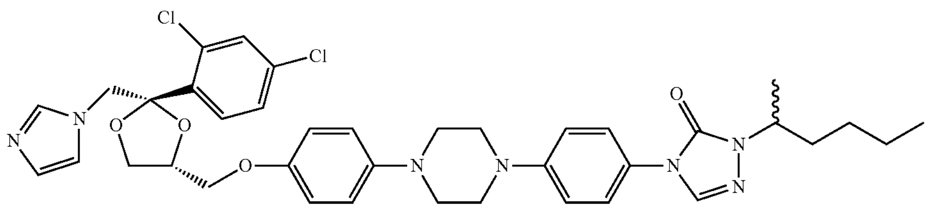 [SMILES: CCCCC(C)n1ncn(-c2ccc(N3CCN(c4ccc(OC[C@@H]5CO[C@@](Cn6ccnc6)(c6ccc(Cl)cc6Cl)O5)cc4)CC3)cc2)c1=O] | 69 |
| 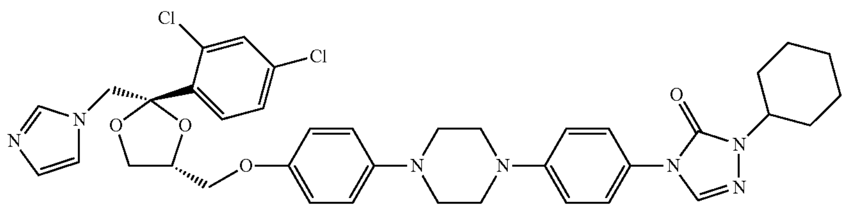 [SMILES: O=c1n(-c2ccc(N3CCN(c4ccc(OC[C@@H]5CO[C@@](Cn6ccnc6)(c6ccc(Cl)cc6Cl)O5)cc4)CC3)cc2)cnn1C1CCCCC1] | 70 |
| 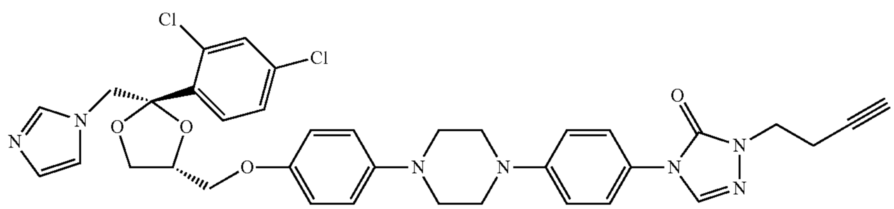 [SMILES: C#CCCn1ncn(-c2ccc(N3CCN(c4ccc(OC[C@@H]5CO[C@@](Cn6ccnc6)(c6ccc(Cl)cc6Cl)O5)cc4)CC3)cc2)c1=O] | 71 |
| 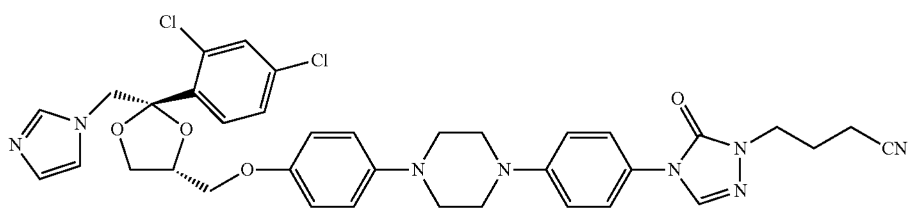 [SMILES: N#CCCCn1ncn(-c2ccc(N3CCN(c4ccc(OC[C@@H]5CO[C@@](Cn6ccnc6)(c6ccc(Cl)cc6Cl)O5)cc4)CC3)cc2)c1=O] | 72 |
| 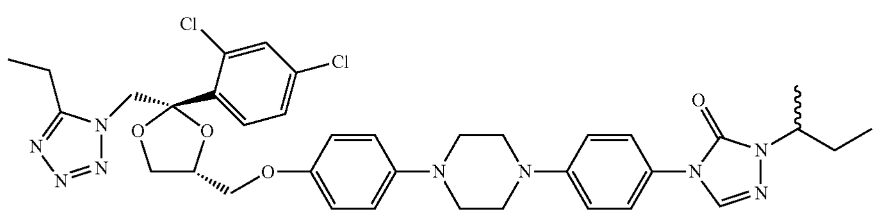 [SMILES: CCc1nnnn1C[C@@]1(c2ccc(Cl)cc2Cl)OC[C@@H](COc2ccc(N3CCN(c4ccc(-n5cnn(C(C)CC)c5=O)cc4)CC3)cc2)O1] | 73 |
| 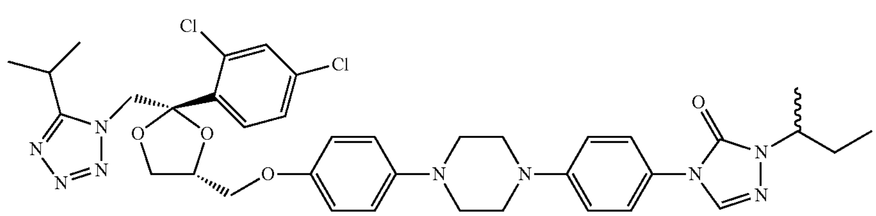 [SMILES: CCC(C)n1ncn(-c2ccc(N3CCN(c4ccc(OC[C@@H]5CO[C@@](Cn6nnnc6C(C)C)(c6ccc(Cl)cc6Cl)O5)cc4)CC3)cc2)c1=O] | 74 |
| 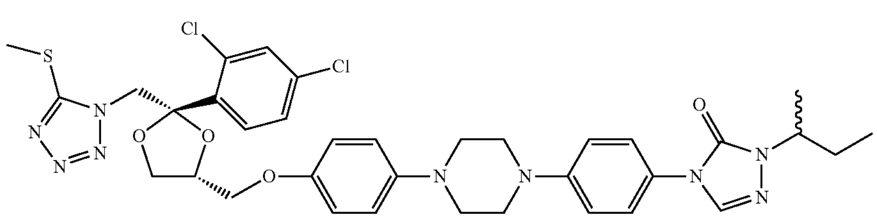 [SMILES: CCC(C)n1ncn(-c2ccc(N3CCN(c4ccc(OC[C@@H]5CO[C@@](Cn6nnnc6SC)(c6ccc(Cl)cc6Cl)O5)cc4)CC3)cc2)c1=O] | 75 |

TABLE 1-continued

Summary of the compounds synthesized and tested in the present disclosure.

| Structure | Compound Number |
|---|---|
| 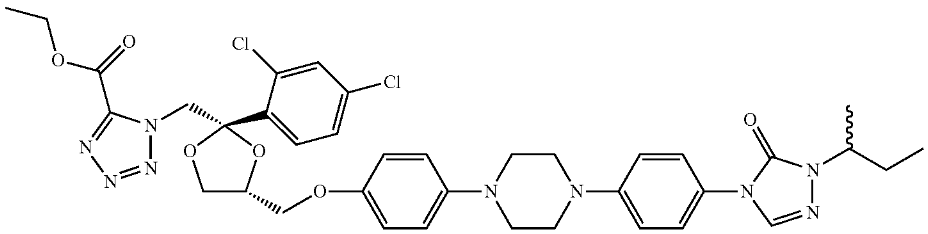 [SMILES: CCOC(=O)c1nnnn1C[C@@]1(c2ccc(Cl)cc2Cl)OC[C@@H](COc2ccc(N3CCN(c4ccc(-n5cnn(C(C)CC)c5=O)cc4)CC3)cc2)O1] | 76 |
| 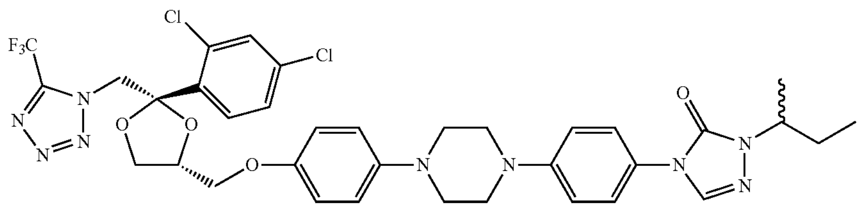 | 77 |
| 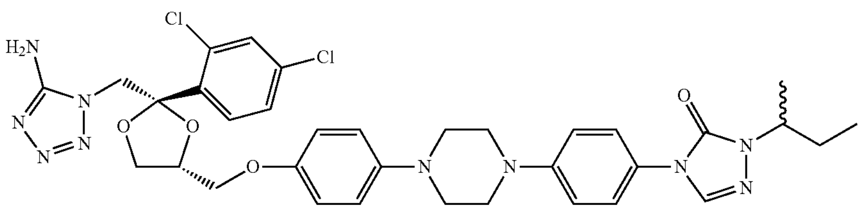 | 78 |
| 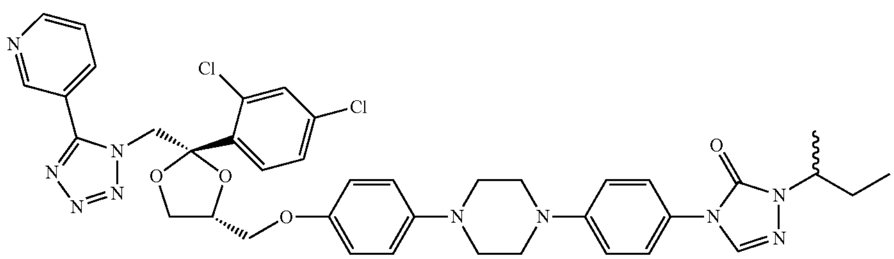 [SMILES: CCC(C)n1ncn(-c2ccc(N3CCN(c4ccc(OC[C@@H]5CO[C@@](Cn6nnnc6-c6cccnc6)(c6ccc(Cl)cc6Cl)O5)cc4)CC3)cc2)c1=O] | 79 |
| 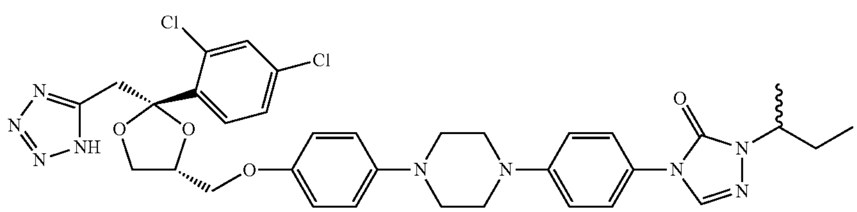 [SMILES: CCC(C)n1ncn(-c2ccc(N3CCN(c4ccc(OC[C@@H]5CO[C@@](Cc6nnn[nH]6)(c6ccc(Cl)cc6Cl)O5)cc4)CC3)cc2)c1=O] | 80 |
| 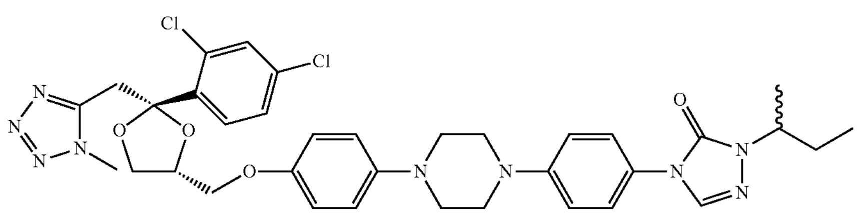 [SMILES: CCC(C)n1ncn(-c2ccc(N3CCN(c4ccc(OC[C@@H]5CO[C@@](Cc6nnnn6C)(c6ccc(Cl)cc6Cl)O5)cc4)CC3)cc2)c1=O] | 81 |
| 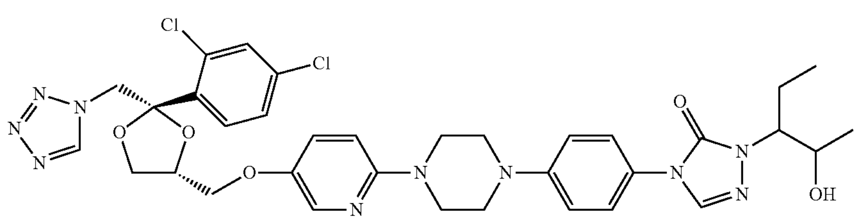 | 82 |

TABLE 1-continued

Summary of the compounds synthesized and tested in the present disclosure.

| Structure | Compound Number |
| --- | --- |
| 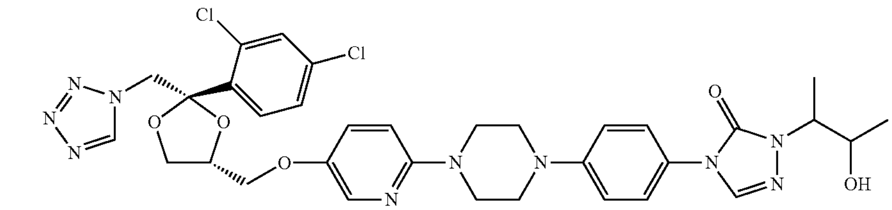 [SMILES: CC(O)C(C)n1ncn(-c2ccc(N3CCN(c4ccc(OC[C@@H]5CO[C@@](Cn6cnnn6)(c6ccc(Cl)cc6Cl)O5)cn4)CC3)cc2)c1=O] | 83 |
| 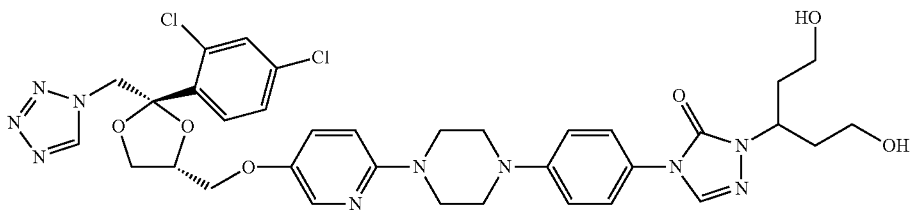 [SMILES: O=c1n(-c2ccc(N3CCN(c4ccc(OC[C@@H]5CO[C@@](Cn6cnnn6)(c6ccc(Cl)cc6Cl)O5)cn4)CC3)cc2)cnn1C(CCO)CCO] | 84 |
| 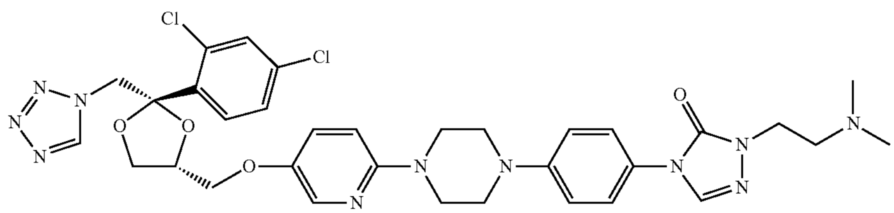 [SMILES: CN(C)CCn1ncn(-c2ccc(N3CCN(c4ccc(OC[C@@H]5CO[C@@](Cn6cnnn6)(c6ccc(Cl)cc6Cl)O5)cn4)CC3)cc2)c1=O] | 85 |
| 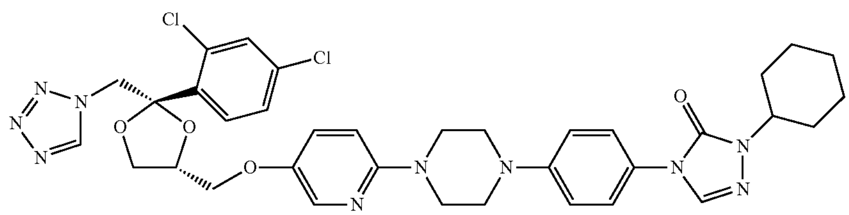 [SMILES: O=c1n(-c2ccc(N3CCN(c4ccc(OC[C@@H]5CO[C@@](Cn6cnnn6)(c6ccc(Cl)cc6Cl)O5)cn4)CC3)cc2)cnn1C1CCCCC1] | 86 |
| 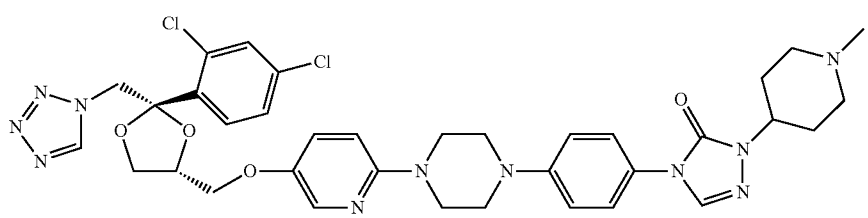 [SMILES: CN1CCC(n2ncn(-c3ccc(N4CCN(c5ccc(OC[C@@H]6CO[C@@](Cn7cnnn7)(c7ccc(Cl)cc7Cl)O6)cn5)CC4)cc3)c2=O)CC1] | 87 |
| 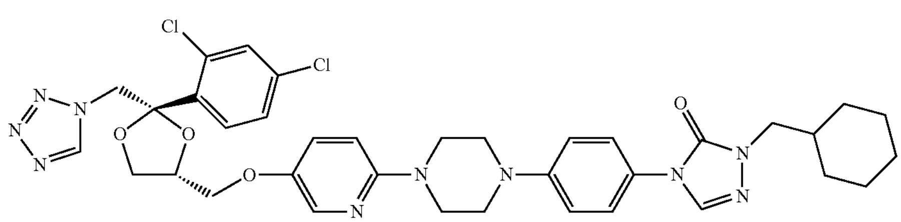 [SMILES: O=c1n(-c2ccc(N3CCN(c4ccc(OC[C@@H]5CO[C@@](Cn6cnnn6)(c6ccc(Cl)cc6Cl)O5)cn4)CC3)cc2)cnn1CC1CCCCC1] | 88 |
| 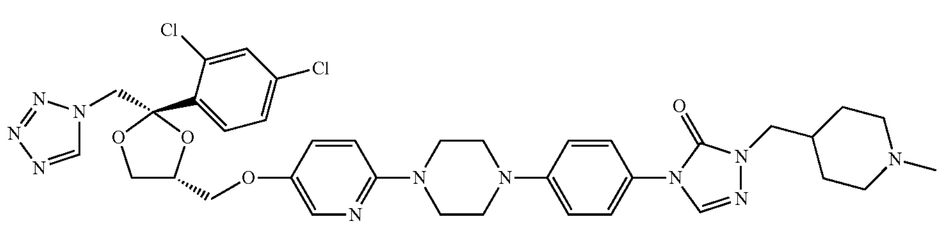 [SMILES: CN1CCC(Cn2ncn(-c3ccc(N4CCN(c5ccc(OC[C@@H]6CO[C@@](Cn7cnnn7)(c7ccc(Cl)cc7Cl)O6)cn5)CC4)cc3)c2=O)CC1] | 89 |

TABLE 1-continued

Summary of the compounds synthesized and tested in the present disclosure.

| Structure | Compound Number |
|---|---|
| 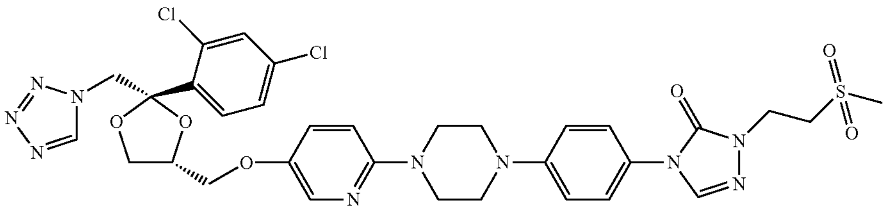 [SMILES: CS(=O)(=O)CCn1ncn(-c2ccc(N3CCN(c4ccc(OC[C@@H]5CO[C@@](Cn6cnnn6)(c6ccc(Cl)cc6Cl)O5)cn4)CC3)cc2)c1=O] | 90 |
| 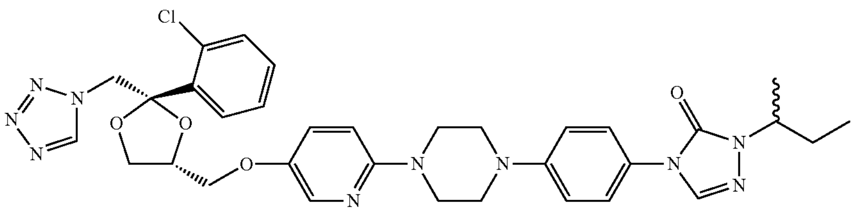 [SMILES: CCC(C)n1ncn(-c2ccc(N3CCN(c4ccc(OC[C@@H]5CO[C@@](Cn6cnnn6)(c6ccccc6Cl)O5)cn4)CC3)cc2)c1=O] | 91 |
| 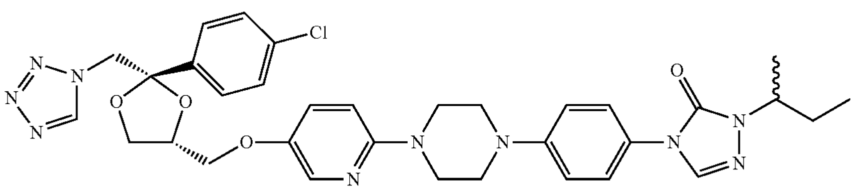 [SMILES: CCC(C)n1ncn(-c2ccc(N3CCN(c4ccc(OC[C@@H]5CO[C@@](Cn6cnnn6)(c6ccc(Cl)cc6)O5)cn4)CC3)cc2)c1=O] | 92 |
| 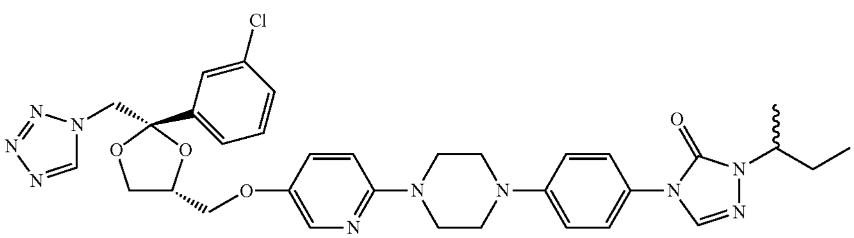 [SMILES: CCC(C)n1ncn(-c2ccc(N3CCN(c4ccc(OC[C@@H]5CO[C@@](Cn6cnnn6)(c6cccc(Cl)c6)O5)cn4)CC3)cc2)c1=O] | 93 |
| 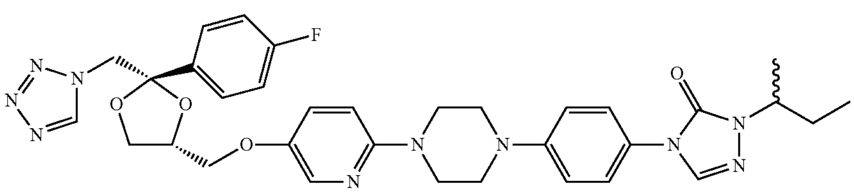 [SMILES: CCC(C)n1ncn(-c2ccc(N3CCN(c4ccc(OC[C@@H]5CO[C@@](Cn6cnnn6)(c6ccc(F)cc6)O5)cn4)CC3)cc2)c1=O] | 94 |
| 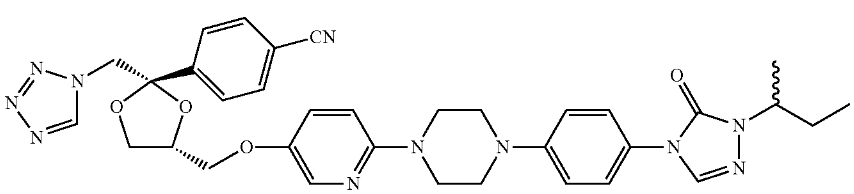 [SMILES: CCC(C)n1ncn(-c2ccc(N3CCN(c4ccc(OC[C@@H]5CO[C@@](Cn6cnnn6)(c6ccc(C#N)cc6)O5)cn4)CC3)cc2)c1=O] | 95 |
| 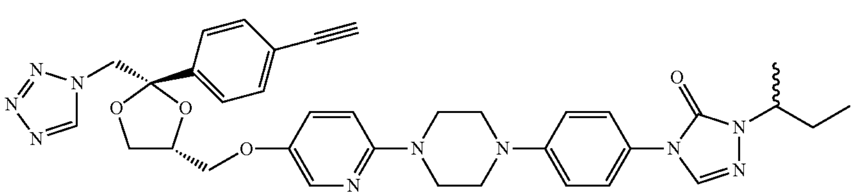 [SMILES: C#Cc1ccc([C@]2(Cn3cnnn3)OC[C@@H](COc3ccc(N4CCN(c5ccc(-n6cnn(C(C)CC)c6=O)cc5)CC4)nc3)O2)cc1] | 96 |

TABLE 1-continued

Summary of the compounds synthesized and tested in the present disclosure.

| Structure | Compound Number |
| --- | --- |
| 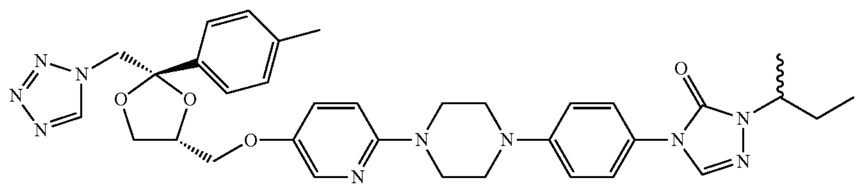 [SMILES: CCC(C)n1ncn(-c2ccc(N3CCN(c4ccc(OC[C@@H]5CO[C@@](Cn6cnnn6)(c6ccc(C)cc6)O5)cn4)CC3)cc2)c1=O] | 97 |
| 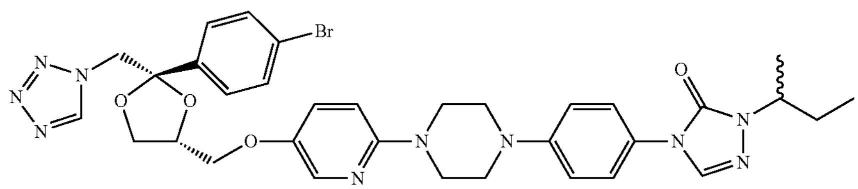 [SMILES: CCC(C)n1ncn(-c2ccc(N3CCN(c4ccc(OC[C@@H]5CO[C@@](Cn6cnnn6)(c6ccc(Br)cc6)O5)cn4)CC3)cc2)c1=O] | 98 |
| 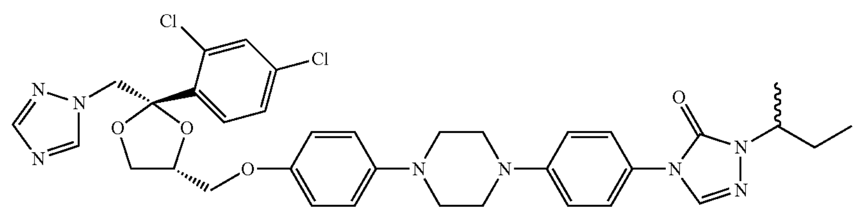 [SMILES: CCC(C)n1ncn(-c2ccc(N3CCN(c4ccc(OC[C@@H]5CO[C@@](Cn6cncn6)(c6ccc(Cl)cc6Cl)O5)cc4)CC3)cc2)c1=O] | 99 |
| 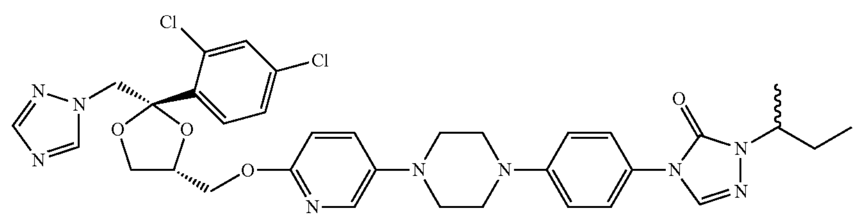 [SMILES: CCC(C)n1ncn(-c2ccc(N3CCN(c4ccc(OC[C@@H]5CO[C@@](Cn6cncn6)(c6ccc(Cl)cc6Cl)O5)nc4)CC3)cc2)c1=O] | 100 |
| 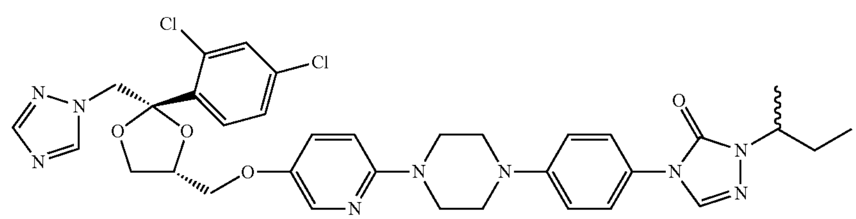 [SMILES: CCC(C)n1ncn(-c2ccc(N3CCN(c4ccc(OC[C@@H]5CO[C@@](Cn6cncn6)(c6ccc(Cl)cc6Cl)O5)cn4)CC3)cc2)c1=O] | 101 |
| 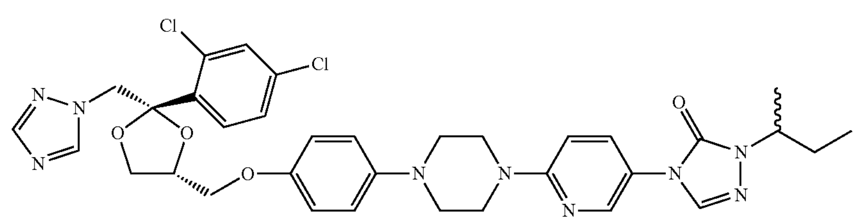 [SMILES: CCC(C)n1ncn(-c2ccc(N3CCN(c4ccc(OC[C@@H]5CO[C@@](Cn6cncn6)(c6ccc(Cl)cc6Cl)O5)cc4)CC3)nc2)c1=O] | 102 |
| 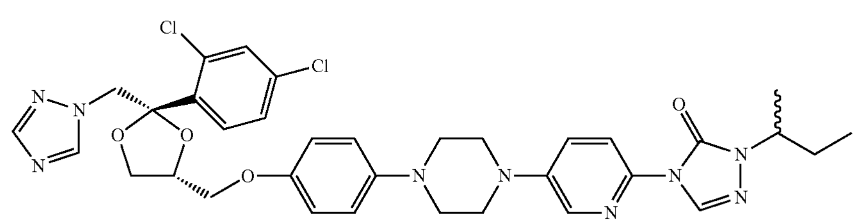 [SMILES: CCC(C)n1ncn(-c2ccc(N3CCN(c4ccc(OC[C@@H]5CO[C@@](Cn6cncn6)(c6ccc(Cl)cc6Cl)O5)cc4)CC3)cn2)c1=O] | 103 |

TABLE 1-continued

Summary of the compounds synthesized and tested in the present disclosure.

| Structure | Compound Number |
|---|---|
| 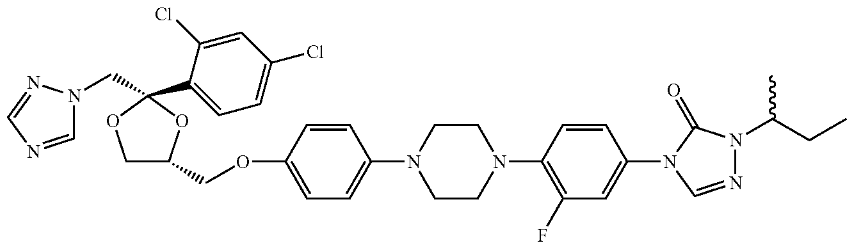 [SMILES: CCC(C)n1ncn(-c2ccc(N3CCN(c4ccc(OC[C@@H]5CO[C@@](Cn6cncn6)(c6ccc(Cl)cc6Cl)O5)cc4)CC3)c(F)c2)c1=O] | 104 |
| 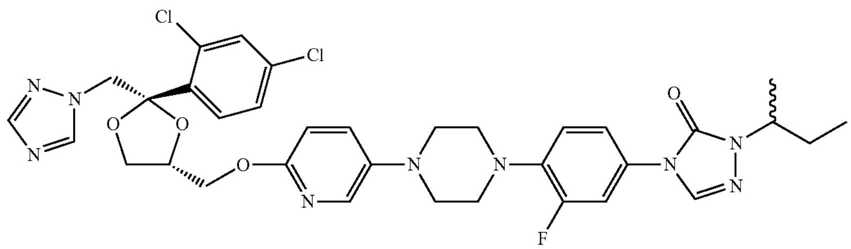 [SMILES: CCC(C)n1ncn(-c2ccc(N3CCN(c4ccc(OC[C@@H]5CO[C@@](Cn6cncn6)(c6ccc(Cl)cc6Cl)O5)nc4)CC3)c(F)c2)c1=O] | 105 |
| 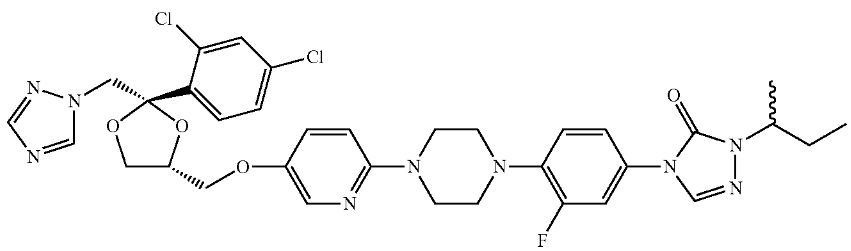 [SMILES: CCC(C)n1ncn(-c2ccc(N3CCN(c4ccc(OC[C@@H]5CO[C@@](Cn6cncn6)(c6ccc(Cl)cc6Cl)O5)cn4)CC3)c(F)c2)c1=O] | 106 |
| 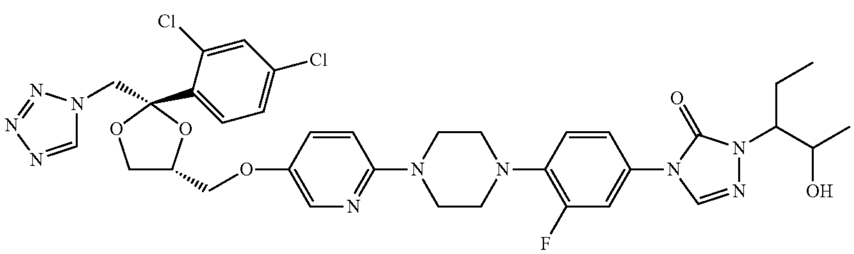 [SMILES: CCC(C(C)O)n1ncn(-c2ccc(N3CCN(c4ccc(OC[C@@H]5CO[C@@](Cn6cnnn6)(c6ccc(Cl)cc6Cl)O5)cn4)CC3)c(F)c2)c1=O] | 107 |
| 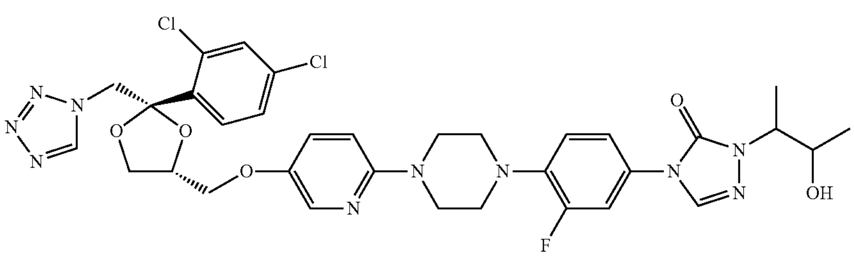 [SMILES: CC(O)C(C)n1ncn(-c2ccc(N3CCN(c4ccc(OC[C@@H]5CO[C@@](Cn6cnnn6)(c6ccc(Cl)cc6Cl)O5)cn4)CC3)c(F)c2)c1=O] | 108 |
| 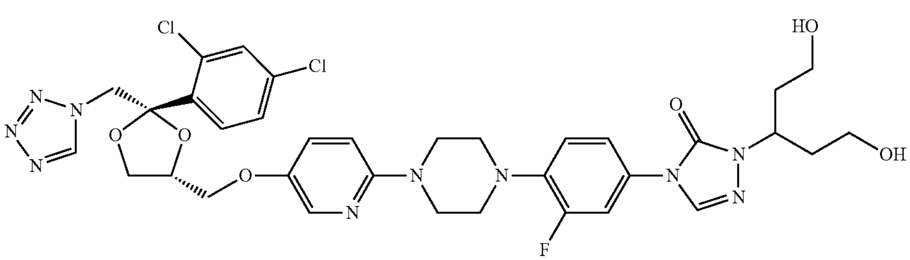 [SMILES: O=c1n(-c2ccc(N3CCN(c4ccc(OC[C@@H]5CO[C@@](Cn6cnnn6)(c6ccc(Cl)cc6Cl)O5)cn4)CC3)c(F)c2)cnn1C(CCO)CCO] | 109 |

TABLE 1-continued

Summary of the compounds synthesized and tested in the present disclosure.

| Structure | Compound Number |
|---|---|
| 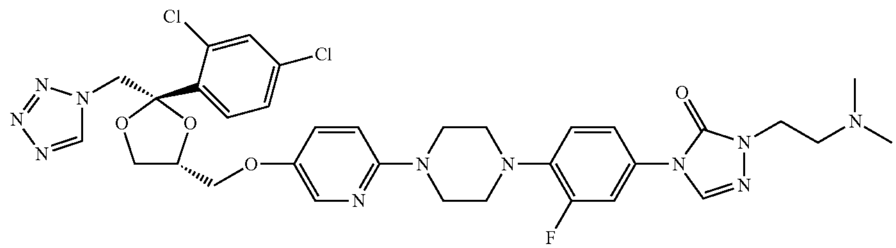 [SMILES: CN(C)CCn1ncn(-c2ccc(N3CCN(c4ccc(OC[C@@H]5CO[C@@](Cn6cnnn6)(c6ccc(Cl)cc6Cl)O5)cn4)CC3)c(F)c2)c1=O] | 110 |
| 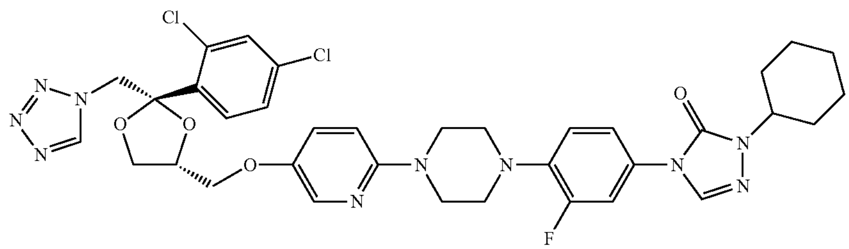 [SMILES: O=c1n(-c2ccc(N3CCN(c4ccc(OC[C@@H]5CO[C@@](Cn6cnnn6)(c6ccc(Cl)cc6Cl)O5)cn4)CC3)c(F)c2)cnn1C1CCCCC1] | 111 |
| 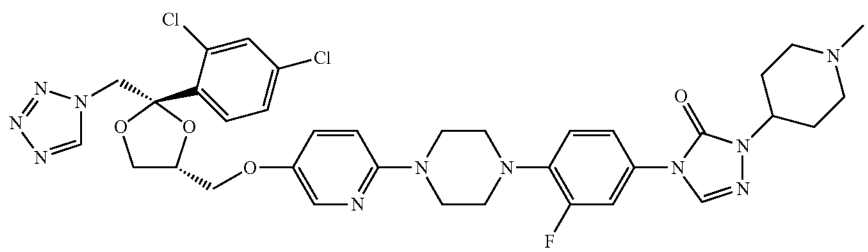 [SMILES: CN1CCC(n2ncn(-c3ccc(N4CCN(c5ccc(OC[C@@H]6CO[C@@](Cn7cnnn7)(c7ccc(Cl)cc7Cl)O6)cn5)CC4)c(F)c3)c2=O)CC1] | 112 |
| 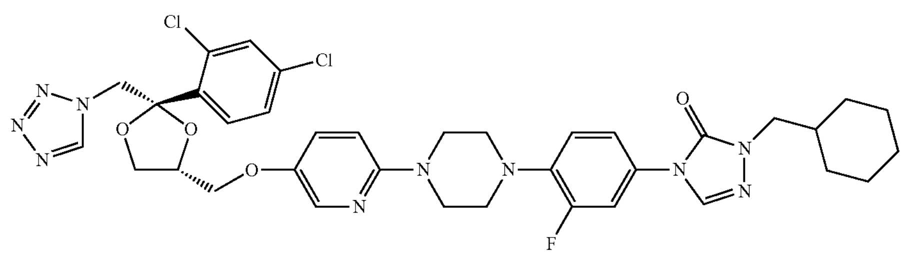 [SMILES: O=c1n(-c2ccc(N3CCN(c4ccc(OC[C@@H]5CO[C@@](Cn6cnnn6)(c6ccc(Cl)cc6Cl)O5)cn4)CC3)c(F)c2)cnn1CC1CCCCC1] | 113 |
| 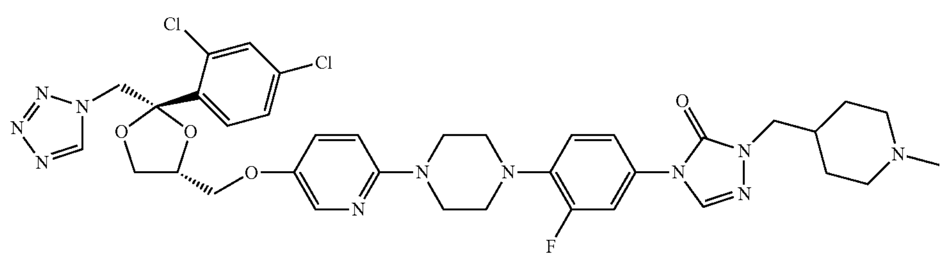 [SMILES: CN1CCC(Cn2ncn(-c3ccc(N4CCN(c5ccc(OC[C@@H]6CO[C@@](Cn7cnnn7)(c7ccc(Cl)cc7Cl)O6)cn5)CC4)c(F)c3)c2=O)CC1] | 114 |
| 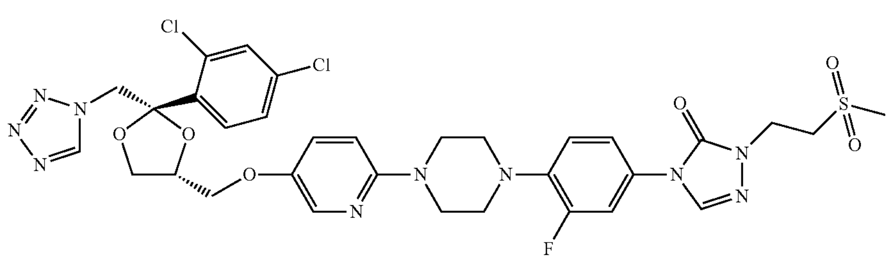 [SMILES: CS(=O)(=O)CCn1ncn(-c2ccc(N3CCN(c4ccc(OC[C@@H]5CO[C@@](Cn6cnnn6)(c6ccc(Cl)cc6Cl)O5)cn4)CC3)c(F)c2)c1=O] | 115 |

TABLE 1-continued
Summary of the compounds synthesized and tested in the present disclosure.
| Structure | Compound Number |
|---|---|
| 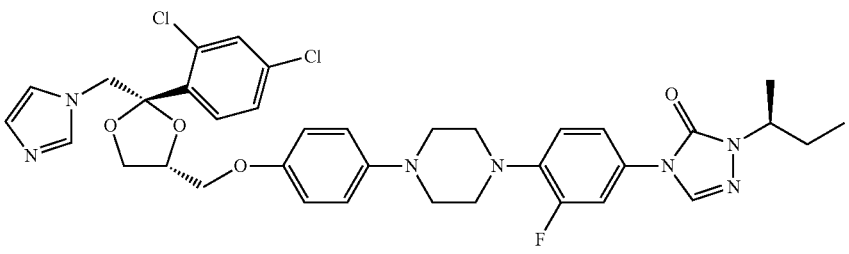 [SMILES: CC[C@H](C)n1ncn(-c2ccc(N3CCN(c4ccc(OC[C@@H]5CO[C@@](Cn6ccnc6)(c6ccc(Cl)cc6Cl)O5)cc4)CC3)c(F)c2)c1=O] | 116 |
| 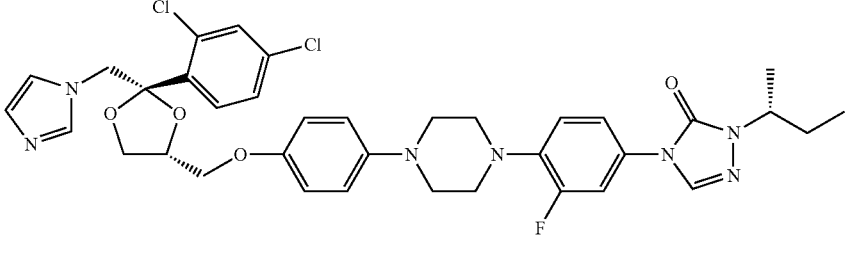 [SMILES: CC[C@@H](C)n1ncn(-c2ccc(N3CCN(c4ccc(OC[C@@H]5CO[C@@](Cn6ccnc6)(c6ccc(Cl)cc6Cl)O5)cc4)CC3)c(F)c2)c1=O] | 117 |
| 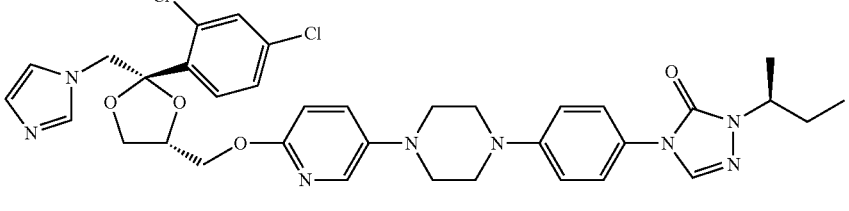 | 118 |
| 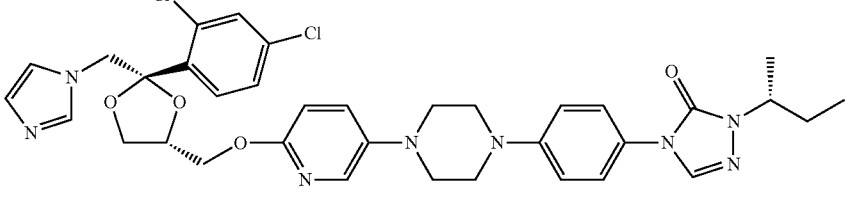 | 119 |
| 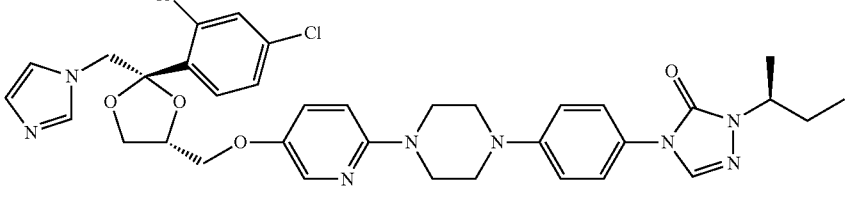 | 120 |
| 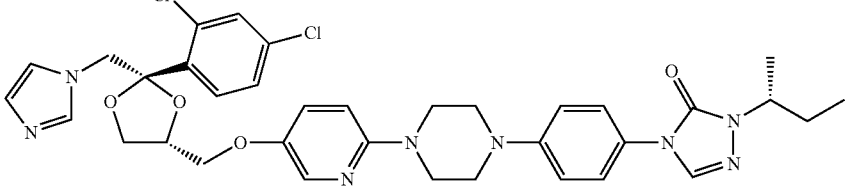 | 121 |

TABLE 1-continued

Summary of the compounds synthesized and tested in the present disclosure.

| Structure | Compound Number |
|---|---|
| 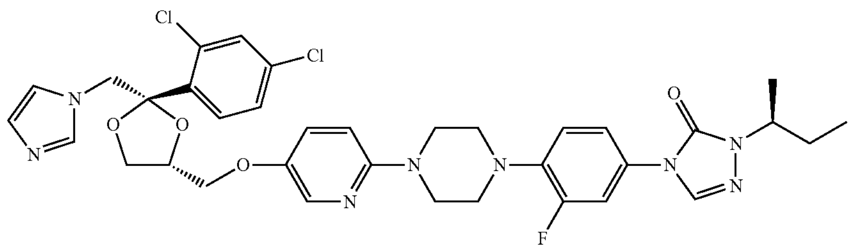 [SMILES: CC[C@H](C)n1ncn(-c2ccc(N3CCN(c4ccc(OC[C@@H]5CO[C@@](Cn6ccnc6)(c6ccc(Cl)cc6Cl)O5)cn4)CC3)c(F)c2)c1=O] | 122 |
| 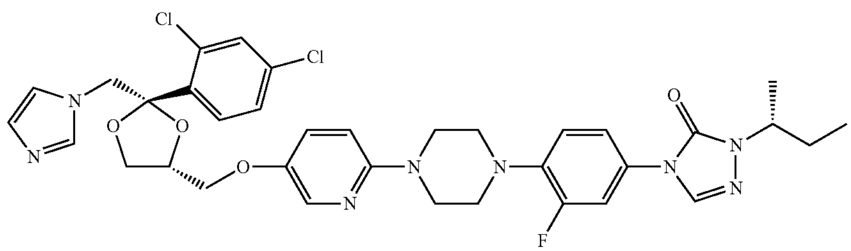 [SMILES: CC[C@@H](C)n1ncn(-c2ccc(N3CCN(c4ccc(OC[C@@H]5CO[C@@](Cn6ccnc6)(c6ccc(Cl)cc6Cl)O5)cn4)CC3)c(F)c2)c1=O] | 123 |
| 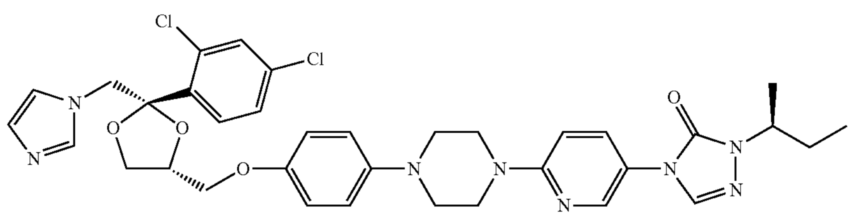 [SMILES: CC[C@H](C)n1ncn(-c2ccc(N3CCN(c4ccc(OC[C@@H]5CO[C@@](Cn6ccnc6)(c6ccc(Cl)cc6Cl)O5)cc4)CC3)nc2)c1=O] | 124 |
| 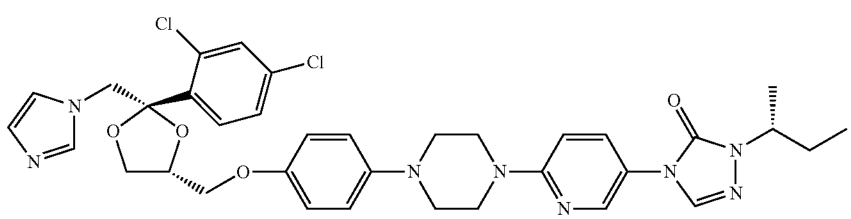 [SMILES: CC[C@@H](C)n1ncn(-c2ccc(N3CCN(c4ccc(OC[C@@H]5CO[C@@](Cn6ccnc6)(c6ccc(Cl)cc6Cl)O5)cc4)CC3)nc2)c1=O] | 125 |
| 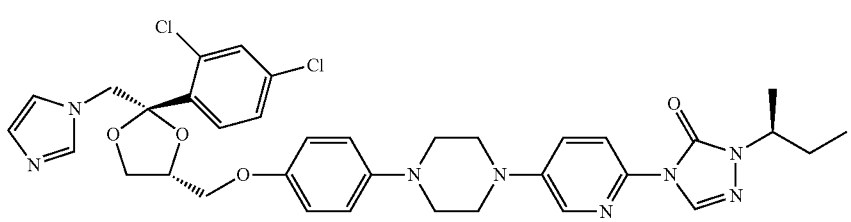 [SMILES: CC[C@H](C)n1ncn(-c2ccc(N3CCN(c4ccc(OC[C@@H]5CO[C@@](Cn6ccnc6)(c6ccc(Cl)cc6Cl)O5)cc4)CC3)cn2)c1=O] | 126 |
| 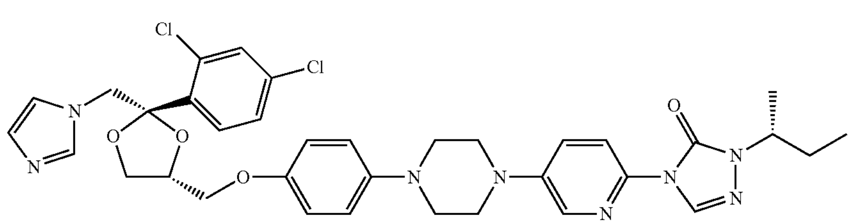 [SMILES: CC[C@@H](C)n1ncn(-c2ccc(N3CCN(c4ccc(OC[C@@H]5CO[C@@](Cn6ccnc6)(c6ccc(Cl)cc6Cl)O5)cc4)CC3)cn2)c1=O] | 127 |

TABLE 1-continued
Summary of the compounds synthesized and tested in the present disclosure.
| Structure | Compound Number |
|---|---|
| 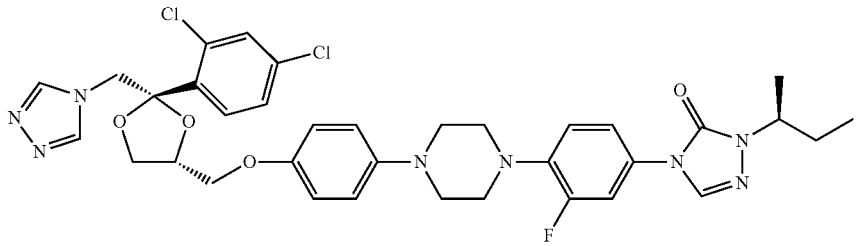 | 128 |
| 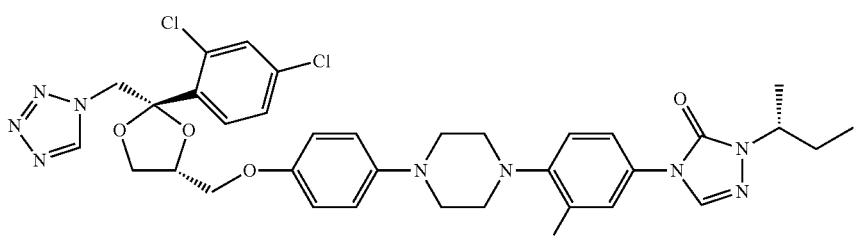 | 129 |
| 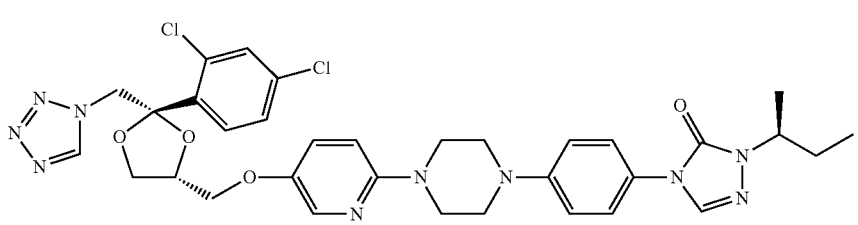 | 130 |
| 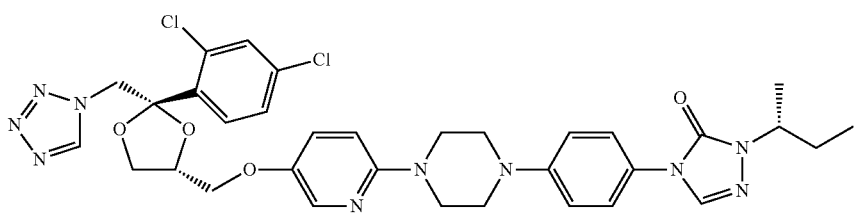 [SMILES: CC[C@@H](C)n1ncn(-c2ccc(N3CCN(c4ccc(OC[C@@H]5CO[C@@](Cn6cnnn6)(c6ccc(Cl)cc6Cl)O5)cn4)CC3)cc2)c1=O] | 131 |
| 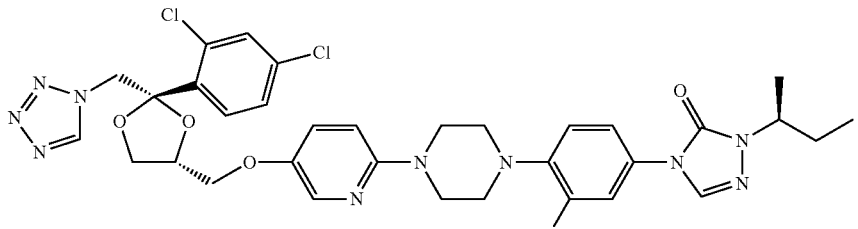 | 132 |
| 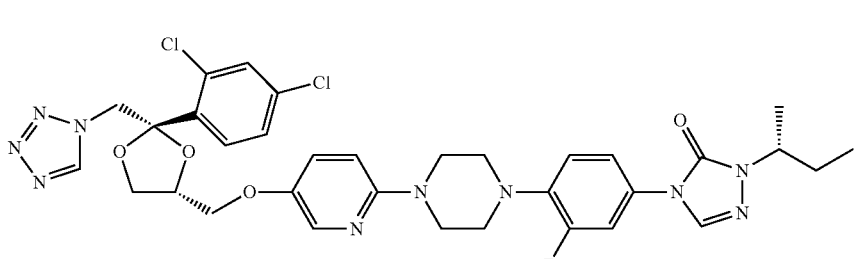 | 133 |

TABLE 1-continued

Summary of the compounds synthesized and tested in the present disclosure.

| Structure | Compound Number |
|---|---|
| 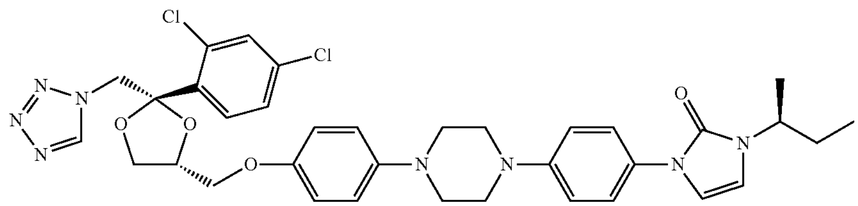 | 134 |
| 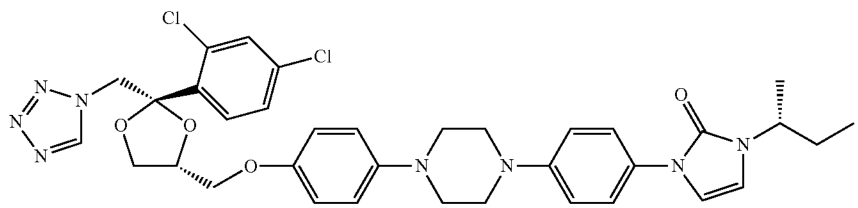 | 135 |
| 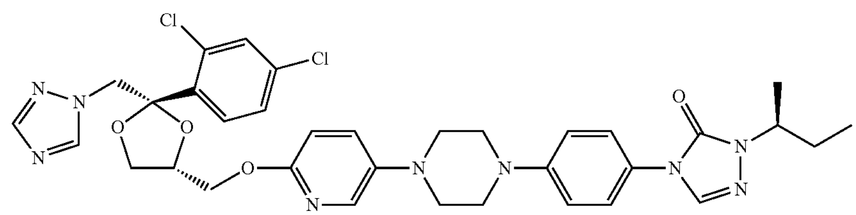 [SMILES: CC[C@H](C)n1ncn(-c2ccc(N3CCN(c4ccc(OC[C@@H]5CO[C@@](Cn6cncn6)(c6ccc(Cl)cc6Cl)O5)nc4)CC3)cc2)c1=O] | 136 |
| 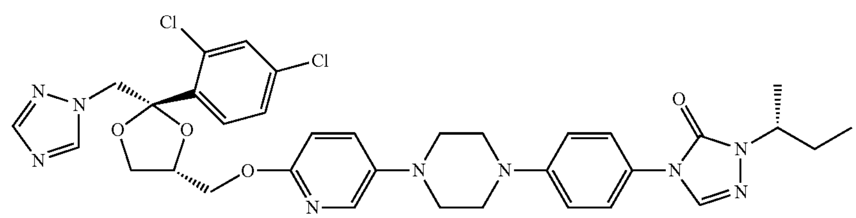 [SMILES: CC[C@@H](C)n1ncn(-c2ccc(N3CCN(c4ccc(OC[C@@H]5CO[C@@](Cn6cncn6)(c6ccc(Cl)cc6Cl)O5)nc4)CC3)cc2)c1=O] | 137 |
| 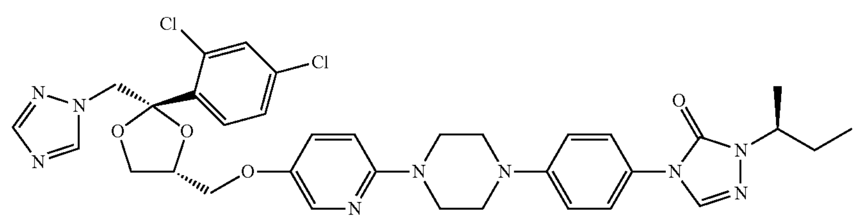 [SMILES: CC[C@H](C)n1ncn(-c2ccc(N3CCN(c4ccc(OC[C@@H]5CO[C@@](Cn6cncn6)(c6ccc(Cl)cc6Cl)O5)cn4)CC3)cc2)c1=O] | 138 |
| 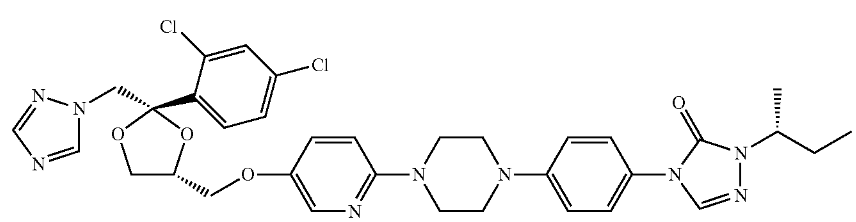 [SMILES: CC[C@@H](C)n1ncn(-c2ccc(N3CCN(c4ccc(OC[C@@H]5CO[C@@](Cn6cncn6)(c6ccc(Cl)cc6Cl)O5)cn4)CC3)cc2)c1=O] | 139 |
| 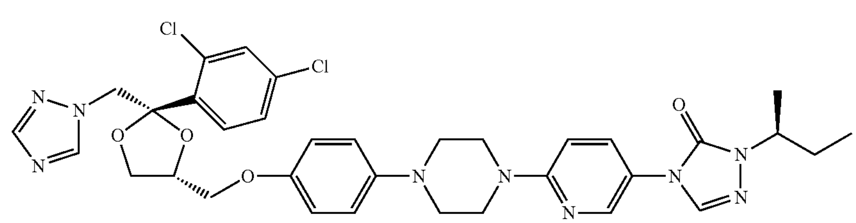 [SMILES: CC[C@H](C)n1ncn(-c2ccc(N3CCN(c4ccc(OC[C@@H]5CO[C@@](Cn6cncn6)(c6ccc(Cl)cc6Cl)O5)cc4)CC3)nc2)c1=O] | 140 |

TABLE 1-continued
Summary of the compounds synthesized and tested in the present disclosure.
| Structure | Compound Number |
|---|---|
| 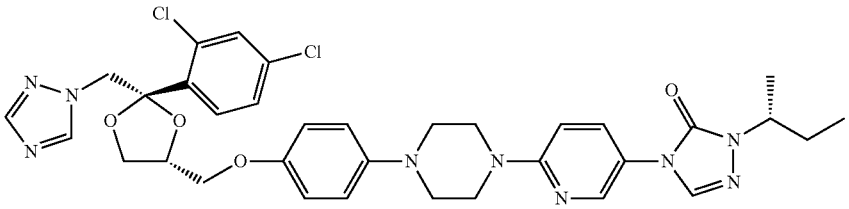 | 141 |
| 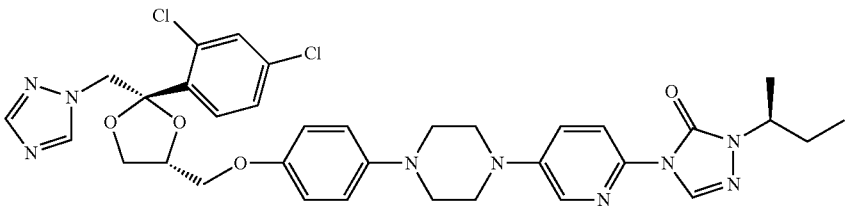 [SMILES: CC[C@H](C)n1ncn(-c2ccc(N3CCN(c4ccc(OC[C@@H]5CO[C@@](Cn6cncn6)(c6ccc(Cl)cc6Cl)O5)cc4)CC3)cn2)c1=O] | 142 |
| 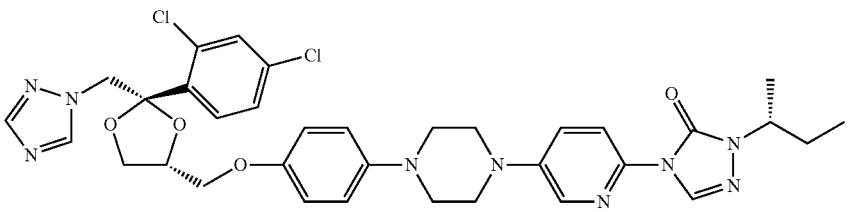 [SMILES: CC[C@@H](C)n1ncn(-c2ccc(N3CCN(c4ccc(OC[C@@H]5CO[C@@](Cn6cncn6)(c6ccc(Cl)cc6Cl)O5)cc4)CC3)cn2)c1=O] | 143 |
| 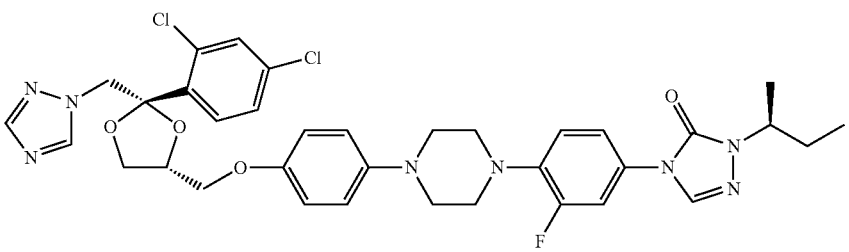 | 144 |
| 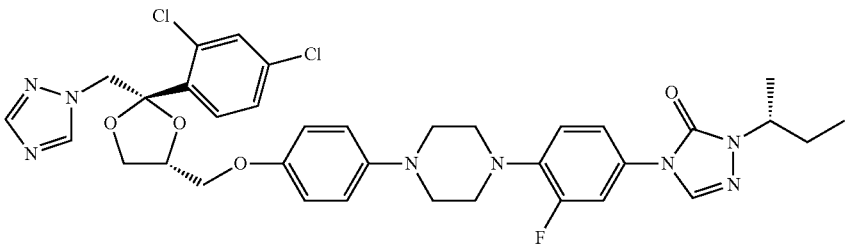 [SMILES: CC[C@@H](C)n1ncn(-c2ccc(N3CCN(c4ccc(OC[C@@H]5CO[C@@](Cn6cncn6)(c6ccc(Cl)cc6Cl)O5)cc4)CC3)c(F)c2)c1=O] | 145 |
| 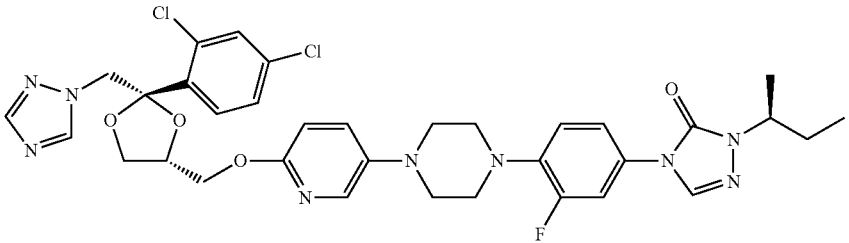 [SMILES: CC[C@H](C)n1ncn(-c2ccc(N3CCN(c4ccc(OC[C@@H]5CO[C@@](Cn6cncn6)(c6ccc(Cl)cc6Cl)O5)nc4)CC3)c(F)c2)c1=O] | 146 |

TABLE 1-continued

Summary of the compounds synthesized and tested in the present disclosure.

| Structure | Compound Number |
| --- | --- |
| [structure] | 147 |
| [structure] | 148 |
| [structure] | 149 |

TABLE 2

The HUVEC Anti-proliferation Activities and CYP3A4 Enzyme Inhibition of Intraconazole Analogs.

| Compound number | R | Proliferation $IC_{50}{}^a$ | Proliferation ($IC_{50}/IC_{50}$ Itra) | CYP3A4 Inhibition (compared to intracozanole at 1 um)[b] |
| --- | --- | --- | --- | --- |
| Intraconazole | | 0.17 | | |
| 62 | H | 0.328 | 1.9 | No inhibition |
| 59 | [ethyl] | 0.314 | 2.1 | No inhibition |
| 57 | [Br-substituted] | 0.569 | 3.0 | 0.03 |

TABLE 2-continued

The HUVEC Anti-proliferation Activities and CYP3A4 Enzyme Inhibition of Intraconazole Analogs.

| Compound number | R | Proliferation IC$_{50}$[a] | Proliferation (IC$_{50}$/IC$_{50}$ Itra) | CYP3A4 Inhibition (compared to intracozanole at 1 um)[b] |
|---|---|---|---|---|
| 61 | cyclopentylmethyl | 0.512 | 3.0 | No inhibition |
| 60 | benzyl | 0.513 | 3.0 | No inhibition |
| 64 | N,N-dimethylaminomethyl | 1.397 | 8.8 | No inhibition |
| 63 | morpholinomethyl | 1.175 | 7.4 | 0.20 |
| 66 | piperazinylmethyl | 0.608 | 2.5 | 1.09 |
| 65 | 4-methylpiperazinylmethyl | 0.396 | 3.8 | 0.21 |
| 50 | 3-methyl-1,2,4-triazol-1-ylmethyl | 0.272 | 1.6 | 0.36 |
| 47 | 3,5-dimethyl-1,2,4-triazol-1-ylmethyl | 0.221 | 1.3 | 0.32 |
| 51 | 3-trifluoromethyl-1,2,4-triazol-1-ylmethyl | 0.270 | 1.6 | No inhibition |
| 33 | imidazol-1-ylmethyl | 0.085 | 0.5 | 1.18 |

TABLE 2-continued
The HUVEC Anti-proliferation Activities and CYP3A4 Enzyme Inhibition of Intraconazole Analogs.
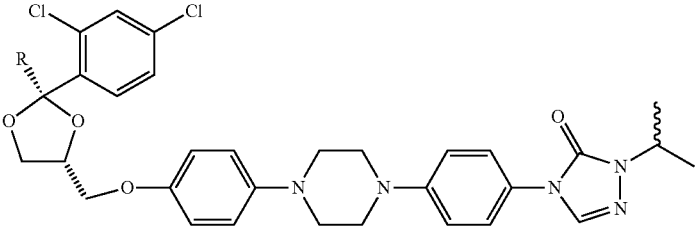
| Compound number | R | Proliferation IC$_{50}$$^a$ | Proliferation (IC$_{50}$/IC$_{50}$ Itra) | CYP3A4 Inhibition (compared to intracozanole at 1 um)$^b$ |
| --- | --- | --- | --- | --- |
| 35 | 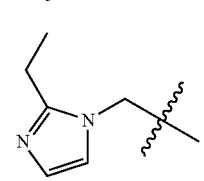 | 0.173 | 1.0 | 0.85 |
| 43 | 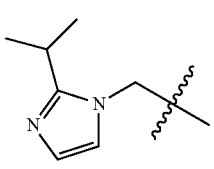 [SMILES: *Cn1ccnc1C(C)C] | 224.6 | 1.4 | 0.08 |
| 45 | 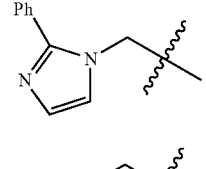 | 0.084 | 0.5 | 0.07 |
| 46 | Ph 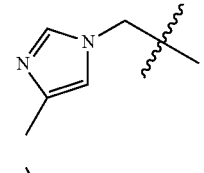 | 0.136 | 0.8 | 0.27 |
| 38 | 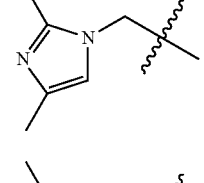 | 0.102 | 0.6 | 1.18 |
| 40 | 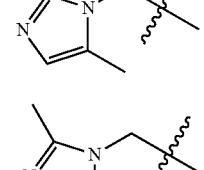 | 0.492 | 3.1 | 0.45 |
| 41 | 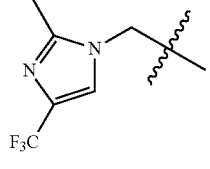 [SMILES: *Cn1cc(C(F)(F)F)nc1C] | 0.765 | 4.5 | 0.27 |
| 39 |  | 0.441 | 2.8 | No inhibition |

TABLE 2-continued

The HUVEC Anti-proliferation Activities and CYP3A4 Enzyme Inhibition of Intraconazole Analogs.

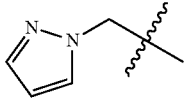 [SMILES: *Cn1cccn1]

| Compound number | R | Proliferation $IC_{50}{}^a$ | Proliferation ($IC_{50}/IC_{50}$ Itra) | CYP3A4 Inhibition (compared to intracozanole at 1 um)$^b$ |
|---|---|---|---|---|
| 34 | 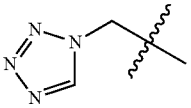 [SMILES: *Cn1cnnn1] | 0.307 | 1.8 | No inhibition |
| 48 | 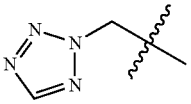 | 0.073 | 0.4 | 0.02 |
| 49 | 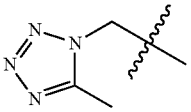 [SMILES: *Cn1nnnc1C] | 0.124 | 0.7 | 0.2 |
| 52 | 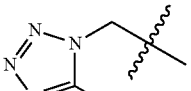 | 0.101 | 0.6 | 0.08 |
| 53 |  | 0.119 | 0.7 | 0.22 |

$^a$The $IC_{50}$ of HUVEC were evaluated using [$^3$H]-thymidine incorporation assay.
$^b$The CYP3A4 enzyme inhibition were evaluated using Vivid ® CYP3A4 green screening assay. values are indicated % enzyme inhibition at 1 uM drugs/% enzyme inhibition at 1 uM itraconazole. Values represent the mean of at least two separate experiments carried out in triplicate.

SAR studies of new itraconazole analogs using HUVEC proliferation and CYP3A4 enzymatic assays.

The anti-angiogenic activity of new itraconazole analogs was determined using a HUVEC proliferation assay with [3H]thymidine incorporation as a readout. And CYP3A4 inhibition was initially determined using a cell-free fluorescence-based assay at a final concentration of 1 µM (Table 2).

Figure 2:
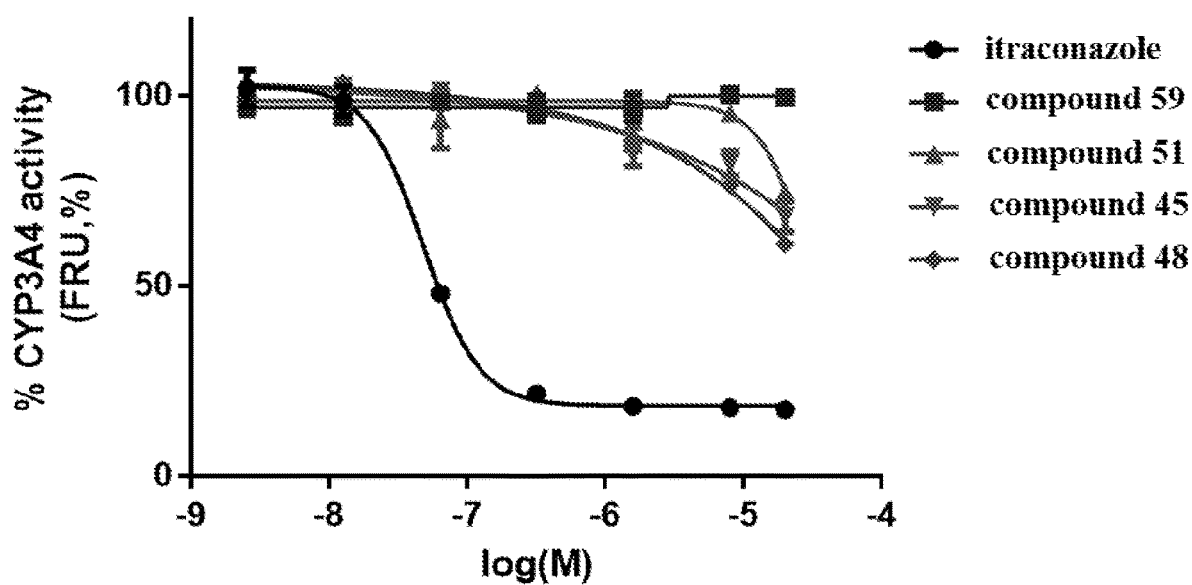
FIG. 2 shows the CYP3A4 enzyme activity in the presence of different concentrations of itraconazole, compounds 59, 51, 45, and 48.

To assess the importance of the triazole moiety for the anti-angiogenic activity of itraconazole and CYP3A4 inhibition, we removed the 1,2,4-triazole (compound 62), and replaced it with aliphatic ethyl (compound 59), bromo methyl (compound 57), cyclopentyl (compound 61) groups, or phenyl (compound 60) group. As expected, compounds 57 and 59-62 without nitrogen atom in R1 position exhibited no CYP3A4 inhibition at 1 µM in the initial screening. Further dose response assays showed that compound 59 totally lost CYP3A4 inhibition (FIG. 2). In contrast, the same group of analogs only suffered a 2-3 fold decrease in anti-proliferative activity against HUVEC, suggesting differential dependence of the two activities on the presence of the triazole moiety.

Next, a tertiary amine was introduced to the R1 position (compounds 63-66) with dimethylamine, morpholine, piperidyl or N-methyl piperidyl group, respectively. Analog compounds 63-66 have the added feature of having improved solubility compared with the parent itraconazole. The analogs containing aliphatic amine at R1 position inhibited CYP3A4 at 1 µM except for compound 64. Structurally, compounds 63, 65, and 66 have an electron donor nitrogen atom or oxygen atom at the position corresponding to N4 of 1,2,4-triazole in itraconazole. The results suggested that the aliphatic nitrogen and oxygen are also capable of interacting with the heme group in CYP3A4. Compared to itraconazole, compounds 63-66 had 2-9 fold decrease in antiproliferative activity in HUVEC. Together, the results confirmed that CYP3A4 inhibition of itraconazole is highly dependently on 1,2,4-triazole, especially the basic N4 atom of triazole. They also suggested that replacing the triazole moiety with either alkyl or aliphatic amines is not sufficient to decrease CYP3A4 inhibition without compromising the antiangiogenic activity.

Given the importance of the triazole moiety in the anti-angiogenic activity of itraconazole, we decided to make less drastic structural alterations of the triazole by increasing the steric hindrance around the nitrogen atom at 4 position that might decrease its access to the heme iron in CYP3A4. As a start, we introduced methyl or trifluoromethyl substitution to 1,2,4-triazole. Analog compound 50 with 3-methyl-1H-1,2,4-triazole substitution and compound 51 with di-methyl substitution showed reduced potency in CYP3A4 inhibition. The trifluoromethyl substitution compound 47 showed no CYP3A4 inhibition at 1 µM and weak inhibition at higher concentration (FIG. 2). The IC50 values of compounds 50, 47, and 51 for inhibition of HUVEC proliferation were 0.27, 0.22, and 0.27 respectively, slightly higher than that of itraconazole (0.17 Compound 33 contains an imidazole moiety in place of 1,2,4-triazole and exhibited higher potency against HUVEC proliferation than itraconazole. We synthesized a series of analogs containing imidazole group with various substitutions (compounds 35, 43, 45, and 46). Similar to compound 51, compound 39 with 2-methyl-4-trifluoromethyl-1H-imidazol-yl moiety has both steric hindrance and electron withdrawing effects, and furthermore the N3 nitrogen is no longer reactive to heme, so the CYP3A4 inhibition is eliminated at 1 µM. However the dual substituted compounds (compounds 39-41) also suffered a 2-3 fold decrease in anti-angiogenic activity. Interestingly, among the single substituted imidazol-yl compounds, the 2-isopropyl-1H-imidazol-yl analog compound 45 had the most potent HUVEC inhibition activity, with an IC50 of 0.084 µM. Compounds with substituents smaller or larger than the isopropyl group were all less potent than compound 45. On the other hand, CYP3A4 inhibition showed a different trend—the larger the substituents on the imidazole, the less inhibition of CYP3A4.

In contrast to triazole and imidazole which are basic aromatic rings, the tetrazole is relatively acidic due to addition of another nitrogen to the 5-membered ring. Because coordination of the basic nitrogen to heme iron is required for the inhibitory activity of itraconazole against CYP3A4, we reasoned that the tetrazole compound should have reduced CYP3A4 inhibition compared to imidazole or tetrazole compounds. We synthesized a 1-tetrazole-yl analog compound 48; it showed improved anti-proliferative activity in HUVEC with an IC50 of 0.073 µM and significantly reduced CYP3A4 inhibition with an IC50 above 20 µM (FIG. 2). In contrast, the structurally related 2-tetrazole-yl analog compound 49 is less potent in HUVEC and exhibited greater CYP3A4 inhibition than compound 48. Addition of a 5-methyl or 5-phenyl substituents to the tetrazole group did not lead to further improvement over analog compound 48, rendering compound 48 one of the most optimal among all itraconazole analogs. Thus, we selected compound 48 for further biological evaluation.

Figure 3:
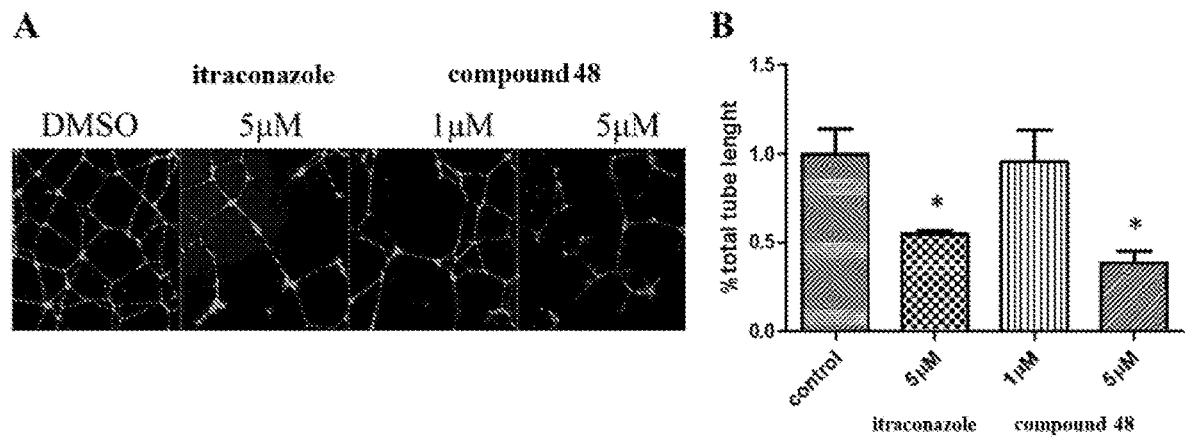
FIGS. 3A-3B illustrate compound 48 inhibits HUVEC tube formation. HUVECs were planted on Matrigel and treated with 5 μM itraconazole, 1 μM compound 48, 5 μM compound 48 or DMSO for 20 h. (A) Cells were then stained with Calcein-AM and vascular networks were imaged using fluorescent microscope. (B) total tube lengths from the fluorescence images were quantified using the imageJ software and plotted using GraphPad Prism. Data, mean±SE of three independent experiments. (* p<0.01)

Inhibition of Tube Formation. To further assess the anti-angiogenic activity of compound 48, we employed an in vitro tube formation assay. In the tube formation assay, HUVECs are seeded on matrigel, cells migrate and elongate to form tubule-like networks after 20 hours, which is reminiscent of new blood vessel formation. As shown in FIG. 3, treatment of HUVEC with 5 µM itrconazole inhibited 45% of HUVEC tube formation as judged by the total tube length. At the same concentration, compound 48 inhibited 61% of HUVEC tube formation, which further confirmed that compound 48 is a more potent anti-angiogensis inhibitor.

Figure 4:
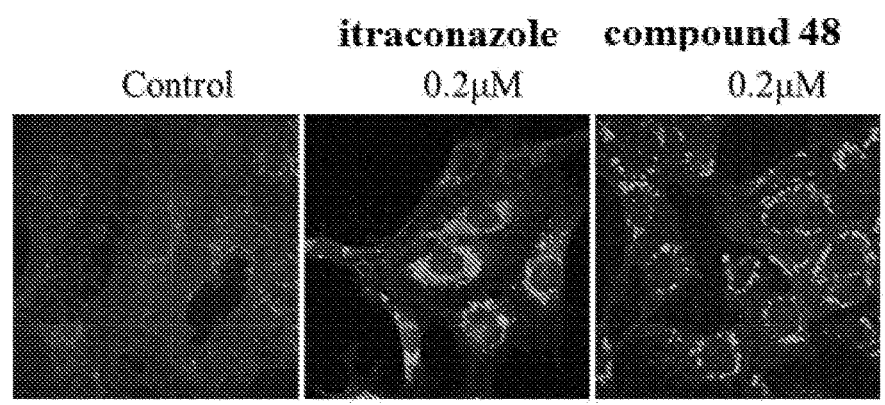
FIG. 4 shows itraconazole and compound 48 induce NPC phenotype at 0.2 μM. HUVECs were treated with 0.2 μM itraconazole, 0.2 μM compound 48 or DMSO for 24 h. Intracellular cholesterol was visualized using filipin staining and fluorescent images were captured under a confocal microscope.
Figure 5:
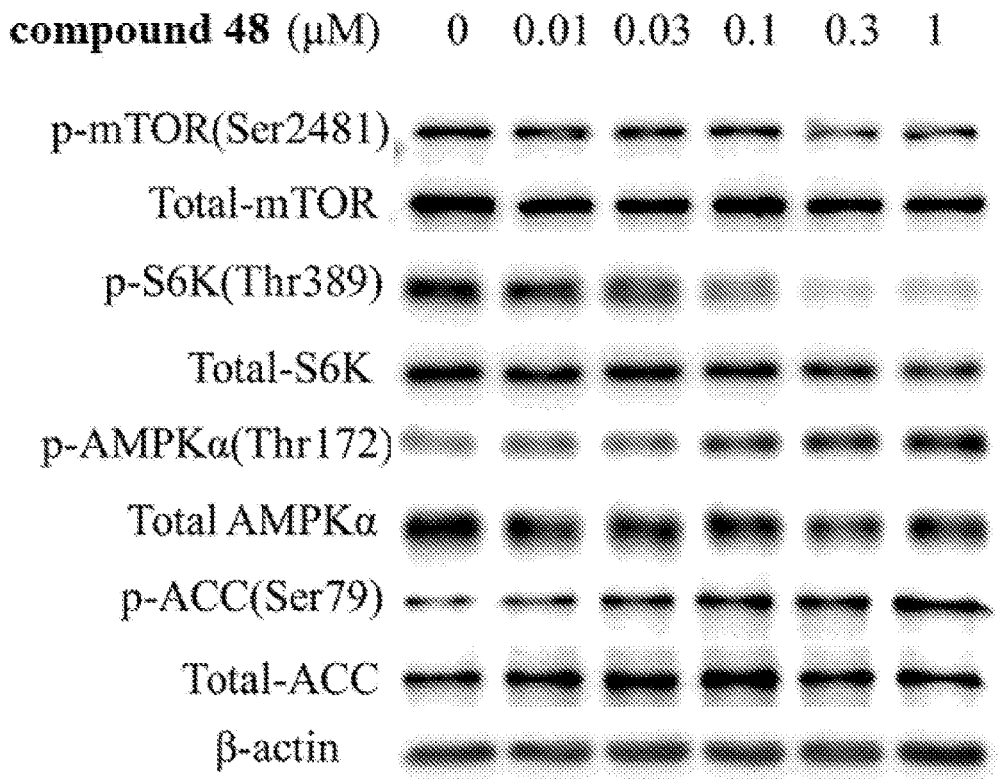
FIG. 5 shows compound 48 dose-dependently activates AMPK and inhibits mTOR in HUVECs. HUVECs were treated with 0.01 μM, 0.03 μM, 0.1 μM, 0.3 μM, 1 μM of compound 48 or DMSO for 24 h. Cell lysates were subjected to Western blot.

Nieman-Pick C phenotype and mTOR inhibition. We have previously shown that the mechanism underlying the anti-angiogenic activity of itraconazole is mediated in part through inhibition of endolysosomal cholesterol trafficking and mTOR inhibition. We thus determined whether compound 48 shared the same mechanism with itraconazole. The intracellular cholesterol was detected using the cholesterol-binding fluorescent dye filipin. As shown in FIG. 4, similar to itraconazole, compound 48 induced NPC phenotype at a concentration of 0.2 µM as judged by the accumulation of cholesterol in the late endosome/lysosome. Analog compound 48 also increased the phosphorylation of AMPK☐ at Thr172 in a dose-dependent manner (FIG. 5). The phosphorylation of AMPK☐ substrate acetyl CoA carboxylase 1 (ACC1) was also increased as expected. It is known that AMPK activation leads to mTOR inhibition. Treatment of HUVEC with compound 48 indeed led to a decrease in the phosphorylation of mTOR and the phosphorylation of its downstream effector p70 S6 Kinase (S6K). Together, these results suggested that compound 48 inhibited HUVEC proliferation and angiogenesis with the same targets and underlying mechanism as itraconazole.

The inhibition of CYP3A4 limits the use of itraconazole as an anticancer agent due to metabolic interactions with other anticancer drugs. To overcome this limitation, we have synthesized a series of azole and non-azole derivatives of itraconazole and evaluated their anti-angiogenic activities and CYP3A4 inhibition. Based on our SAR study, we conclude that the CYP3A4 inhibition by itraconazole is highly dependent on the coordination of 1,2,4-triazole to the heme iron, and that modification of triazole could reduce or eliminate CYP3A4 inhibition. The non-azole analogs successfully eliminated the CYP3A4 inhibition by disrupting the binding to the heme, but unfortunately, the compounds were significantly less potent against HUVEC than itraconazole. Substituted azoles with steric hindrance and electron withdrawing groups also eliminated CYP3A4 inhibition as seen in analog compounds 51 and 39. The 1H-tetrazol-yl analog compound 48 showed an EC50 of above 20 µM against CYP3A4. More importantly, it also exhibited more potent anti-angiogenic activity than itraconazole. The angiogenic potency of compound 48 was further confirmed by HUVEC tube formation. Like itraconazole, compound 48 functions by the same mechanism as itraconazole by NPC1 phenotype induction and mTOR inhibition. Together, our results strongly suggest that the tetrazole-containing analog compound 48 is a promising new lead for the development of the next generation itraconazole analog with improved anti-angiogenic potency and little CYP3A4 inhibition that can be used in combination with most other known anticancer drugs for the treatment of a wide variety of cancers.

Scheme 1. Synthetic procedure for compounds 57-62.

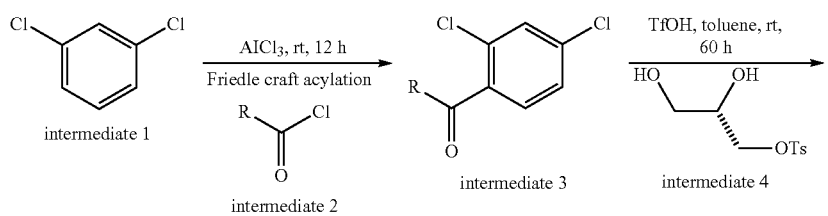

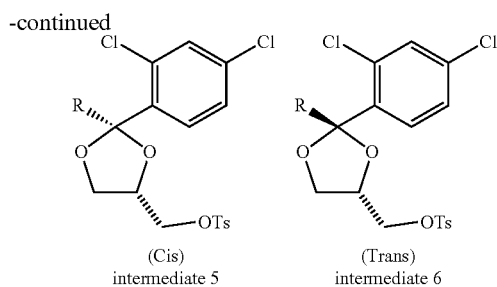

(Cis) intermediate 5

(Trans) intermediate 6

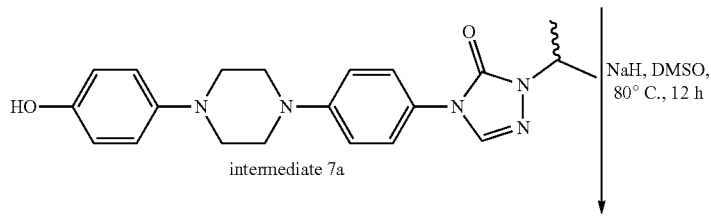

intermediate 7a

NaH, DMSO, 80° C., 12 h

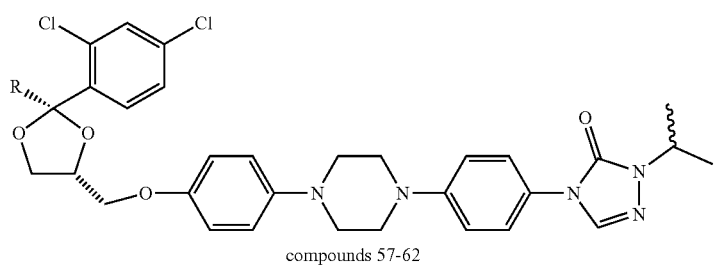

compounds 57-62

The synthetic route for the non-azole itraconazole analogues (compounds 57-62) is outlined in Scheme 1. The synthesis commenced with the commercially available 1,3-dichlorobenzene and a series of different acid chlorides. Intermediates 3 (a-f), 5 (a-f), and 6 (a-f) can be different depending on the structure of the products. Intermediates The intermediate 2, 4-dichloro benzaldehyde (intermediate 3a) is commercially available. The other intermediates intermediates 3b-3f were efficiently prepared by the acylation of 1, 3-dichlorobenzene with series of acid chlorides (intermediates 2b-2f) under Friedel-Craft acylation conditions in satisfactory yields (70%-90%). Our previous results suggested that 2S,4R-cis-stereochemistry on the 1, 3-dioxalane ring is more potent for anti-angiogenic activity than alternative stereochemical configurations. We thus constructed the cis-1,3-dioxolane (intermediates 5a-5f) via acid-assisted ketalization of 2, 4-dichloro acetophenones (intermediates 3a-3f) with optically pure glyceryl tosylate in the presence of methanesulfonic acid (TfOH) in toluene, yielding cis and trans diastereomers in the ratio of 3:1 with good yields. Those two diastereomers were easily separated by column chromatography. The acquired phenol fragment 105a was synthesized followed by the previously reported synthetic routes. See U.S. Pat. No. 9,346,791. The phenol fragment intermediate 7a was subjected to the 0-tosylates in the presence of NaH to afford final products (compounds 57-62). Analogs with tertiary amine group (compounds 63-66) were prepared from a nucleophilic substitution reaction of bromo substituted compound 57 and different secondary amines (Scheme 2).

Scheme 2. Synthetic procedure for compounds 63-66.

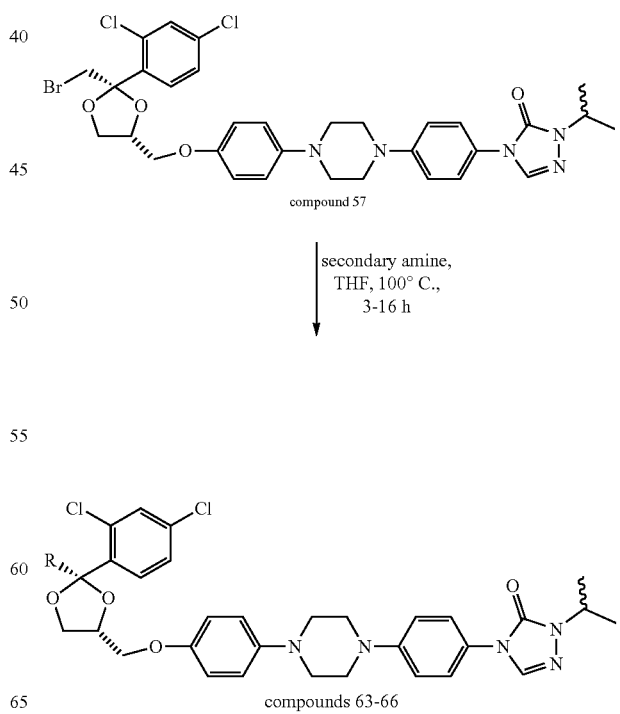

compound 57 secondary amine, THF, 100° C., 3-16 h compounds 63-66

Scheme 3. Synthetic procedure for compounds 1-23, 33-53, and 67-90.

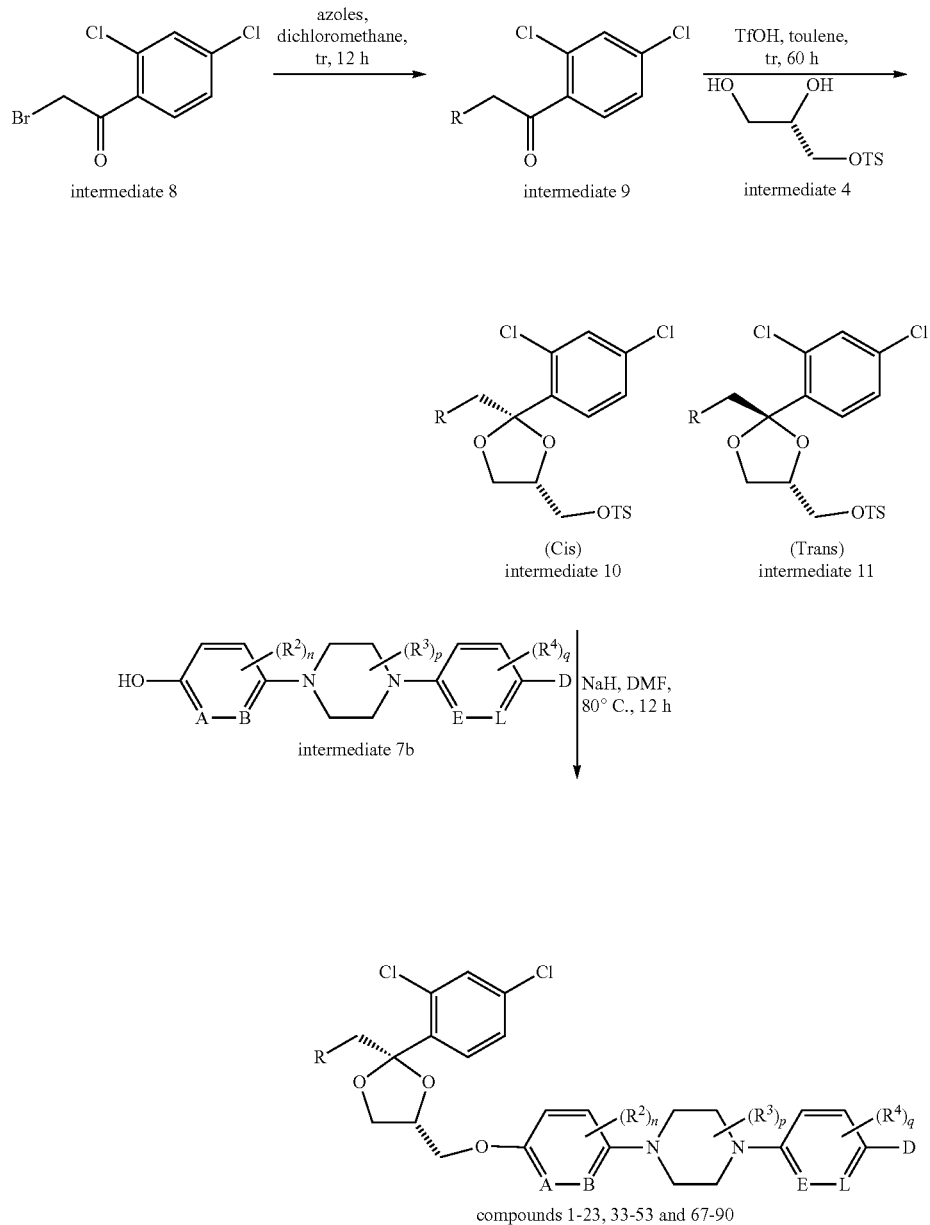

The synthetic route to substituted azole-containing itraconazole analogues (compounds 1-23, 33-53, and 67-90) is outlined in Scheme 3. Intermediates 9, 10, and 11 can be different depending on the structure of the products. Itraconazole analogues were synthesized using a similar route as outlined in Scheme 1. The intermediates (9) were prepared by N-alkylation of 2-bromo-1-(2,4-dichlorophenyl) ethanone (intermediate 8) with a series of azoles in DCM at room temperature. Ketalization of ethanones intermediate 9 with glyceryl tosylate (intermediate 4) gave intermediates as a cis diastereoisomer intermediate 10 with low to moderate yields (10%-65%). Finally, 0-tosylate intermediates 108 treated with fragment intermediate 7b to get the desired products. The synthesis of compounds 24-32, 54-56, and 91-98 can be found in U.S. Pat. No. 9,346,791.

Despite its potential as a novel anti-angiogenic drug, itraconazole has three major limitations. First, the inhibition of Cytochrome P450 3A4 (CYP3A4) prevents combination therapy of itraconazole with the majority of other anticancer drugs. Second, the high lipophilicity of itraconazole (log P=5.3) results in its accumulation in adipose tissues, with concentrations in skin and fat tissues of 19-fold and 17-fold greater than that in the plasma, respectively. Third, itraconazole is relatively insoluble in water and has limited oral bioavailability. Although a clinically-used suspension formulation is able to improve its bioavailability, itraconazole has a highly variable absorption and the plasma concentration is often difficult to predict from individual to individual. The high lipophilicity and the low solubility of itraconazole, though tolerable for the treatment of fungal infections, pose major problems in the treatment of cancer.

Scheme 4. Structures of Itraconazole, IT-C (compound 99), and compound 24.

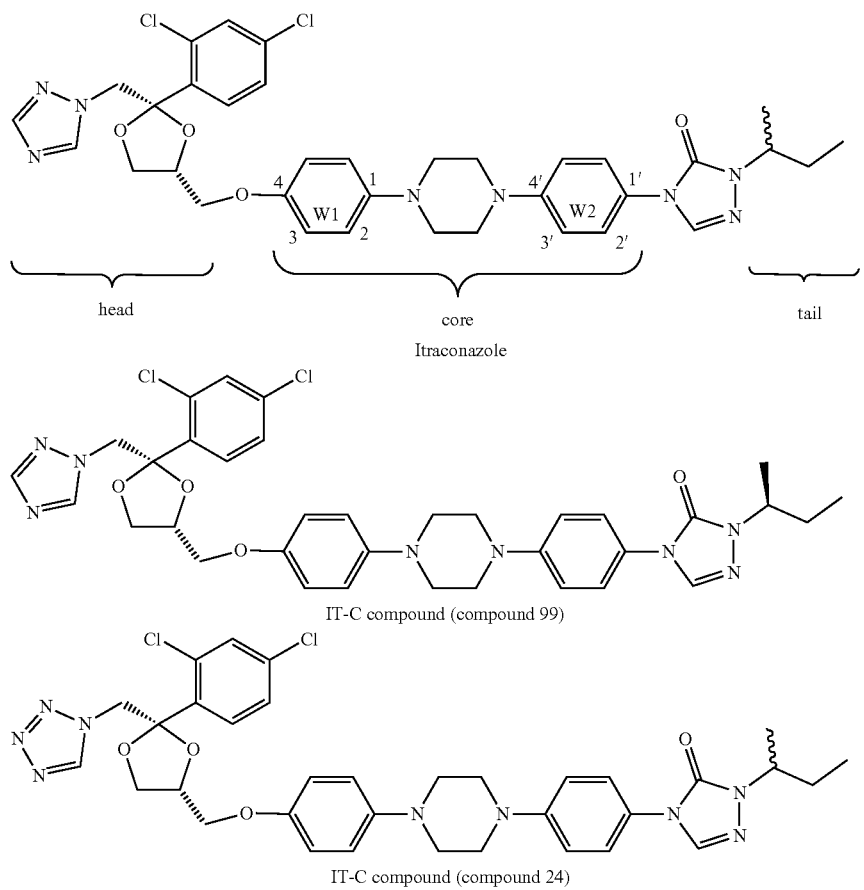

Itraconazole

IT-C compound (compound 99)

IT-C compound (compound 24)

In an attempts to improve the potency and reduce the toxicity of itraconazole, systematic structure and activity relationship (SAR) studies were conducted on the two ends of itraconazole. Compound IT-C (compound 99) with cis-(2S,4R,2'S) stereochemistry in the dioxolane ring, wherein the isobutyl sidechain with a 2'S configuration, showed the strongest anti-angiogenic activity among the 8 stereoisomers of itraconazole and significantly reduced hepatotoxicity. Compound 24 with tetrazole in place of the 1,2,4-triazole in the head position had increased activity and significantly reduced CYP3A4 inhibition while a methyl substitution in the same position resulted in the loss of anti-angiogenic activity. Moreover, the sec-butyl tail (or similar alkyl group) was required for angiogenesis inhibition.

Although modifications at the "head" and "tail" sections of itraconazole have effectively reduced the CYP3A4 inhibition and hepatotoxicity, the hydrophobicity and accompanying low water solubility remains to be resolved. The hydrophobicity of itraconazole can be attributed in large part to the two phenyl groups in the "core" region of the molecule (W1-piperizin-1-yl-W2, Scheme 4). The phenyl-piperizin-1-yl-phenyl core portion has a symmetrical and rigid configuration. It was reported that symmetrical and rigid compounds have high crystal packing energies, and therefore have low solubility in water as well as in organic solvents. In an effort to further improve the properties of Itraconazole analog compounds, we used pyridyl to replace phenyl group or adding a fluorine substitution on the phenyl ring. The synthesis and anti-angiogenic activity characterization of the novel analogs are discussed in the following.

Scheme 5. Synthetic procedure for additional compounds in the present disclosure.

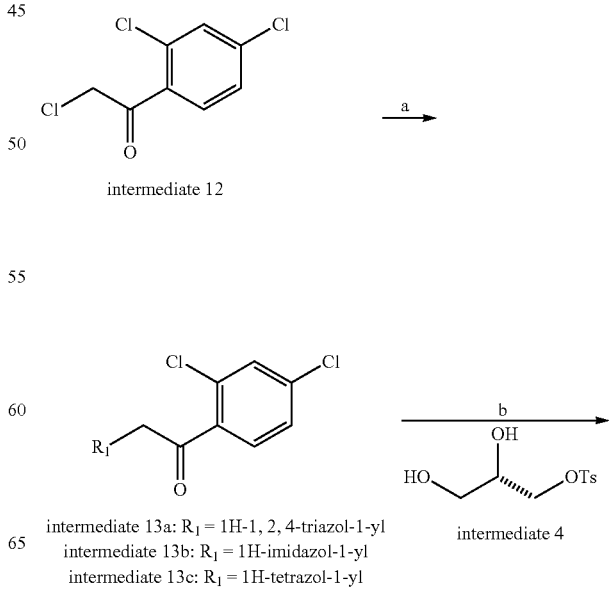

intermediate 12 intermediate 13a: $R_1$ = 1H-1, 2, 4-triazol-1-yl
intermediate 13b: $R_1$ = 1H-imidazol-1-yl
intermediate 13c: $R_1$ = 1H-tetrazol-1-yl intermediate 4

-continued

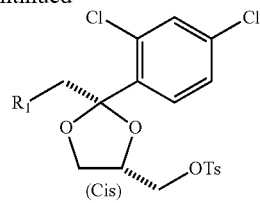

intermediate 14a: R₁ = 1H-1, 2, 4-triazol-1-yl
intermediate 14b: R₁ = 1H-imidazol-1-yl
intermediate 14c: R₁ = 1H-tetrazol-1-yl

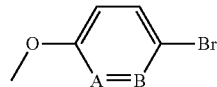

intermediate 15a:
A = OH, B = OH
intermediate 15b:
A = N, B = OH
intermediate 15c:
A = OH, B = N

+

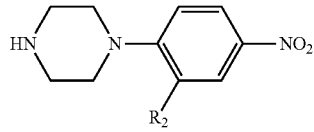

intermediate 16a:
R₂ = H
intermediate 16b:
R₂ = F

→ c

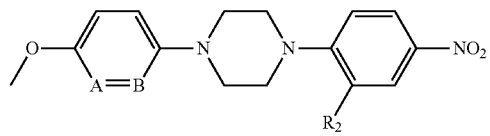

intermediate 17a:
A = N, B = OH, R₂ = H
intermediate 17b:
A = OH, B = N, R₂ = H
intermediate 17c:
A = OH, B = OH, R₂ = F
intermediate 17d:
A = N, B = OH, R₂ = F
intermediate 17e:
A = OH, B = N, R₂ = F → d

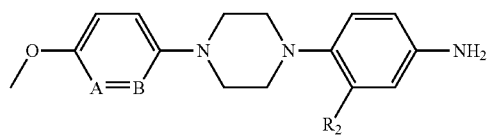

intermediate 18a:
A = N, B = OH, R₂ = H
intermediate 18b:
A = OH, B = N, R₂ = H
intermediate 18c:
A = OH, B = OH, R₂ = F
intermediate 18d:
A = N, B = OH, R₂ = F
intermediate 18e:
A = OH, B = N, R₂ = F → e -continued

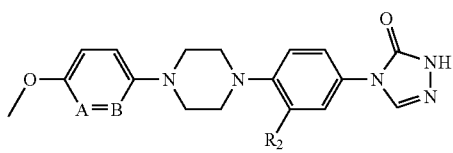

intermediate 19a:
A = N, B = OH, R₂ = H
intermediate 19b:
A = OH, B = N, R₂ = H
intermediate 19c:
A = OH, B = OH, R₂ = F
intermediate 19d:
A = N, B = OH, R₂ = F
intermediate 19e:
A = OH, B = N, R₂ = F → f

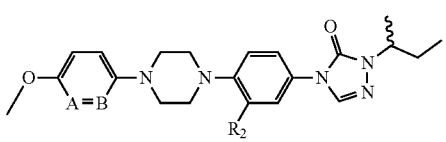

intermediate 20a:
A = N, B = OH, R₂ = H
intermediate 20b:
A = OH, B = N, R₂ = H
intermediate 20c:
A = OH, B = OH, R₂ = F
intermediate 20d:
A = N, B = OH, R₂ = F
intermediate 20e:
A = OH, B = N, R₂ = F → g

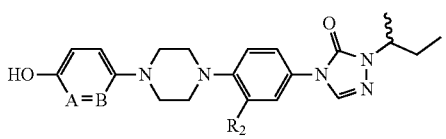

intermediate 21a:
A = N, B = OH, R₂ = H
intermediate 21b:
A = OH, B = N, R₂ = H
intermediate 21c:
A = OH, B = OH, R₂ = F
intermediate 21d:
A = N, B = OH, R₂ = F
intermediate 21e:
A = OH, B = N, R₂ = F → h

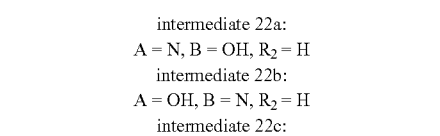

intermediate 22a:
A = N, B = OH, R₂ = H
intermediate 22b:
A = OH, B = N, R₂ = H
intermediate 22c:
A = OH, B = OH, R₂ = F
intermediate 22d:
A = N, B = OH, R₂ = F
intermediate 22e:
A = OH, B = N, R₂ = F → i -continued

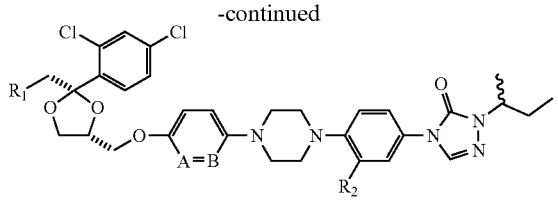

compound 100: $R_1$ = 1H-1,2,4-triazole-1-yl, A = N, B = OH, $R_2$ = H
compound 101: $R_1$ = 1H-1,2,4-triazole-1-yl, A = OH, B = N, $R_2$ = H
compound 104: $R_1$ = 1H-1,2,4-triazole-1-yl, A = OH, B = OH, $R_2$ = F
compound 105: $R_1$ = 1H-1,2,4-triazole-1-yl, A = N, B = OH, $R_2$ = F
compound 106: $R_1$ = 1H-1,2,4-triazole-1-yl, A = OH, B = N, $R_2$ = F
compound 2: $R_1$ = 1H-imidazol-1-yl, A = N, B = OH, $R_2$ = H
compound 4: $R_1$ = 1H-imidazol-1-yl, A = OH, B = N, $R_2$ = H
compound 1: $R_1$ = 1H-imidazol-1-yl, A = OH, B = OH, $R_2$ = F
compound 5: $R_1$ = 1H-imidazol-1-yl, A=OH, B= N, $R_2$ = F
compound 14: $R_1$ = 1H-tetrazol-1-yl, A = OH, B = N, $R_2$ = H
compound 8: $R_1$ = 1H-tetrazol-1-yl, A = OH, B = OH, $R_2$ = F
compound 15: $R_1$ = 1H-tetrazol-1-yl, A = OH, B = N, $R_2$ = F Reagents and conditions: (a) azoles, $K_2CO_3$, CAN, rt, 16 h, 40-70%; (b) TfOH, toluene, rt, 60 h, 55%; (c) $Pd_2(dba)_3$, BINAP, NaOtBu, toluene, 80° C., 16 h, 80%; (d) 10% Pd/C, $N_2H_4•H_2O$, EtOH, reflux, 3.5 h, quantitative (e) Phenyl chloroformate, pyridine, rt, 16 h, 82%; (f) i. $NH_2NH_2•H_2O$, 1,4-dioxane, reflux, 3 h; ii. formamidine acetate, 1-propanol, reflux, 3 h, 66%; (g) 2-bromobutane, $K_2CO_3$, DMSO, 80° C., 16 h, 82%; (h) 48% aqueous HBr, 110° C., 87%; (i) NaH, DMF, 80° C., 16 h, 60-75%.

diastereomer intermediate 14 were separated with normal phase column chromatography. The other part of the analogs was synthesized in two different routes dictated by the commercial accessibility of the starting material.

For analogs in which the W1 group was a pyridyl, Buchwald-Hartwig cross coupling of bromides intermediate 15 with intermediate 16 were used to generate nitrobenzene intermediate 17. Then the nitro group was reduced to an amine with 10% Pd/C and hydrazine monohydrate in ethanol. The triazolone ring was built in three steps by reacting the aniline intermediates with phenyl chloroformate, hydrazine monohydrate, and formamidine acetate, successively. N-alkylation of triazolone intermediate 20 with 2-bromobutane under basic conditions afforded the intermediates intermediate 21. The methyl protecting group in intermediate 21 was unmasked with 48% aqueous hydrobromic acid (HBr) at 110° C. The resulting phenol intermediate 22 was coupled with tosylate intermediate 14 to give the desired compounds 1, 2, 4, 5, 8, 14, 15, 100, 101, 104, 105, and 106.

For analogs in which the W1 ring was phenyl and W2 was pyridyl, the nitro intermediates 25 were constructed via C—N cross coupling reaction of 2-bromo-5-nitropyridine

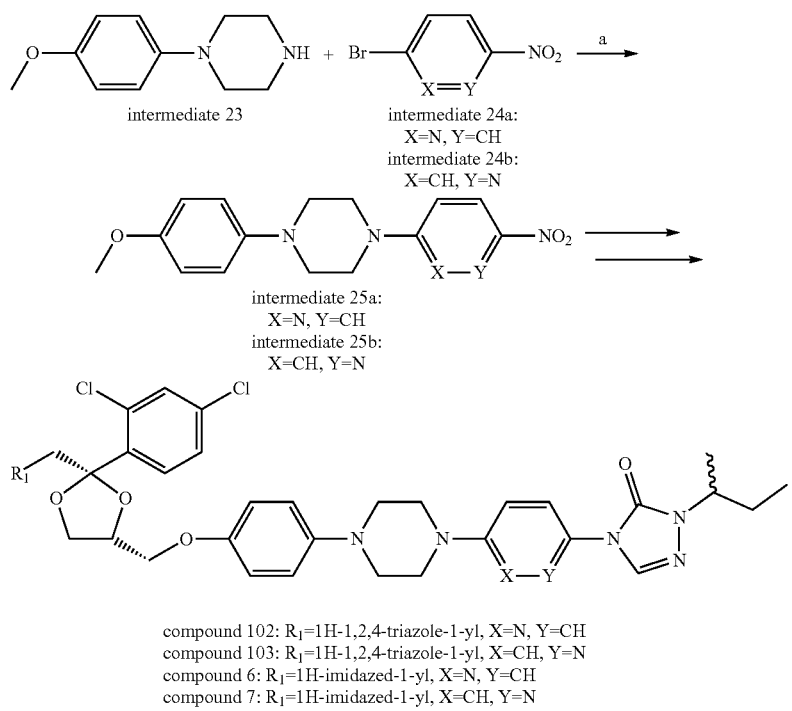

Scheme 6. Synthetic procedure for compounds 6, 7, 102, and 103.

compound 102: $R_1$=1H-1,2,4-triazole-1-yl, X=N, Y=CH
compound 103: $R_1$=1H-1,2,4-triazole-1-yl, X=CH, Y=N
compound 6: $R_1$=1H-imidazed-1-yl, X=N, Y=CH
compound 7: $R_1$=1H-imidazed-1-yl, X=CH, Y=N The syntheses of additional novel itraconazole analogs were accomplished using modified synthetic routes shown in Schemes 5 and 6. Nucleophilic displacement of the chlorine in intermediate 12 with 1,2,4-triazole, imidazole or tetrazole, followed by ketalization ring-closure reaction with enantiomerically pure glyceryl tosylate intermediate 4 under strong acid conditions, provided 1,3-dioxolane intermediate as a cis- and trans-mixture in a ratio of 3:1. The cis-2S,4R (intermediate 24a) or 5-bromo-2-nitropyridine (intermediate 24b) with piperizine intermediate 23 using Pd2(dba)3 as a catalyst, 2,2'-bis(diphenylphosphino)-1,1'-binaphthyl (BINAP) as a ligand and sodium tert-butoxide as a base. The resulting nitro-containing intermediates intermediate 25 were subjected to the same 6-step transformation as intermediates 22 to give rise to the final compounds 6, 7, 102 and 103.

Scheme 7. Synthetic procedure for compounds 130 and 131.

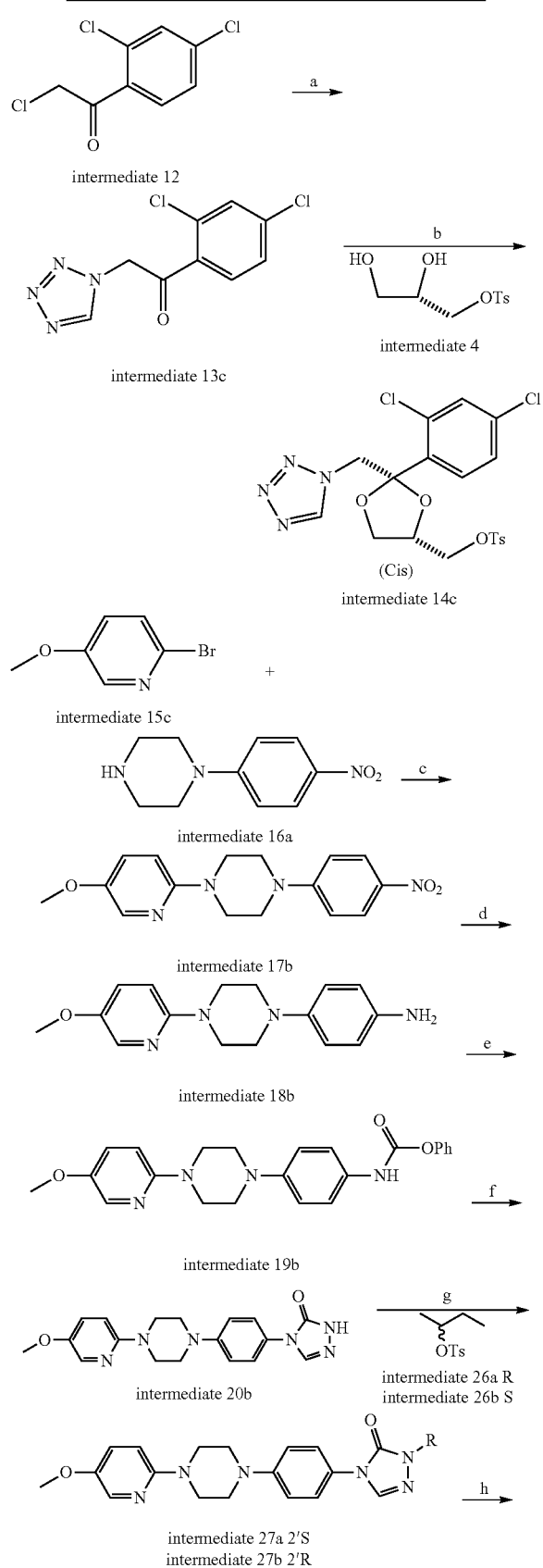

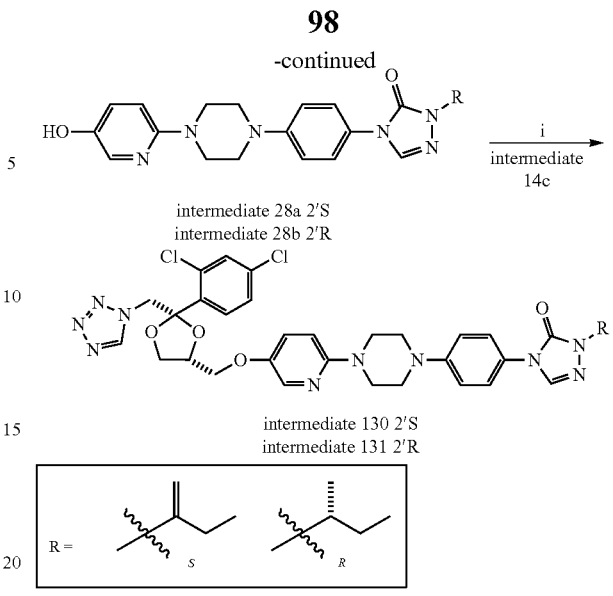

intermediate 130 2'S
intermediate 131 2'R

Reagents and conditions: (a) $^1$H-tetrazole, $K_2CO_3$, CAN, rt, 16 h; (b) TfOH, toluene, rt, 60 h; (c) $Pd_2(dba)_3$, BINAP, NaOtBu, toluene, 80° C., 16 h; (d) 10% Pd/C, $NH_2NH_2$, EtOH, reflux, 3.5 h; (e) Phenyl chloroformate, pyridine, rt, 16 h; (f) 1. $NH_2NH_2 \cdot H_2O$, 1,4-dioxane, reflux, 3 h; 2. formamidine acetate, 1-propanol, reflux, 3 h; (g) $K_2CO_3$, 18-Crown-6, DMSO, room temperature; (h) 48% aqueous HBr, 110° C.; (i) NaH, DMF, 80° C., 16 h.

Scheme 7 shows the synthesis of pure diastereomers on the isobutyl side chain, such as compounds 130 and 131. Synthesis of tetrazole intermediate 14c follows the procedure illustrated in the above sections. The stereocenter on the isobutyl side chain can be introduced through intermediates 26a and 26b.

TABLE 3

Inhibition of HUVEC proliferation, aqueous solubility, and logP of the disclosed Itraconazole analog compounds.

| Compounds | HUVEC inhibition[a] IC50 (nM) | logP[b] | Solubility in 0.001N HCl[c] (ng/mL) |
|---|---|---|---|
| Intraconazole | 170 ± 13.1 | 5.35 | 10.1 |
| Compound 24 | — | 4.92 | 321.4 |
| Compound 100 | 686.8 ± 78.1 | 5.00 | 116.1 |
| Compound 101 | 379.8 ± 50.8 | 4.99 | 113.6 |
| Compound 102 | 221.9 ± 23.1 | 5.02 | 53.9 |
| Compound 103 | 187.8 ± 17.5 | 5.04 | 496.5 |
| Compound 104 | 128.4 ± 59.7 | 5.75 | 29.1 |
| Compound 105 | 446.5 ± 38.3 | 5.12 | 255.4 |
| Compound 106 | 173.1 ± 27.6 | 5.11 | 847.7 |
| Compound 2 | 468.5 ± 42.2 | 5.48 | 6483.0 |
| Compound 4 | 69.1 ± 7.0 | 5.47 | 2938.9 |
| Compound 6 | 98.5 ± 36.3 | 5.49 | 7988.0 |
| Compound 7 | 636.0 ± 177.2 | 5.52 | 41338.6 |
| Compound 1 | 70.1 ± 15.4 | 6.16 | 17150.0 |
| Compound 5 | 68.0 ± 15.5 | 5.61 | 124904.5 |
| Compound 14 | 77.1 ± 11.9 | 4.36 | 951.3 |
| Compound 8 | 153.4 ± 32.7 | 4.96 | 52.8 |
| Compound 15 | 108.5 ± 8.6 | 4.40 | 707.6 |

[a]$IC_{50}$ of HUVEC were evaluated using [$^3$H]-thymidine incorporation assay. Values represent the mean ± SD in three independent experiements carried out in triplicate.
[b]logP was predicted using ALOGPS2.1 software.
[c]Thermodynamic solubility in 0.001N HCl was measured using HPLC.

The inhibitory effects of the new analogs on HUVEC proliferation were measured using a [3H]-thymidine incorporation assay. The log P values, used as an indicator of lipophilicity, were calculated using ALOGPS2.1 software. Aqueous solubility is a key physiochemical property relevant for oral absorption. We determined the solubility of each analog in 0.001 N HCl (pH=3), which represents the acidic human gastric fluid. The IC50 against HUVEC proliferation, log P and solubility of all analogs are shown in Table 3.

Itraconazole was slightly soluble in 0.001N HCl (10.1 ng/mL). In order to disrupt the symmetricity of the phenyl-piperizin-1-yl-phenyl core (W1-piperizin-1-yl-W2), we used pyridyl to replace one phenyl ring in the W1 or W2 position or 3'-fluorophenyl to replace W2. Both pyridine and fluoro-benzene are reasonable benzene isosteres and were not expected to cause significant steric perturbations of the W1-W2 portion of the molecules. Initially, compounds 100-106 with 1,2,4-triazole in the R1 position were synthesized and characterized. Pyridyl substitution at either the W1 (compounds 100 and 101) or W2 (compounds 102 and 103) position and 3'-fluoro-phenyl at W2 (compounds 104-106) all resulted in increases in solubility by 5-84 fold. Pyridin-2-yl and 3'-fluorophenyl combination (compound 106) resulted in the best solubility in this series of analogs (847.7 ng/mL). Pyridine (=N), benzene (=CH), and fluorine-substituted benzene (=CF) are similar in van der Walls radius but quite different in lipophilicity. The lipophilicity of the three groups follows the order: pyridyl<benzyl<fluorobenzyl. As expected, the analogs containing a pyridine (compounds 100-103) exhibited decreases in log P while the fluoro-phenyl analog (compound 104) had an increase in log P. In the HUVEC proliferation assay, compounds 103, 104, and 106 showed similar activity to that of itraconazole, while the other modifications led to decreases in potency.

Figure 6:
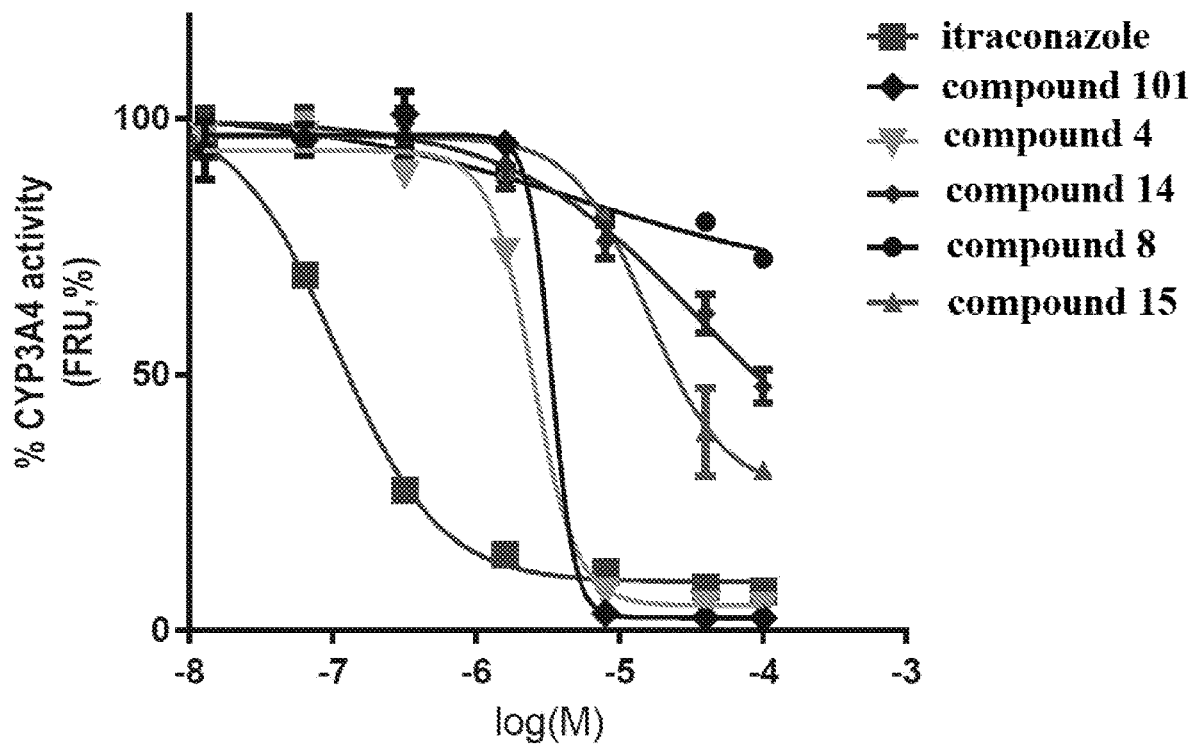
FIG. 6 shows dose-response curves of CYP3A4 enzyme inhibition by itraconazole and compounds 4, 8, 14, 15, and 101.

Next, six analogs with imidazole in the R1 position were synthesized and characterized. Except for compound 2 (pyridin-3-yl) and 7 (pyridin-2'-yl), the other four analogs (compounds 1, 4, 5, and 6) resulted in increased activities for inhibition of HUVEC proliferation. In general, the change of the triazole to an imidazole led to a significant increase in solubility ranging from 6 µg/mL to 12 µg/mL, or 600- to 1200-fold greater than itraconazole. However, the imidazole compounds were more lipophilic (higher log P value) than their 1,2,4-triazole counterparts, which is unfavorable for drug distribution. Moreover, the 1,2,4-triazole- and imidazole-containing compounds still displayed inhibition of CYP3A4, albeit weaker than itraconazole. For example, the IC50 of compounds 101 and 4 for CYP3A4 inhibition were 3.4 µM and 2.6 µM, respectively (FIG. 6).

Our previous SAR study showed that 1H-tetrazole-1-yl in the R1 position significantly reduced CYP3A4 inhibition while increasing anti-angiogenic potency. Thus, three new analogs with either pyridin-2-yl, 3'-fluorophenyl or the combination in the core region and tetrazole in the R1 position were synthesized. As expected, the resulting tetrazole-containing analog compounds 8, 14, and 15 had reduced CYP3A4 inhibition, with IC50 values of 95 µM for compound 14, over 100 µM for compound 8 and 37 µM for compound 15 (FIG. 6). To our delight, the calculated log P values of the three new analogs were further decreased and the log P of compound 14 was reduced to 4.36, falling into the range of orally active drugs according to Lipinski's rule of five. Among the three tetrazole-containing analogs, compound 14 also had the highest potency for HUVEC inhibition (IC50 of 77 nM) and solubility. Compared to itraconazole, the solubility of compound 14 was increased by over 90-fold.

Figure 7A:
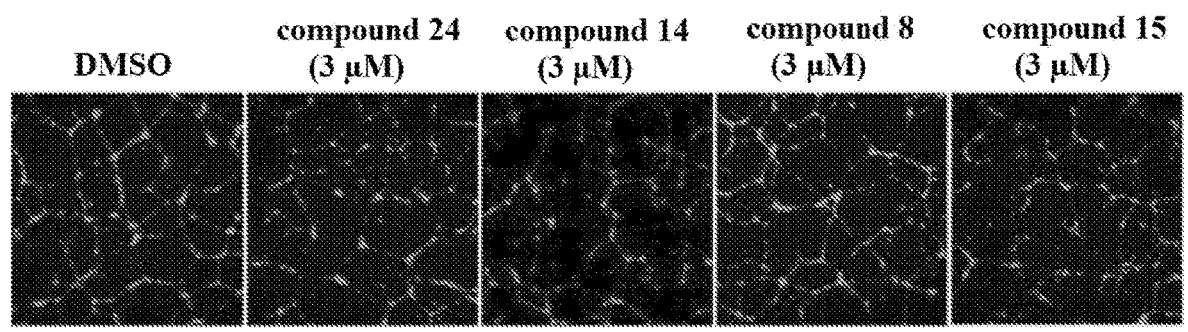
FIG. 7A shows inhibition of HUVEC tube formation when cells were stained with Calcein-AM and vascular networks were imaged using fluorescence microscopy. HUVECs were seeded on Matrigel-coated plates and treated with DMSO or 3 μM of compounds for 24 h.
Figure 7B:
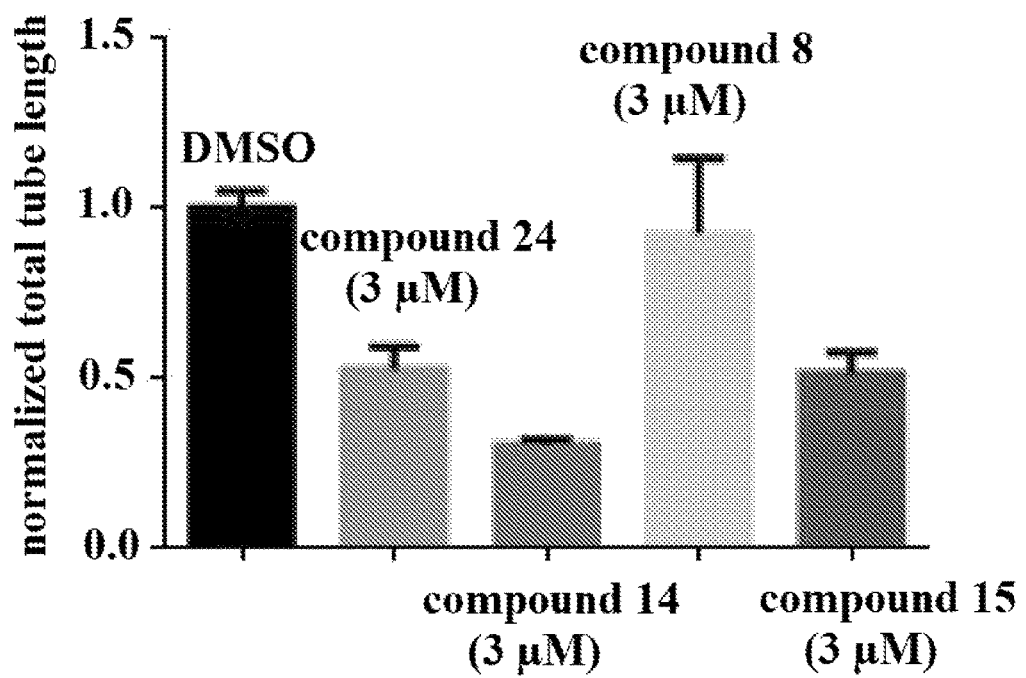
FIG. 7B shows inhibition of HUVEC tube formation when total tube lengths from the fluorescence images were quantified using the ImageJ software and plotted using GraphPad Prism. HUVECs were seeded on Matrigel-coated plates and treated with DMSO or 3 μM of compounds for 24 h. Data represent mean±SD of three independent experiments.

Inhibition of HUVEC tube formation. Tetrazole compounds 8, 14, and 15 were selected for endothelial cell tube formation assay to further assess their anti-angiogenic potential, with compound 24 as a positive control. In this assay, HUVECs assembled into three-dimensional networks and formed tubular structures in Matrigel-coated wells, which recapitulates many key aspects of new blood vessel formation in vivo. As shown in FIG. 7, compound 14 inhibited 70% of HUVEC tube formation at 3 µM, as judged by total tube length. The ranked ability to inhibit tube formation was compound 14>compound 15>compound 8, which is consistent with their anti-proliferative activity in HUVEC.

Figure 8:
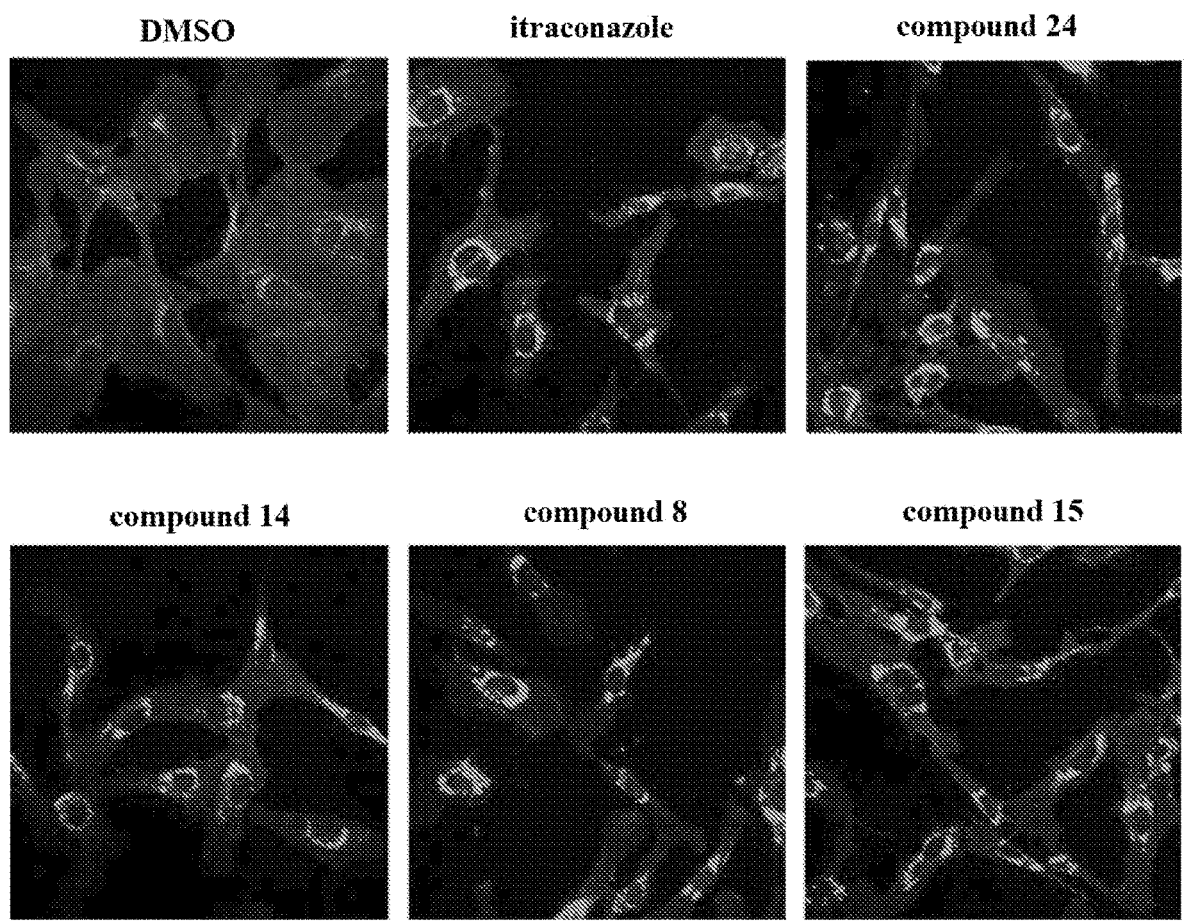
FIG. 8 shows induction of NPC phenotype. HUVECs were treated with 0.2 μM itraconazole, compounds 8, 14, 15, 24, or DMSO for 24 h. Intracellular cholesterol was stained with filipin and fluorescent images were captured using LSM710 confocal microscope with 25× objective.
Figure 9:
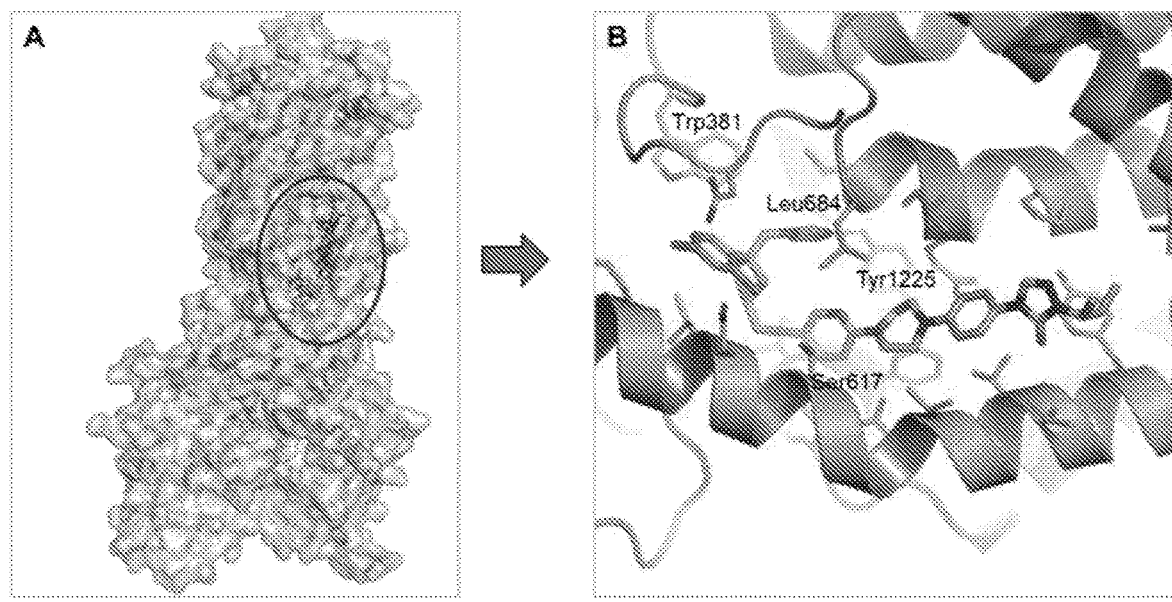
FIG. 9A shows the predicted binding mode of itraconazole and compound 14 with NPC1 (PDB code: 5I31) by AutoDock Vina software.
FIG. 9B shows the predicted interaction of compound 14 with the SSD.
Figure 10A:
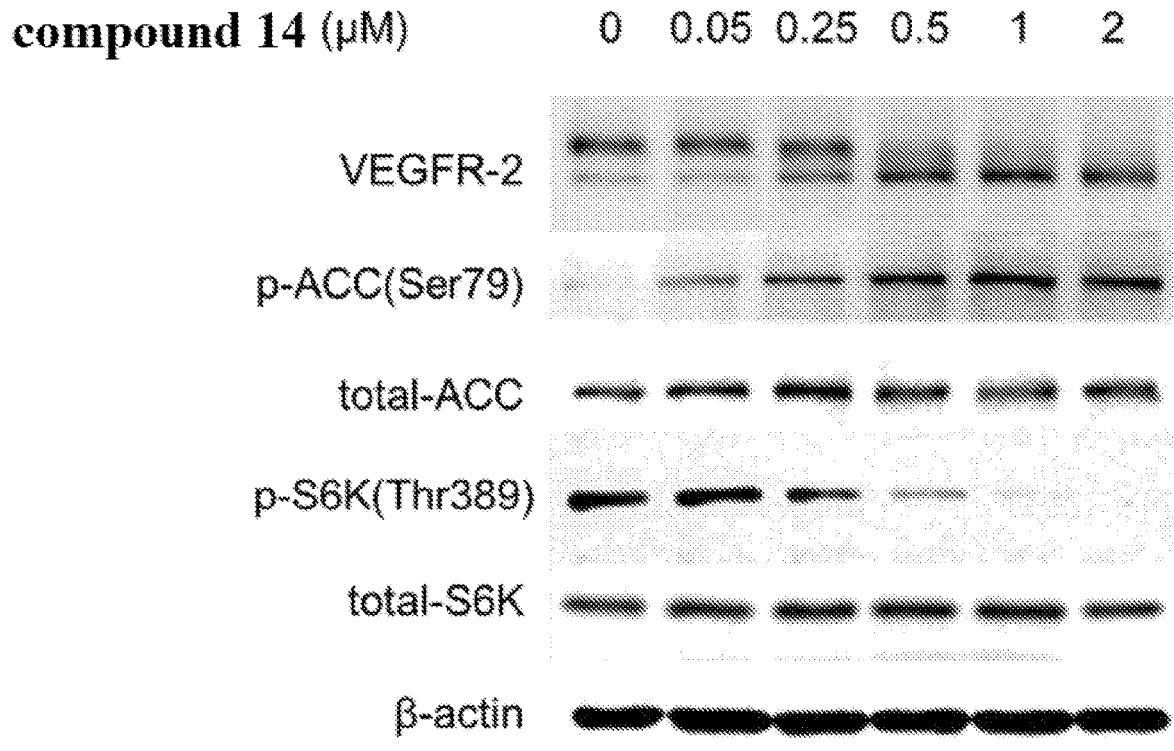
FIG. 10A shows inhibition of VEGFR2 and AMPK/mTOR in HUVEC, in which HUVECs were treated with 0.05 μM, 0.25 μM, 0.5 μM or 2 μM compound 14 or DMSO for 24 h. VEGFR2, p-ACC, total-ACC, p-S6K, total S6K and β-actin proteins were analyzed by western blot.
Figure 10B:
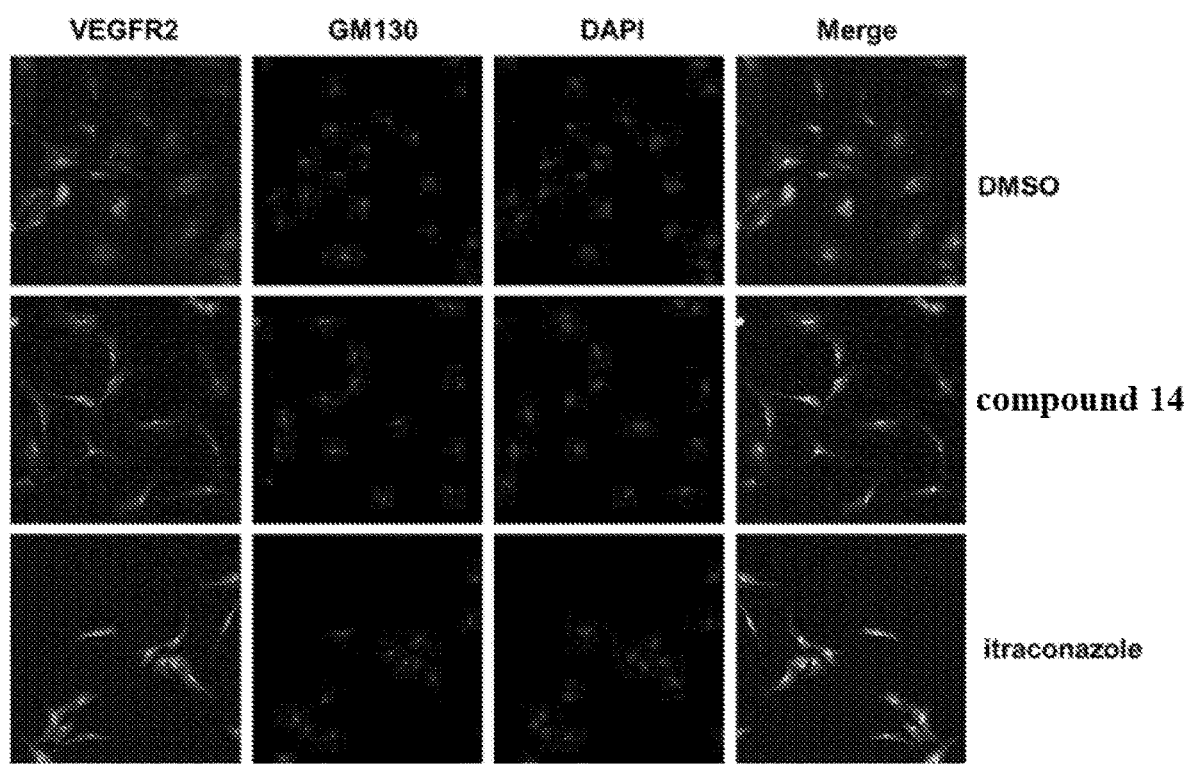
FIG. 10B shows inhibition of VEGFR2 and AMPK/mTOR in HUVEC, in which HUVECs were treated with DMSO, 2 μM compound 14 or itraconazole, in which the cells were stained with VEGFR2, GM130 antibody and DAPI. Images were captured using LSM 700 confocal microscopy.

Inhibition of NPC1. NPC1 plays an essential role in cholesterol export from the endolysosome. Previously, there are reports that itraconazole and its structurally related drug posaconazole directly bind to NPC1 and induce NPC phenotype in endothelial cells. Using filipin staining, we observed that compound 14 caused a massive build-up of cholesterol in the perinuclear structure, in the same manner as itraconazole and the other tetrazole-containing analog compounds 24, 8, and 15 (FIG. 8). These results suggested that the pyridinyl and fluorophenyl analogs maintained NPC1 inhibitory activity. To evaluate the binding of compound 14 to NPC1 protein, we performed docking of compound 14 and itraconazole into the pocket within the sterol-sensing domain (SSD) using AutoDock Vina software. As shown in FIG. 9A, itraconazole and compound 14 are predicted to bind to NPC1 in a similar manner. At a close view (FIG. 9B), the linear pyridinyl-piperizin-1-yl-phenyl core of compound 14 nestled into the hydrophobic channel created by the transmembrane helix. The isobutyl tail faced toward the open entrance of this channel. The tetrazole moiety pointed into the closed end of the pocket and interacted with the hydroxyl group of Tyr1225 via hydrogen bonding. These results offer a plausible explanation for how the benzene bioisostere replacement could modify the physiochemical properties of itraconazole without compromising NPC1 inhibition.

mTOR and VEGFR2 inhibition. We then determined the effects of compound 14 on AMPK/mTOR activity and VEGFR2 glycosylation. Similar to itraconazole, compound 14 activated AMPK as judged by the phosphorylation of its substrate acetyl CoA carboxylase (ACC) in a dose-dependent manner (FIG. 10A). AMPK activation and NPC1 inhibition were demonstrated to lead to synergistic mTOR inhibition by itraconazole. Indeed, compound 14 potently inhibited the phosphorylation of the mTOR substrate p70 S6 Kinase (S6K). At higher doses of 1 µM and 2 µM, S6K phosphorylation was completely abolished. We have previously reported that itraconazole inhibits VEGFR2 glycosylation and surface expression. We observed two VEGFR2 bands by Western blotting, representing differentially glycosylated forms of the receptor, with the higher molecular weight band being more predominant in untreated HUVEC. Treatment with compound 14 caused a mobility shift to the lower molecular weight, hypoglycosylated band. The high molecular weight species of VEGFR2 disappeared upon treatment with compound 14 at concentrations of 0.5 µM or higher (FIG. 10A). We next determined whether compound 14 and other analogs affected cellular localization of VEGFR2 using immunofluorescence (FIG. 10B). In compound 14 and itraconazole-treated cells, VEGFR2 accumulated in the perinuclear region and colocalized with the Golgi marker, GM130. In contrast, in the untreated cells VEGFR2 was uniformly distributed in small puncta throughout the cytoplasm. As a critical component of lipid rafts, cholesterol is pivotal to intracellular transportation and cell signaling. In our previous study, we demonstrated that the hypoglycosylation of VEGFR2 was rescued by supplementation of cellular cholesterol. It is therefore possible that VEGFR2 relocalization and inhibition by itraconazole and its analogs may be mediated through inhibition of NPC1. Taken together, these results indicate that compound 14 inhibits endothelial cell growth and angiogenesis by concurrent inhibition of NPC1 and VDAC1, leading to activation of AMPK, and inhibition of mTOR and VEGFR2 signaling.

Anti-angiogenic therapy has been clinically validated for the treatment of a number of diseases including cancer, autoimmune disorders, retinopathy, obesity, macular degeneration and others. Itraconazole has great potential as a newly identified angiogenesis inhibitor and is being investigated in multiple clinical trials. However, its wider use as an anti-angiogenic agent in general, and its use in combination with other drugs for treating cancer in particular, has been limited by its inhibition of CYP450 and unfavorable physicochemical properties. To improve its solubility and decrease its lipophilicity, we used pyridyl or fluorophenyl to replace the phenyl group in the core region of itraconazole. Among the newly synthesized analogs, compound 14 with 2-pyridyl in W1 and 1H-tetrazol-1-yl in R1 position exhibited improved anti-angiogenic activity, solubility and hydrophilicity with negligible effects on CYP3A4. The anti-angiogenic activity of compound 14 was further validated using a tube formation assay. Moreover, compound 14 bears all the hallmarks of itraconazole activity in endothelial cells, including activation of AMPK and inhibition of mTOR, induction of cholesterol accumulation in the endolysosome and binding to NPC1, and inhibition of VEGFR2 glycosylation, suggesting that the structural changes required to improve its pharmacological properties did not alter its mechanism of action. This work paves the way for compound 14 to undergo further preclinical studies as a novel anti-angiogenic and anticancer drug candidate. It has been reported that tetrazole-containing compounds also have good anti-fungal activity. It will be interesting to determine whether compound 14 has anti-fungal activity as well.

General experimental conditions. Reactions were carried out in oven-dried glassware. All reagents were purchased from commercial sources and were used without further purification unless noted. Unless otherwise stated, all reactions were carried out under argon atmosphere, monitored by Merck pre-coated silica gel 60E-254 plates and visualized using 254 nm UV light. Column chromatography was performed on normal-phase silica flash columns (RediSepRf). NMR data were collected on Bruker Avance III (500 MHz 1H, 125 MHz 13C) machine in the Department of Pharmacology and Molecular Sciences, the Johns Hopkins University, School of Medicine. 1H NMR spectra and 13C NMR spectra were obtained in deuteriochloroform (CDCl3) with tetramethylsilane (TMS, $\delta$=0.00 for 1H) as an internal reference. Chemical shifts are reported in ppm ($\delta$). Data are presented in the form: chemical shift (multiplicity, coupling constants, and integration). Low resolution ESI-MS and HPLC purity were recorded on an Agilent 6120 quadrupole LC/MS. The reported purity values were obtained with a Pursuit XRs Diphenyl column (150×4.5 mm) and a diode array detector (DAD). A flow rate of 1.0 ml/min was used with a mobile phase of acetonitrile in H2O with a 0.1% modifier (formic acid, v/v).

General experimental procedure for compounds 57, 59-62, 33-35, 38-41, 43, 45, 46, and 48-53. To a solution of tosylates 103 or 108 (1 eq) in dry DMF was added sodium hydride (NaH, 60% dispersion in mineral oil, (1.5 eq) under argon atmosphere. After the reaction mixture was stirred at 50° C. for 1 hour. A solution of 105a (1.2 eq) in DMF was adder slowly at the same temperature. After the addition the temperature was increased to 90° C. and stirred for another 3 hours. The reaction mixture was quenched by the saturated sodium chloride, and the resulting mixture was extracted twice with dichloromethane. The organic fractions were dried over Na2SO4, filtered and concentrated under vacuum to yield the crude product which was purified by column chromatography to afford the desired products in moderate to good yields.

1-(2,4-dichlorophenyl)-2-(5-methyl-1H-tetrazol-1-yl) ethan-1-one (intermediate 13c). To a solution of 1.44 g tetrazole and 3.1 g anhydrous K2CO3 in 150 mL acetonitrile (ACN), 4.2 g 2-chloro-1-(2,4-dichlorophenyl)ethenone (intermediate 12) was added dropwise. The reaction mixture was stirred for 16 h at room temperature before water was added. The mixture was extracted with ethyl acetate (EtOAc) three times, washed with brine and dried over MgSO4. The solution was concentrated under reduced pressure and purified by column chromatography (1.9 g, yield 40%). 1H NMR (500 MHz, CDCl3, $\delta$H): 7.71 (d, J=8.5 Hz, 1H), 7.48 (d, J=2.0 Hz, 1H), 7.37 (m, 1H), 5.80 (s, 2H), 2.46 (s, 3H). 13C NMR (125 MHz, CDCl3, $\delta$C): 190.1, 153.2, 140.0, 133.2, 132.6, 131.8, 131, 131.0, 130.4, 128.1, 55.3, 8.7. ESI-MS [M+H]+ 257.2.

((2S,4S)-2-((1H-tetrazol-1-yl)methyl)-2-(2,4-dichlorophenyl)-1,3-dioxolan-4-yl)methyl 4-methylbenzenesulfonate (intermediate 14c) intermediate 12c (1 g) and intermediate 13 (1.1 g) were dissolved in 15 mL dry toluene under ice bath. Triflic acid (TfOH, 1.53 mL) was added and the ice bath was removed. The reaction was stirred at room temperature for 60 h. The reaction progress was monitored by TLC. The reaction was quenched by adding saturated aqueous NaHCO3, then extracted with ethyl acetate, washed with brine and dried over Na2SO4. The solvent was removed under reduced pressure and the crude product was purified by column chromatography to afford the cis dioxalane-product (intermediate 14c) as a light-yellow oil (0.98 g, yield 55%). 1H NMR (500 MHz, CDCl3, $\delta$H): 8.41 (s, 1H), 7.79 (d, J=8.5 Hz, 1H), 7.46 (d, J=2 Hz, 1H), 7.43-7.38 (m, 3H), 7.21 (dd, J=8.5, 2.0 Hz, 1H), 5.30-5.17 (m, 2H), 4.27-4.25 (m, 1H), 3.92-3.88 (m, 1H), 3.86-3.84 (m, 1H), 3.76-3.74 (m, 1H), 3.61-3.57 (m, 1H), 2.48 (s, 3H). 13C NMR (125 MHz, CDCl3, $\delta$C): 154.4, 151.9, 121.0, 118.9, 117.3, 114.6, 112.8, 112.5, 55.6, 51.0, 49.6. ESI-MS [M+H]+ 485.3.

1-(2-Fluoro-4-nitrophenyl)-4-(4-methoxyphenyl) piperazine (intermediate 17c) In a dry flask, 1-(2-fluoro-4-nitrophenyl)piperazine (intermediate 16b, 550 mg), was mixed with 1-bromo-4-methoxybenzene (intermediate 15a, 500 mg), tris(dibenzylideneacetone)dipalladium (Pd2(dba)3, 120 mg), sodium t-butoxide (NaOt-Bu, 380 mg), and ($\pm$)-2,2'-bis(diphenylphosphino)-1,1'-binaphthalene (BINAP, 245 mg) in 20 mL dry toluene. The mixture was stirred overnight at 80° C. under argon protection. After cooling to room temperature, water was added and the organic phase was separated. The aqueous phase was extracted three times with dichloromethane (DCM). The combined organic layer was dried over Na2SO4, which was purified by column chromatography to get intermediate 17c as a yellowish solid (2.5 g, yield 75%). 1H NMR (500 MHz, CDCl3, $\delta$H): 8.01 (dd, J=8.8, 2.4 Hz, 1H), 7.93 (dd, J=12.8, 2.4 Hz, 1H), 6.99-6.97 (m, 3H), 6.89-6.87 (m, 2H), 3.79 (s, 3H), 3.47 (bs, 4H), 3.26 (d, J=4.8 Hz, 4H). 13C NMR (125 MHz, CDCl3, $\delta$C): 154.4, 151.9, 121.0, 118.9, 117.3, 114.6, 112.8, 112.5, 55.6, 51.0, 49.6. ESI-MS [M+H]+ 332.2.

1-(sec-butyl)-4-(3-fluoro-4-(4-(4-methoxyphenyl)piperazin-1-yl)phenyl)-1H-1,2,4-triazol-5(4H)-one (intermediate 21c). To a suspension of 0.55 g triazolone intermediate 20c in 20 mL dimethylsulfoxide was added 0.4 g K2CO3. The resulting mixture was stirred at room temperature for 6 h. An aliquot of 0.25 mL 2-bromobutane was added dropwise at room temperature. Then the temperature was increased to 80° C. and stirred overnight. After cooling, the reaction mixture was diluted with water and extracted with EtOAc. The combined organic layer was dried over NaSO4, filtered, and concentrated under reduced vacuum to yield the crude product, which was purified by column chromatography to obtain intermediate 21c (0.55 g, yield 87%). 1H NMR (500 MHz, CDCl3, δH): 7.64 (s, 1H), 7.37 (dd, J=13.0, 2.2 Hz, 1H), 7.26-7.24 (m, 1H), 7.04 (t, J=8.8 Hz, 1H), 6.99-6.97 (m, 2H), 6.88-6.84 (m, 2H), 4.31-4.26 (m, 1H), 3.77 (s, 3H), 3.26 (bs, 8H), 1.86-1.81 (m, 1H), 1.73-1.71 (m, 1H), 1.38 (d, J=6.8 Hz, 3H), 0.89 (t, J=7.4 Hz, 3H). 13C NMR (125 MHz, CDCl3, δC): 154.6, 1542, 151.6, 139.4, 133.3, 128.4, 119.4, 118.7, 118.0, 114.5, 111.0, 110.8, 55.6, 52.8, 51.0, 50.5, 28.4, 19.3, 10.8. ESI-MS [M+H]+: 425.5.

1-(sec-butyl)-4-(3-fluoro-4-(4-(4-hydroxyphenyl)piperazin-1-yl)phenyl)-1H-1,2,4-triazol-5(4H)-one (intermediate 22c). 0.5 g triazolone intermediate 21c was added to aqueous HBr (48%, 10 mL) in a flask. The reaction was heated to 120° C. and refluxed overnight. After cooling to room temperature, the solution was neutralized with cold saturated Na2CO3 and extracted 3 times with DCM. The combined organic layer was dried with Na2SO4, filtered, and concentrated to yield the crude product, which was purified by column chromatography to obtain intermediate 22c (0.4 g, yield 83%). 1H NMR (500 MHz, CDCl3, δH): 7.57 (s, 1H), 7.24 (dd, J=10.2, 2.0 Hz, 1H), 7.15 (dd, J=6.8, 1.6 Hz, 1H), 6.92 (t, J=7.0 Hz, 1H), 6.79 (d, J=6.8 Hz, 2H), 6.67 (d, J=7.2 Hz, 2H), 4.24-4.20 (m, 1H), 3.17-3.16 (m, 8H), 1.82-1.77 (m, 1H), 1.66-1.63 (m, 1H), 1.32 (d, J=5.6 Hz, 3H), 0.82 (t, J=5.8 Hz, 3H). 13C NMR (125 MHz, CDCl3, δC): 156.3, 154.3, 150.8, 144.9, 139.7, 133.6, 127.8, 119.4, 118.9, 116.0, 111.4, 53.1, 51.2, 50.5, 28.4, 19.3, 10.8. ESI-MS [M+H]+: 411.5.

4-(4-(4-(4-(((2S,4R)-2-((1H-imidazol-1-yl)methyl)-2-(2,4-dichlorophenyl)-1,3-dioxolan-4-yl)methoxy)phenyl)piperazin-1-yl)-3-fluorophenyl)-2-(sec-butyl)-2,4-dihydro-3H-1,2,4-triazol-3-one (compound 1). 1H NMR (500 MHz, CDCl3, δH): 8.08 (s, 1H), 7.64 (s, 1H), 7.59 (d, J=8.5 Hz, 1H), 7.49 (d, J=2.0 Hz, 1H), 7.40 (d, J=2.0 Hz, 1H), 7.39 (dd, J=13.0, 2.5 Hz, 1H), 7.30 (dd, J=8.5, 2.0 Hz, 1H), 7.25-7.23 (m, 2H), 7.15-7.12 (m, 2H), 7.08-7.04 (m, 1H), 7.01 (d, J=8.5 Hz, 1H), 6.82 (d, J=9.0 Hz, 1H), 4.61 (q, J=14.5 Hz, 2H), 4.39-4.36 (m, 1H), 4.32-4.27 (m, 1H), 3.93 (t, J=8.5 Hz, 1H), 3.82-3.79 (m, 1H), 3.75-3.73 (m, 1H), 3.59-3.56 (m, 1H), 3.35-3.33 (m, 4H), 3.30-3.29 (m, 4H), 1.90-1.84 (m, 1H), 1.76-1.70 (m, 1H), 1.41 (d, J=7.0 Hz, 3H), 0.91 (t, J=7.0 Hz, 3H). 13C NMR (125 MHz, CDCl3, δC): 156.4, 152.4, 151.8, 146.1, 140.4, 136.6, 134.3, 133.8, 133.0, 131.5, 129.6, 128.2, 127.8, 119.4, 118.9, 115.7, 111.2, 109.8, 107.2, 74.8, 70.7, 68.7, 67.4, 52.2, 50.4, 48.9, 28.4, 19.3, 10.8. HRMS (ESI) calcd for C36H38Cl2FN7O4: 722.2425; found 722.2429. HPLC Purity: 95.8%, tR=5.6 min.

4-(4-(4-(6-(((2S,4R)-2-((1H-imidazol-1-yl)methyl)-2-(2,4-dichlorophenyl)-1,3-dioxolan-4-yl)methoxy)pyridin-3-yl)piperazin-1-yl)phenyl)-2-(sec-butyl)-2,4-dihydro-3H-1,2,4-triazol-3-one (compound 2). 1H NMR (500 MHz, CDCl3, δH): 8.22 (s, 1H), 7.57 (s, 1H), 7.40 (m, 1H), 7.39-7.37 (m, 3H), 7.32 (dd, J=9.5, 3 Hz, 1H), 7.18 (dd, J=8.5, 2 Hz, 1H), 7.14 (s, 1H), 7.01 (s, 1H), 6.99 (d, J=9.0 Hz, 2H), 6.74 (d, J=3.0 Hz, 1H), 6.52 (d, J=9.0 Hz, 1H), 4.58 (q, J=14.5 Hz, 2H), 4.35-4.32 (m, 1H), 4.26-4.21 (m, 1H), 4.05-4.01 (m, 1H), 3.94-3.91 (m, 1H), 3.59-3.56 (m, 1H), 3.51-3.46 (m, 1H), 3.35-3.32 (m, 4H), 3.06 (t, J=5.0 Hz, 4H), 1.87-1.78 (m, 1H), 1.72-1.63 (m, 1H), 1.36 (d, J=7.0 Hz, 3H), 0.86 (t, J=7.0 Hz, 3H). 13C NMR (125 MHz, CDCl3, δC): 156.3, 152.6, 151.3, 146.4, 136.0, 138.9, 134.2, 133.8, 133.2, 131.6, 130.1, 129.5, 127.3, 123.4, 117.0, 111.2, 107.4, 74.8, 67.2, 64.9, 53.8, 52.8, 50.6, 49.3, 41.0, 28.5, 19.3, 10.8. HRMS (ESI) calcd for C35H38Cl2N8O4: 705.2471; found 705.2463. HPLC Purity: 96.3%, tR=3.6 min.

4-(4-(4-(5-(((2S,4R)-2-((1H-imidazol-1-yl)methyl)-2-(2,4-dichlorophenyl)-1,3-dioxolan-4-yl)methoxy)pyridin-2-yl)piperazin-1-yl)phenyl)-2-(sec-butyl)-2,4-dihydro-3H-1,2,4-triazol-3-one (compound 4). 1H NMR (500 MHz, CDCl3, δH): 7.90-7.87 (m, 2H), 7.62 (s, 1H), 7.61 (d, J=8.0 Hz, 1H), 7.49 (d, J=2.5 Hz, 1H), 7.44 (m, 3H), 7.30 (dd, J=8.0, 2 Hz, 1H), 7.19-7.17 (m, 1H), 7.11 (s, 1H), 7.04 (d, J=9.0 Hz, 2H), 6.76 (d, J=8.5 Hz, 1H), 4.57 (q, J=14.5 Hz, 2H), 4.38-4.35 (m, 1H), 4.32-4.28 (m, 1H), 3.93-3.90 (m, 1H), 3.78-3.76 (m, 1H), 3.74-3.71 (m, 1H), 3.64-3.62 (m, 4H), 3.51-3.48 (m, 1H), 3.35-3.34 (m, 4H), 1.91-1.84 (m, 1H), 1.75-1.70 (m, 1H), 1.41 (d, J=6.5 Hz, 3H), 0.91 (t, J=6.5 Hz, 3H). 13C NMR (125 MHz, CDCl3, δC): 156.4, 152.1, 150.6, 138.7, 136.3, 134.2, 134.0, 133.0, 132.0, 131.6, 129.5, 127.4, 126.0, 123.6, 116.8, 107.7, 98.1, 74.8, 68.5, 52.7, 48.9, 46.3, 29.7, 28.5, 19.3, 10.8. HRMS (ESI) calcd for C35H38Cl2N8O4: 705.2471; found 705.2473. HPLC Purity: 95.4%, tR=3.7 min.

4-(4-(4-(5-(((2S,4R)-2-((1H-imidazol-1-yl)methyl)-2-(2,4-dichlorophenyl)-1,3-dioxolan-4-yl)methoxy)pyridin-2-yl)piperazin-1-yl)-3-fluorophenyl)-2-(sec-butyl)-2,4-dihydro-3H-1,2,4-triazol-3-one (compound 5). 1H NMR (500 MHz, CDCl3, δH): 8.02 (d, J=2.5 Hz, 1H), 7.75 (s, 1H), 7.66-7.65 (m, 2H), 7.49 (d, J=2.0 Hz, 1H), 7.40 (t, J=2.0 Hz, 1H), 7.37 (t, J=2.0 Hz, 1H), 7.30-7.27 (m, 1H), 7.26-7.24 (m, 1H), 7.15 (dd, J=9.0, 2.5 Hz, 1H), 7.07-7.01 (m, 2H), 6.71 (t, J=8.5 Hz, 1H), 4.55 (q, J=14.5 Hz, 2H), 4.38-4.27 (m, 2H), 3.92-3.88 (m, 1H), 3.77-3.72 (m, 2H), 3.63-3.60 (m, 4H), 3.45-3.41 (m, 1H), 3.25-3.21 (m, 4H), 1.91-1.82 (m, 1H), 1.77-1.68 (m, 1H), 1.40 (d, J=7.5 Hz, 3H), 0.91 (t, J=7.5 Hz, 3H). 13C NMR (125 MHz, CDCl3, δC): 156.6, 155.2, 151.7, 148.0, 141.3, 136.1, 134.6, 133.3, 133.0, 131.5, 129.5, 127.4, 125.7, 119.5, 118.0, 110.8, 108.3, 74.8, 67.3, 52.9, 50.3, 47.0, 46.5, 28.4, 19.3, 10.8. HRMS (ESI) calcd for C35H37Cl2FN8O4: 723.2377; found 723.2371. HPLC Purity: 95.8%, tR=4.3 min.

4-(6-(4-(4-(((2S,4R)-2-((1H-imidazol-1-yl)methyl)-2-(2,4-dichlorophenyl)-1,3-dioxolan-4-yl)methoxy)phenyl)piperazin-1-yl)pyridin-3-yl)-2-(sec-butyl)-2,4-dihydro-3H-1,2,4-triazol-3-one (compound 6). 1H NMR (500 MHz, CDCl3, δH): 8.26 (d, J=3.0 Hz, 1H), 7.75 (dd, J=9.0, 3.0 Hz, 1H), 7.63 (s, 1H), 7.60-7.57 (m, 2H), 7.48 (d, J=2.0 Hz, 1H), 7.28 (dd, J=8.0, 2.0 Hz, 1H), 7.04-7.00 (m, 2H), 6.95-6.93 (m, 2H), 6.80-6.76 (m, 3H), 4.52 (q, J=14.5 Hz, 2H), 4.38-4.27 (m, 2H), 3.91-3.86 (m, 1H), 3.77-3.72 (m, 6H), 3.38-3.34 (m, 1H), 3.20-3.18 (t, J=4.5 Hz, 4H), 1.92-1.83 (m, 1H), 1.77-1.69 (m, 1H), 1.41 (d, J=7.0 Hz, 3H), 0.91 (t, J=7.0 Hz, 3H). 13C NMR (125 MHz, CDCl3, δC): 158.4, 152.7, 152.1, 146.0, 142.4, 136.0, 134.4, 133.8, 132.9, 131.5, 129.6, 127.3, 121.3, 118.6, 115.3, 107.9, 107.1, 74.9, 67.7, 52.9, 50.5, 45.4, 28.5, 19.3, 10.8. HRMS (ESI) calcd for C35H38Cl2N8O4: 705.2471; found 705.2468. HPLC Purity: 96.1%, tR=4.6 min.

4-(5-(4-(4-(((2S,4R)-2-((1H-imidazol-1-yl)methyl)-2-(2,4-dichlorophenyl)-1,3-dioxolan-4-yl)methoxy)phenyl)piperazin-1-yl)pyridin-2-yl)-2-(sec-butyl)-2,4-dihydro-3H-1,2,4-triazol-3-one (compound 7). 1H NMR (500 MHz, CDCl3, δH): 8.34 (s, 1H), 8.22 (d, J=9.0 Hz, 1H), 8.22 (d, J=3.0 Hz, 1H), 7.77 (s, 1H), 7.60 (d, J=8.5 Hz, 1H), 7.76 (d, J=2.0 Hz, 1H), 7.41 (dd, J=9.0, 3.0 Hz, 1H), 7.28 (dd, J=8.5, 2.0 Hz, 1H), 7.05-7.01 (m, 2H), 6.96 (d, J=9.0 Hz, 1H), 6.81 (d, J=9.0 Hz, 1H), 4.54 (q, J=14.5 Hz, 2H), 4.38-4.28 (m, 2H), 3.91-3.88 (m, 1H), 3.78-3.72 (m, 2H), 3.39-3.36 (m, 4H), 3.27-3.25 (m, 5H), 1.90-1.85 (m, 1H), 1.75-1.71 (m, 1H), 1.41 (d, J=7.0 Hz, 3H), 0.91 (t, J=7.0 Hz, 3H). 13C NMR (125 MHz, CDCl3, δC): 152.8, 145.8, 140.2, 136.1, 134.3, 133.0, 132.5, 131.5, 129.6, 127.3, 125.6, 118.6, 115.3, 113.7, 107.8, 74.9, 67.7, 52.6, 50.5, 49.0, 28.4, 19.3, 10.8. HRMS (ESI) calcd for C35H38Cl2N8O4: 705.2471; found 705.2463. HPLC Purity: 95.6%, tR=5.5 min.

4-(4-(4-(4-(((2S,4R)-2-((1H-tetrazol-1-yl)methyl)-2-(2,4-dichlorophenyl)-1,3-dioxolan-4-yl)methoxy)phenyl)piperazin-1-yl)-3-fluorophenyl)-2-(sec-butyl)-2,4-dihydro-3H-1,2,4-triazol-3-one (compound 8). 1H NMR (500 MHz, CDCl3, δH): 8.46 (s, 1H), 7.64 (s, 1H), 7.56 (d, J=8.0 Hz, 1H), 7.48 (s, 1H), 7.39 (d, J=3.0 Hz, 1H), 7.27-7.23 (m, 3H), 7.05 (t, J=8.5 Hz, 1H), 6.94 (d, J=8.5 Hz, 2H), 6.80 (d, J=8.5 Hz, 2H), 5.35 (q, J=14.0 Hz, 2H), 4.40-4.38 (m, 1H), 4.31-4.27 (m, 1H), 3.96 (t, J=8.0 Hz, 1H), 3.89-3.83 (m, 2H), 3.53 (t, J=8.0 Hz, 1H), 3.41-3.38 (m, 8H), 1.90-1.83 (m, 1H), 1.76-1.70 (m, 1H), 1.41 (d, J=7.0 Hz, 3H), 0.91 (t, J=7.0 Hz, 3H). 13C NMR (125 MHz, CDCl3, δC): 156.9, 154.9, 153.1, 152.2, 146.7, 140.0, 136.9, 134.3, 134.0, 132.1, 130.2, 129.0, 128.9, 127.9, 120.1, 119.1, 118.7, 116.1, 111.8, 111.6, 108.2, 75.9, 69.0, 68.7, 57.8, 54.1, 51.9, 51.8, 29.8, 20.7, 12.5. HRMS (ESI) calcd for C34H36Cl2FN9O4: 724.2330; found 724.2328. HPLC Purity: 96.7%, tR=12.7 min.

4-(4-(4-(5-(((2S,4R)-2-((1H-tetrazol-1-yl)methyl)-2-(2,4-dichlorophenyl)-1,3-dioxolan-4-yl)methoxy)pyridin-2-yl)piperazin-1-yl)phenyl)-2-(sec-butyl)-2,4-dihydro-3H-1,2,4-triazol-3-one (compound 14). 1H NMR (500 MHz, CDCl3, δH): 8.47 (s, 1H), 7.88 (d, J=2.5 Hz, 1H), 7.61 (s, 1H), 7.56 (d, J=8.5 Hz, 1H), 7.49 (d, J=1.5 Hz, 1H), 7.43 (d, J=9.0 Hz, 2H), 7.26-7.24 (m, 1H), 7.15 (dd, J=9.0, 3.0 Hz, 1H), 7.04 (d, J=9.0 Hz, 2H), 6.70 (d, J=9.0 Hz, 1H), 5.35 (q, J=14.0 Hz, 2H), 4.41-4.36 (m, 1H), 4.32-4.28 (m, 1H), 3.96 (t, J=8.0 Hz, 1H), 3.88-3.82 (m, 2H), 3.62-3.57 (m, 5H), 3.35-3.33 (m, 4H), 1.92-1.83 (m, 1H), 1.77-1.68 (m, 1H), 1.41 (d, J=7.0 Hz, 3H), 0.91 (t, J=7.0 Hz, 3H). 13C NMR (125 MHz, CDCl3, δC): 155.7, 152.5, 151.1, 148.5, 136.9, 135.3, 134.2, 134.0, 132.2, 130.0, 127.9, 126.7, 126.5, 124.3, 117.5, 109.0, 75.8, 69.8, 68.5, 57.8, 53.9, 50.2, 47.5, 29.9, 20.8, 12.4. HRMS (ESI) calcd for C33H36Cl2N10O4: 707.2376; found 707.2379. HPLC Purity: 98.9%, tR=8.2 min.

4-(4-(4-(5-(((2S,4R)-2-((1H-tetrazol-1-yl)methyl)-2-(2,4-dichlorophenyl)-1,3-dioxolan-4-yl)methoxy)pyridin-2-yl)piperazin-1-yl)-3-fluorophenyl)-2-(sec-butyl)-2,4-dihydro-3H-1,2,4-triazol-3-one (compound 15). 1H NMR (500 MHz, CDCl3, δH): 8.47 (s, 1H), 7.88 (d, J=3.0 Hz, 1H), 7.64 (s, 1H), 7.56 (d, J=8.5 Hz, 1H), 7.49 (d, J=2.0 Hz, 1H), 7.39 (dd, J=13.0, 2.5 Hz, 1H), 7.25-7.24 (m, 2H), 7.14 (dd, J=9.0, 3.0 Hz, 1H), 7.04 (t, J=9.0 Hz, 1H), 6.69 (d, J=9.0 Hz, 1H), 5.35 (q, J=14.5 Hz, 2H), 4.39-4.37 (m, 1H), 4.30-4.28 (m, 1H), 3.98-3.94 (m, 1H), 3.88-3.82 (m, 1H), 3.65-3.56 (m, 5H), 3.23 (t, J=5.0 Hz, 3H), 1.89-1.83 (m, 1H), 1.76-1.69 (m, 1H), 1.40 (d, J=6.5 Hz, 3H), 0.91 (t, J=6.5 Hz, 3H). 13C NMR (125 MHz, CDCl3, δC): 156.0, 155.0, 154.1, 152.4, 151.3, 147.7, 139.2, 136.1, 134.5, 133.3, 133.1, 131.3, 129.4, 128.2, 127.1, 125.6, 119.3, 117.8, 111.0, 110.8, 108.2, 107.4, 75.0, 69.0, 67.6, 56.9, 53.2, 50.7, 46.8, 29.0, 19.9, 11.5. HRMS (ESI) calcd for C33H35Cl2FN10O4: 725.2282; found 725.2281. HPLC Purity: 99.0%, tR=10.8 min.

4-(4-(4-(4-(((2S,4R)-2-((1H-imidazol-1-yl)methyl)-2-(2,4-dichlorophenyl)-1,3-dioxolan-4-yl)methoxy)phenyl)piperazin-1-yl)phenyl)-1-sec-butyl-1H-1,2,4-triazol-5(4H)-one (compound 33). 1H NMR (500 MHz, CDCl3, δH): 7.61 (s, 1H), 7.58 (d, J=8.0 Hz, 1H), 7.53 (bs, 1H), 7.46 (d, J=2.5 Hz, 1H), 7.42 (d, J=9.5 Hz, 2H), 7.26 (dd, J=8.2, 2.2 Hz, 2H), 7.03 (d, J=9 Hz, 2H), 7.00-6.98 (m, 1H), 6.93 (d, J=9.0 Hz, 2H), 6.78 (d, J=9.5 Hz, 2H), 4.51 (d, J=15.0 Hz, 1H), 4.41 (d, J=15.0 Hz, 1H), 4.41 (d, J=15.0 Hz, 1H), 4.34-4.28 (m, 2H), 3.87 (dd, J=8.5, 6.5 Hz, 1H), 3.74-3.72 (m, 2H), 3.36 (t, J=5.0 Hz, 4H), 3.32-3.31 (m, 1H), 3.23 (t, J=5.0 Hz, 4H), 1.89-1.83 (m, 1H), 1.74-1.71 (m, 1H), 1.39 (d, J=7.0 Hz, 3H), 0.90 (t, J=7.0 Hz, 3H). 13C NMR (125 MHz, CDCl3, δC): 152.7, 152.1, 150.6, 146.0, 136.0, 134.6, 134.0, 133.0, 131.4, 129.5, 127.3, 125.9, 123.6, 118.6, 116.7, 115.3, 108.0, 74.8, 67.7, 67.6, 52.7, 50.6, 49.3, 28.5, 19.3, 10.8. HRMS (ESI) calcd for C36H39Cl2N7O4: 704.2519; found 704.2525. HPLC Purity: 95.3%, tR=8.3 min.

4-(4-(4-(4-(((2S,4R)-2-((1H-pyrazol-1-yl)methyl)-2-(2,4-dichlorophenyl)-1,3-dioxolan-4-yl)methoxy)phenyl)piperazin-1-yl)phenyl)-1-sec-butyl-1H-1,2,4-triazol-5(4H)-one (compound 34). 1H NMR (500 MHz, CDCl3, δH): 7.62 (s, 1H), 7.58 (d, J=8.5 Hz, 1H), 7.49 (t, J=2.2 Hz, 2H), 7.45 (d, J=2.0 Hz, 1H), 7.43 (d, J=9.0 Hz, 2H), 7.22 (dd, J=9.5, 2.0 Hz, 1H), 7.03 (d, J=9.5 Hz, 2H), 6.93 (d, J=8.5 Hz, 2H), 6.77 (d, J=9.0 Hz, 2H), 6.22 (t, J=2.0 Hz, 1H), 4.79 (d, J=14.5 Hz, 1H), 4.68 (d, J=15.0 Hz, 1H), 4.36-4.33 (m, 1H), 4.31-4.27 (m, 1H), 3.87 (dd, J=8.5, 6.5 Hz, 1H), 3.80 (dd, J=8.5, 4.5 Hz, 1H), 3.77 (dd, J=8.5, 5.0 Hz, 1H), 3.37-3.31 (m, 5H), 3.24 (bs, 4H), 1.90-1.84 (m, 1H), 1.74-1.70 (m, 1H), 1.39 (d, J=6.5 Hz, 3H), 0.90 (t, J=7.2 Hz, 3H). 13C NMR (125 MHz, CDCl3, δC): 152.1, 139.4, 135.6, 135.0, 134.0, 133.2, 133.3, 131.2, 129.7, 127.1, 123.6, 118.5, 116.7, 115.3, 108.5, 105.8, 74.6, 68.0, 67.6, 56.1, 52.7, 50.7, 49.3, 28.5, 19.3, 10.8. HRMS (ESI) calcd for C36H39Cl2N7O4: 704.2519; found 704.2542. HPLC Purity: 95.9%, tR=11.6 min.

1-sec-butyl-4-(4-(4-(4-(((2S,4R)-2-(2,4-dichlorophenyl)-2-((2-methyl-1H-imidazol-1-yl)methyl)-1,3-dioxolan-4-yl)methoxy)phenyl)piperazin-1-yl)phenyl)-1H-1,2,4-triazol-5(4H)-one (compound 35). 1H NMR (500 MHz, CDCl3, δH): 7.63 (d, J=8.5 Hz, 1H), 7.61 (s, 1H), 7.47 (d, J=2.0 Hz, 1H), 7.42 (d, J=9.0 Hz, 2H), 7.29 (dd, J=8.5, 2.0 Hz, 1H), 7.03 (d, J=9.0 Hz, 2H), 6.94-6.90 (m, 3H), 6.77 (d, J=9.5 Hz, 2H), 4.41 (d, J=15.0 Hz, 1H), 4.34 (d, J=15.0 Hz, 1H), 4.32-4.26 (m, 2H), 3.85 (dd, J=8.5, 6.5 Hz, 1H), 3.76-3.73 (m, 1H), 3.66 (dd, J=9.5, 5.0 Hz, 1H), 3.36 (t, J=4.5 Hz, 4H), 3.24-3.22 (m, 5H), 2.49 (s, 3H), 1.89-1.84 (m, 1H), 1.74-1.69 (m, 1H), 1.39 (d, J=6.5 Hz, 3H), 0.90 (t, J=7.5 Hz, 3H). 13C NMR (125 MHz, CDCl3, δC): 152.7, 152.1, 150.6, 146.0, 136.0, 134.0, 133.1, 131.6, 129.6, 127.3, 125.9, 123.6, 118.5, 116.7, 115.3, 108.6, 74.8, 67.6, 67.4, 52.7, 50.6, 49.3, 43.2, 28.5, 19.3, 10.8. HRMS (ESI) calcd for C37H41Cl2N7O4: 718.2675; found 718.2645. HPLC Purity: 95.0%, tR=5.3 min.

1-sec-butyl-4-(4-(4-(4-(((2S,4R)-2-(2,4-dichlorophenyl)-2-((4-methyl-1H-imidazol-1-yl)methyl)-1,3-dioxolan-4-yl)methoxy)phenyl)piperazin-1-yl)phenyl)-1H-1,2,4-triazol-5(4H)-one (compound 38). 1H NMR (500 MHz, CDCl3, δH): 7.61 (s, 1H), 7.58 (d, J=8.5 Hz, 1H), 7.49 (bs, 1H), 7.46 (d, J=2.0 Hz, 1H), 7.42 (d, J=9.0 Hz, 2H), 7.27-7.25 (m, 1H), 7.03 (d, J=9.0 Hz, 2H), 6.94 (dd, J=9.0, 2.0 Hz, 2H), 6.78 (d, J=9.0 Hz, 2H), 6.69 (bs, 1H), 4.43 (d, J=15.0 Hz, 1H), 4.34 (d, J=15.0 Hz, 1H), 4.33-4.27 (m, 2H), 3.86 (dd, J=8.5, 6.5 Hz, 1H), 3.79 (dd, J=8.5, 4.5 Hz, 1H), 3.71 (dd, J=9.5, 5.0 Hz, 1H), 3.36 (t, J=4.5 Hz, 4H), 3.29 (dd, J=9.5, 6.5 Hz, 1H), 3.23 (t, J=5.0 Hz, 4H), 2.18 (s, 3H), 1.89-1.83 (m, 1H), 1.74-1.69 (m, 1H), 1.39 (d, J=6.5 Hz, 3H), 0.90 (t, J=7.5 Hz, 3H). 13C NMR (125 MHz, CDCl3, δC): 152.7, 152.1, 150.6, 146.0, 136.0, 134.6, 134.0, 133.0, 131.4, 129.6, 127.3, 125.9, 123.6, 118.5, 116.7, 115.2, 108.0, 74.8, 67.7, 67.5, 52.7, 51.4, 50.7, 49.3, 28.5, 19.3, 10.8. HRMS (ESI) calcd for C37H41Cl2N7O4: 718.2675; found 718.2697. HPLC Purity: 95.7%, tR=5.3 min.

1-(sec-butyl)-4-(4-(4-(4-(((2S,4R)-2-(2,4-dichlorophenyl)-2-((2-methyl-4-(trifluoromethyl)-1H-imidazol-1-yl)methyl)-1,3-dioxolan-4-yl)methoxy)phenyl)piperazin-1-yl)phenyl)-1H-1,2,4-triazol-5(4H)-one (compound 39). 1H NMR (500 MHz, CDCl3, δH): 7.64 (d, J=8.5 Hz, 2H), 7.61 (s, 1H), 7.48 (d, J=1.5 Hz, 1H), 7.42 (d, J=9 Hz, 2H), 7.31-7.29 (m, 2H), 7.03 (d, J=9 Hz, 2H), 6.93 (d, J=9 Hz, 2H), 6.75 (d, J=9 Hz, 2H), 4.44-4.41 (m, 1H), 4.37-4.26 (m, 3H), 3.85 (t, J=8.5 Hz, 1H), 3.78-3.76 (m, 1H), 3.65 (q, J=4.5 Hz, 1H), 3.32-3.38 (m, 4H), 3.40-3.20 (m, 4H), 2.48 (s, 3H), 1.90-1.84 (m, 1H), 1.75-1.69 (m, 1H), 1.40 (d, J=6.5 Hz, 3H), 0.91 (t, J=7.5 Hz, 3H). 13C NMR (125 MHz, CDCl3, δC): 152.7, 152.1, 150.6, 146.0, 136.1, 134.5, 133.0, 132.0, 129.6, 127.2, 125.9, 123.6, 121.9, 118.6, 116.5, 107.2, 74.7, 67.8, 52.7, 50.8, 49.3, 28.5, 19.3, 14.1, 10.8. HRMS (ESI) calcd for C38H40Cl2F3N7O4: 786.2549; found 786.2562. HPLC Purity: 95.7%, tR=11.9 min.

1-(sec-butyl)-4-(4-(4-(4-(((2S,4R)-2-(2,4-dichlorophenyl)-2-((2,4-dimethyl-1H-imidazol-1-yl)methyl)-1,3-dioxolan-4-yl)methoxy)phenyl)piperazin-1-yl)phenyl)-1H-1,2,4-triazol-5(4H)-one (compound 40). 1H NMR (500 MHz, CDCl3, δH): 7.65 (d, J=8.5 Hz, 1H), 7.61 (s, 1H), 7.43-7.40 (m, 3H), 7.24 (s, 1H), 7.03 (d, J=8.5 Hz, 2H), 6.89 (d, J=8.5 Hz, 2H), 6.73 (s, 1H), 6.66 (d, J=8.5 Hz, 2H), 4.35-4.24 (m, 3H), 4.18-4.15 (m, 1H), 3.94 (t, J=7.5 Hz, 1H), 3.89-3.86 (m, 1H), 3.82-3.79 (m, 1H), 3.75 (t, J=7.5 Hz, 1H), 3.33-3.37 (m, 4H), 3.20-3.22 (m, 4H), 2.50 (s, 3H), 2.20 (s, 3H), 1.90-1.82 (m, 1H), 1.75-1.70 (m, 1H), 1.40 (d, J=6.5 Hz, 3H), 0.91 (t, J=7.5 Hz, 3H). 13C NMR (125 MHz, CDCl3, δC): 152.6, 152.0, 150.2, 146.9, 136.2, 143.0, 134.1, 133.8, 131.2, 129.6, 127.2, 125.5, 122.5, 118.2, 117.5, 115.2, 108.2, 75.3, 67.9, 67.4, 52.5, 50.7, 49.4, 28.7, 15.6, 14.2, 10.8. HRMS (ESI) calcd for C38H43Cl2N7O4: 732.2832; found 732.2803. HPLC Purity: 94.8%, tR=5.0 min.

1-(sec-butyl)-4-(4-(4-(4-(((2S,4R)-2-(2,4-dichlorophenyl)-2-((2,5-dimethyl-1H-imidazol-1-yl)methyl)-1,3-dioxolan-4-yl)methoxy)phenyl)piperazin-1-yl)phenyl)-1H-1,2,4-triazol-5(4H)-one (compound 41). 1H NMR (500 MHz, CDCl3, δH): 7.73 (d, J=8.5 Hz, 1H), 7.61 (s, 1H), 7.45-7.41 (m, 3H), 7.24 (s, 1H), 7.03 (d, J=8.5 Hz, 2H), 6.89 (d, J=8.5 Hz, 2H), 6.67-6.65 (m, 3H), 4.33-4.27 (m, 2H), 4.24-4.21 (m, 1H), 4.02-3.98 (m, 1H), 3.85-3.84 (m, J=4.5 Hz, 1H), 3.81-3.76 (m, 2H), 3.72 (t, J=1.5 Hz, 1H), 3.37-3.34 (m, 4H), 3.24-3.20 (m, 4H), 2.51 (s, 3H), 2.30 (s, 3H), 1.90-1.85 (m, 1H), 1.75-1.70 (m, 1H), 1.41 (d, J=6.5 Hz, 3H), 0.93 (t, J=7.5 Hz, 3H). 13C NMR (125 MHz, CDCl3, δC): 152.7, 152.0, 150.2, 146.9, 136.2, 142.7, 134.1, 133.8, 131.2, 128.0, 127.2, 125.5, 122.0, 118.2, 117.5, 115.2, 108.2, 75.3, 67.9, 67.4, 52.5, 50.7 49.7, 28.7, 14.0, 10.8. HRMS (ESI) calcd for C38H43Cl2N7O4: 732.2832; found 732.2837. HPLC Purity: 95.0%, tR=5.2 min.

1-(sec-butyl)-4-(4-(4-(4-(((2S,4R)-2-(2,4-dichlorophenyl)-2-((2-ethyl-1H-imidazol-1-yl)methyl)-1,3-dioxolan-4-yl)methoxy)phenyl)piperazin-1-yl)phenyl)-1H-1,2,4-triazol-5(4H)-one (compound 43). 7.65 (d, J=8.5 Hz, 1H), 7.62 (s, 1H), 7.48 (d, J=2 Hz, 1H), 7.43 (d, J=9.0 Hz, 2H), 7.30 (dd, J=8.5, 2.0 Hz, 1H), 7.04 (d, J=9 Hz, 2H), 6.95-6.92 (m, 4H), 6.77 (d, J=9.0 Hz, 2H), 4.51 (d, J=15.0 Hz, 1H), 4.44 (d, J=15.0 Hz, 1H), 4.38 (d, J=15.0 Hz, 1H), 4.35-4.27 (m, 2H), 3.86 (dd, J=8.5, 6.5 Hz, 1H), 3.76 (dd, J=8.5, 4.5 Hz, 1H), 3.65 (dd, J=9.5, 5.2 Hz, 1H), 3.37 (t, J=5.0 Hz, 4H), 3.24 (t, J=5.0 Hz, 4H), 3.15 (t, J=8.5 Hz, 1H), 2.8 (q, J=7.5 Hz, 2H), 1.90-1.84 (m, 1H), 1.75-1.70 (m, 1H), 1.41 (d, J=6.5 Hz, 3H), 1.34 (3t, J=7.5 Hz, 3H), 0.91 (t, J=7.5 Hz, 3H). 13C NMR (125 MHz, CDCl3, δC): 153.2, 152.6, 151.3, 151.1, 146.4, 136.5, 135.7, 133.8, 132.1, 130.2, 128.0, 127.2, 126.6, 124.3, 122.3, 119.2, 117.4, 116.0, 109.5, 75.9, 68.7, 68.6, 53.9, 51.9, 50.8, 50.5, 29.9, 21.5, 20.8, 13.4, 12.4. HRMS (ESI) calcd for C38H43Cl2N7O4: 732.2832; found 732.2855. HPLC Purity: 98.2%, tR=5.6 min.

1-sec-butyl-4-(4-(4-(4-(((2S,4R)-2-(2,4-dichlorophenyl)-2-((2-isopropyl-1H-imidazol-1-yl)methyl)-1,3-dioxolan-4-yl)methoxy)phenyl)piperazin-1-yl)phenyl)-1H-1,2,4-triazol-5(4H)-one (compound 45). 1H NMR (500 MHz, CDCl3, δH): 7.63 (d, J=8.5 Hz, 1H), 7.61 (s, 1H), 7.48 (d, J=2.5 Hz, 1H), 7.42 (d, J=9.0 Hz, 2H), 7.29 (dd, J=8.5, 2.0 Hz, 1H), 7.03 (d, J=9 Hz, 2H), 6.97 (bs, 1H), 6.94 (s, 1H), 6.93-6.92 (m, 2H), 6.75 (d, J=9.0 Hz, 2H), 4.51 (d, J=15.0 Hz, 1H), 4.44 (d, J=15.0 Hz, 1H), 4.38 (d, J=15.0 Hz, 1H), 4.35-4.27 (m, 2H), 3.85 (dd, J=8.5, 6.5 Hz, 1H), 3.76 (dd, J=8.5, 4.5 Hz, 1H), 3.66 (dd, J=9.5, 5.2 Hz, 1H), 3.36 (t, J=5.2 Hz, 4H), 3.26 (t, J=7.0 Hz, 1H), 3.23 (t, J=5.0 Hz, 4H), 1.89-1.83 (m, 1H), 1.74-1.69 (m, 1H), 1.39 (d, J=6.5 Hz, 3H), 1.34 (d, J=7.0 Hz, 3H), 1.31 (d, J=6.5 Hz, 3H), 0.90 (t, J=7.5 Hz, 3H). 13C NMR (125 MHz, CDCl3, δC): 154.4, 152.6, 152.0, 150.6, 146.0, 136.0, 133.9, 133.1, 131.5, 129.6, 127.4, 125.9, 123.6, 121.3, 118.5, 116.7, 115.2, 108.3, 74.8, 67.6, 67.6, 52.7, 50.6, 49.3, 28.5, 25.5, 22.0, 21.6, 19.3, 10.8. HRMS (ESI) calcd for C39H45Cl2N7O4: 746.2988; found 746.2996. HPLC Purity: 95.8%, tR=6.0 min.

1-sec-butyl-4-(4-(4-(4-(((2S,4R)-2-(2,4-dichlorophenyl)-2-((2-phenyl-1H-imidazol-1-yl)methyl)-1,3-dioxolan-4-yl)methoxy)phenyl)piperazin-1-yl)phenyl)-1H-1,2,4-triazol-5(4H)-one (compound 46). 1H NMR (500 MHz, CDCl3, δH): 7.61 (s, 2H), 7.60 (d, J=3.5 Hz, 1H), 7.51 (d, J=8.5 Hz, 1H), 7.43-7.40 (m, 5H), 7.30 (d, J=2.5 Hz, 1H), 7.25 (d, J=1.5 Hz, 1H), 7.22 (dd, J=8.5, 2.5 Hz, 1H), 7.13 (s, 1H), 7.03 (d, J=9.5 Hz, 2H), 6.94 (d, J=9.5 Hz, 2H), 6.79 (d, J=9.5 Hz, 2H), 4.56 (s, 2H), 4.38-4.27 (m, 2H), 3.89-3.87 (m, 2H), 3.80 (dd, J=9.5, 5.0 Hz, 1H), 3.50 (dd, J=9.5, 6.5 Hz, 1H), 3.37-3.34 (m, 5H), 3.23 (t, J=5.5 Hz, 4H), 3.20-3.19 (m, 1H), 1.88-1.83 (m, 1H), 1.74-1.70 (m, 1H), 1.39 (d, J=6.5 Hz, 3H), 0.90 (t, J=7.5 Hz, 3H). 13C NMR (125 MHz, CDCl3, δC): 152.6, 152.0, 150.6, 146.0, 133.9, 131.4, 129.6, 129.5, 128.5, 127.1, 125.9, 123.6, 123.0, 118.9, 116.0, 115.3, 108.4, 74.7, 67.9, 67.3, 52.7, 50.6, 49.3, 28.5, 19.3, 10.8. HRMS (ESI) calcd for C42H43Cl2N7O4: 780.2832; found 780.2819. HPLC Purity: 95.6%, tR=6.5 min.

1-sec-butyl-4-(4-(4-(4-(((2S,4R)-2-(2,4-dichlorophenyl)-2-((3,5-dimethyl-1H-1,2,4-triazol-1-yl)methyl)-1,3-dioxolan-4-yl)methoxy)phenyl)piperazin-1-yl)phenyl)-1H-1,2,4-triazol-5(4H)-one (compound 47). 1H NMR (500 MHz, CDCl3, δH): 7.67 (d, J=8.5 Hz, 1H), 7.61 (s, 1H), 7.47 (d, J=2.0 Hz, 1H), 7.43 (d, J=9.0 Hz, 2H), 7.29 (dd, J=8.5, 2.0 Hz, 1H), 7.03 (d, J=9.5 Hz, 2H), 6.97 (d, J=9.5 Hz, 2H), 6.77 (dd, J=7.0, 2.5 Hz, 2H), 4.64 (d, J=15.0 Hz, 1H), 4.54 (d, J=15.0 Hz, 1H), 4.36 (dt, J=6.5, 5.0, 2.0 Hz, 1H), 4.29 (qt, J=8.5, 6.5, 4.0 Hz, 1H), 3.84 (t, J=5.0 Hz, 1H), 3.67 (dd, J=5.0, 6.5 Hz, 1H), 3.39 (t, J=5.0 Hz, 4H), 3.29-3.38 (m, 1H), 3.24 (t, J=5.0 Hz, 4H), 2.51 (s, 3H), 2.30 (s, 3H), 1.89-1.83 (m, 1H), 1.74-1.69 (m, 1H), 1.39 (d, J=6.5 Hz, 3H), 0.90 (t, J=7.5 Hz, 3H). 13C NMR (125 MHz, CDCl3, δC): 159.0, 154.5, 152.1, 150.5, 136.0, 134.7, 134.0, 133.1, 131.4, 129.8, 127.3, 127.1, 126.0, 123.6, 123.6, 118.7, 116.8, 116.2, 115.2, 108.6, 74.6, 67.6, 67.3, 52.7, 51.9, 50.8, 49.2, 28.5, 19.3, 13.7, 10.8. HRMS (ESI) calcd for C37H42Cl2N8O4: 733.2784; found 733.2764. HPLC Purity: 95.4%, tR=7.9 min.

4-(4-(4-(4-(((2S,4R)-2-((1H-tetrazol-1-yl)methyl)-2-(2,4-dichlorophenyl)-1,3-dioxolan-4-yl)methoxy)phenyl)piperazin-1-yl)phenyl)-1-sec-butyl-1H-1,2,4-triazol-5(4H)-one (compound 48). 1H NMR (500 MHz, CDCl3, δH): 8.46 (s, 1H), 7.61 (s, 1H), 7.55 (d, J=8.5 Hz, 1H), 7.48 (d, J=2.0 Hz, 1H), 7.43 (d, J=9 Hz), 7.24 (dd, J=8.5, 2.0 Hz, 1H), 7.03 (d, J=9.0 Hz, 2H), 6.81 (d, J=9.0 Hz, 2H), 5.36 (d, J=14.0 Hz, 1H), 5.27 (d, J=14.0 Hz, 1H), 4.38 (t, J=5.0 Hz, 1H), 4.31-4.27 (m, 1H), 3.95 (dd, J=8.5, 6.5 Hz, 1H), 3.88-3.83 (m, 2H), 3.53 (dd, J=9.5, 6.5 Hz, 1H), 3.38 (bs, 4H), 3.26 (bs, 4H), 1.89-1.83 (m, 1H), 1.74-1.69 (m, 1H), 1.39 (d, J=7.0 Hz, 3H), 0.90 (t, J=7.5 Hz, 3H). 13C NMR (125 MHz, CDCl3, δC): 162.5, 152.8, 152.7, 152.0, 136.3, 133.9, 133.3, 131.5, 130.1, 129.6, 127.2, 123.6, 116.8, 115.4, 107.4, 74.8, 67.9, 67.6, 56.6, 52.7, 36.5, 31.0, 28.5, 19.2, 10.8. HRMS (ESI) calcd for C34H37Cl2N9O4: 706.2424; found 706.2425. HPLC Purity: 95.9%, tR=10.8 min.

4-(4-(4-(4-(((2S,4R)-2-((2H-tetrazol-2-yl)methyl)-2-(2,4-dichlorophenyl)-1,3-dioxolan-4-yl)methoxy)phenyl)piperazin-1-yl)phenyl)-1-sec-butyl-1H-1,2,4-triazol-5(4H)-one (compound 49). 1H NMR (500 MHz, CDCl3, δH): 8.79 (s, 1H), 7.99 (s, 1H), 7.61 (s, 1H), 7.58 (d, J=8.5 Hz, 1H), 7.48 (d, J=2.0 Hz, 1H), 7.42-7.40 (m, 2H), 7.28-7.26 (m, 1H), 7.01 (d, J=9.0 Hz, 2H), 6.79 (d, J=9.0 Hz, 2H), 5.03 (d, J=4.0 Hz, 2H), 4.34 (t, J=9.0 Hz, 1H), 4.29-4.25 (m, 1H), 3.91 (dd, J=8.5, 7.0 Hz, 1H), 3.77-3.74 (m, 2H), 3.56 (dd, J=10.0, 5.5 Hz, 1H), 3.35 (bs, 4H), 3.23 (d, J=5.0 Hz, 4H), 1.88-1.82 (m, 1H), 1.73-1.67 (m, 1H), 1.37 (d, J=7.0 Hz, 3H), 0.88 (t, J=7.5 Hz, 3H). 13C NMR (125 MHz, CDCl3, δC): 162.9, 151.9, 151.7, 151.5, 136.3, 133.9, 133.9, 131.5, 131.0, 129.6, 126.9, 123.4, 116.6, 115.4, 107.4, 74.8, 67.9, 67.6, 56.6, 52.7, 36.5, 31.2, 28.5, 19.2, 10.7. HRMS (ESI) calcd for C34H37Cl2N9O4: 706.2424; found 706.2425. HPLC Purity: 94.6%, tR=10.4 min.

1-sec-butyl-4-(4-(4-(4-(((2S,4R)-2-(2,4-dichlorophenyl)-2-((3-methyl-1H-1,2,4-triazol-1-yl)methyl)-1,3-dioxolan-4-yl)methoxy)phenyl)piperazin-1-yl)phenyl)-1H-1,2,4-triazol-5(4H)-one (compound 50). 1H NMR (500 MHz, CDCl3, δH): 8.08 (bs, 1H), 7.62 (s, 1H), 7.60 (s, 1H), 7.46 (d, J=2.0 Hz, 1H), 7.43 (d, J=9.0 Hz, 2H), 7.26 (dd, J=8.0, 2.0 Hz, 1H), 7.03 (d, J=9.5 Hz, 2H), 6.98-6.97 (m, 2H), 6.80 (d, J=9.0 Hz, 2H), 4.75 (d, J=15.0 Hz, 1H), 4.65 (d, J=15.0 Hz, 1H), 4.36 (dt, J=6.5, 5.0, 2.5 Hz, 1H), 4.29 (dd, J=8.5, 6.5 Hz, 1H), 3.90 (dd, J=8.5, 6.5 Hz, 1H), 3.83 (dd, J=8.5, 4.5 Hz, 1H), 3.77 (dd, J=9.5, 5.0 Hz, 1H), 3.43 (dd, J=9.5, 6.5 Hz, 1H), 3.39 (m, 4H), 3.25 (t, J=5.0 Hz, 4H), 2.35 (s, 3H), 1.89-1.83 (m, 1H), 1.74-1.69 (m, 1H), 1.39 (d, J=6.5 Hz, 3H), 0.90 (t, J=7.5 Hz, 3H). 13C NMR (125 MHz, CDCl3, δC): 152.1, 145.3, 136.0, 134.3, 134.0, 133.2, 131.5, 129.7, 127.3, 123.7, 123.6, 118.7, 116.8, 115.3, 107.7, 74.7, 67.7, 67.5, 53.3, 52.7, 50.9, 49.2, 28.5, 19.3, 13.9, 10.8. HRMS (ESI) calcd for C36H40Cl2N8O4: 719.2628; found 719.2614. HPLC Purity: 97.4%, tR=9.2 min.

1-sec-butyl-4-(4-(4-(4-(((2S,4R)-2-(2,4-dichlorophenyl)-2-((3-(trifluoromethyl)-1H-1,2,4-triazol-1-yl)methyl)-1,3-dioxolan-4-yl)methoxy)phenyl)piperazin-1-yl)phenyl)-1H-1,2,4-triazol-5(4H)-one (compound 51). 1H NMR (500 MHz, CDCl3, δH): 8.32 (s, 1H), 7.62 (bs, 1H), 7.60 (s, 1H), 7.49 (d, J=2.0 Hz, 1H), 7.43 (d, J=8.5 Hz, 2H), 7.29 (dd, J=8.5, 2.0 Hz, 1H), 7.03 (d, J=9.0 Hz, 2H), 6.94-6.91 (m, 2H), 6.79 (d, J=8.0 Hz, 2H), 4.87 (d, J=15.0 Hz, 1H), 4.80 (d, J=15.0 Hz, 1H), 4.37 (t, J=5.0 Hz, 1H), 4.29 (dd, J=8.5, 6.5, 2.0 Hz, 1H), 3.93 (dd, J=8.5, 7.0 Hz, 1H), 3.82 (dd, J=8.5, 5.0 Hz, 1H), 3.80 (dd, J=10.0, 4.5 Hz, 1H), 3.49 (dd, J=9.5, 6.0 Hz, 1H), 3.37 (bs, 4H), 3.25 (bs, 4H), 1.89-1.83 (m, 1H), 1.74-1.69 (m, 1H), 1.39 (d, J=7.0 Hz, 3H), 0.90 (t, J=7.5 Hz, 3H). 13C NMR (125 MHz, CDCl3, δC): 162.6, 152.1, 146.6, 136.3, 134.0, 133.6, 133.2, 131.5, 129.7, 127.4, 123.6, 116.7, 115.2, 107.2, 74.7, 67.4, 67.4, 54.1, 52.7, 49.2, 36.5, 28.5, 19.3, 10.8. HRMS (ESI) calcd for C36H37Cl2F3N8O4: 773.2345; found 773.2357. HPLC Purity: 95.5%, tR=12.2 min.

1-sec-butyl-4-(4-(4-(4-(((2S,4R)-2-(2,4-dichlorophenyl)-2-((5-methyl-1H-tetrazol-1-yl)methyl)-1,3-dioxolan-4-yl)methoxy)phenyl)piperazin-1-yl)phenyl)-1H-1,2,4-triazol-5(4H)-one (compound 52). 1H NMR (500 MHz, CDCl3, δH): 7.61 (s, 1H), 7.59 (d, J=8.5 Hz, 1H), 7.48 (d, J=2.0 Hz, 1H), 7.43 (d, J=9 Hz, 2H), 7.26 (dd, J=8.0, 2.5 Hz, 1H), 7.03 (d, J=9.0 Hz, 2H), 6.80 (d, J=8.5 Hz, 2H), 5.27 (d, J=14.5 Hz, 1H), 5.15 (d, J=14.5 Hz, 1H), 4.39 (dt, J=6.5, 5.0, 1.5 Hz, 1H), 4.31-4.27 (m, 1H), 3.95-3.87 (m, 2H), 3.80 (dd, J=9.5, 4.7 Hz, 1H), 3.76 (dd, J=9.0, 7.0 Hz, 1H), 3.38 (bs, 4H), 3.27 (bs, 4H), 2.47 (s, 3H), 1.89-1.83 (m, 1H), 1.74-1.69 (m, 1H), 1.39 (d, J=7.0 Hz, 3H), 0.90 (t, J=7.5 Hz, 3H). 13C NMR (125 MHz, CDCl3, δC): 171.2, 162.9, 152.1, 133.9, 133.5, 131.5, 129.6, 127.2, 123.6, 117.7, 115.4, 107.5, 74.7, 67.9, 67.5, 60.4, 56.4, 52.7, 28.5, 21.1, 19.3, 14.2, 10.8. HRMS (ESI) calcd for C35H39Cl2N9O4: 720.2580; found 720.2571. HPLC Purity: 94.8%, tR=11.3 min.

1-sec-butyl-4-(4-(4-(4-(((2S,4R)-2-(2,4-dichlorophenyl)-2-((5-phenyl-1H-tetrazol-1-yl)methyl)-1,3-dioxolan-4-yl)methoxy)phenyl)piperazin-1-yl)phenyl)-1H-1,2,4-triazol-5(4H)-one (compound 53). 1H NMR (500 MHz, CDCl3, δH): 8.15-8.13 (m, 2H), 8.02 (bs, 1H), 7.63-7.59 (m, 2H), 7.50 (d, J=2.5 Hz, 1H), 7.48-7.46 (m, 2H), 7.44-7.41 (m, 2H), 7.26 (dd, J=8.5, 2.0 Hz, 1H), 7.03 (d, J=9.0 Hz, 2H), 6.67 (d, J=9.0 Hz, 2H), 5.35 (d, J=14.5 Hz, 1H), 5.24 (d, J=14.5 Hz, 1H), 4.41-4.34 (m, 1H), 4.29 (dd, J=9.0, 6.5 Hz, 1H), 3.94 (dd, J=9.0, 6.5 Hz, 1H), 3.88 (dd, J=8.5, 4.5 Hz, 1H), 3.81 (dd, J=9.5, 4.5 Hz, 1H), 3.44 (dd, J=9.5, 6.5 Hz, 1H), 3.35 (bs, 4H), 3.20 (bs, 4H), 1.89-1.83 (m, 1H), 1.75-1.69 (m, 1H), 1.39 (d, J=6.5 Hz, 3H), 0.90 (t, J=7.5 Hz, 3H). 13C NMR (125 MHz, CDCl3, δC): 196.5, 133.9, 133.4, 131.5, 129.7, 128.9, 127.0, 123.6, 118.4, 115.3, 107.5, 57.4, 56.7, 52.7, 32.2, 28.5, 19.3, 10.8. HRMS (ESI) calcd for C40H41Cl2N9O4: 782.2737; found 782.2749. HPLC Purity: 95.7%, tR=13.7 min.

4-(4-(4-(4-(((2S,4R)-2-(bromomethyl)-2-(2,4-dichlorophenyl)-1,3-dioxolan-4-yl)methoxy)phenyl)piperazin-1-yl)phenyl)-1-sec-butyl-1H-1,2,4-triazol-5(4H)-one (compound 57). 1H NMR (500 MHz, CDCl3, δH): 7.65 (d, J=8.5 Hz, 1H), 7.61 (s, 1H), 7.43-7.42 (m, 3H), 7.27 (dd, J=8.5, 2.0 Hz, 1H), 7.03 (d, J=9.0 Hz, 2H), 6.95 (bs, 2H), 6.90 (d, J=9.0 Hz, 2H), 4.46-4.42 (m, 1H), 4.31-4.27 (m, 1H), 4.22 (dd, J=9.5, 5.0 Hz, 1H), 4.14 (dd, J=8.5, 5.5 Hz, 1H), 4.09 (dd, J=8.5, 6.5 Hz, 1H), 4.02 (dd, J=8.5, 7.0 Hz, 1H), 3.96 (d, J=11.5 Hz, 1H), 3.86 (d, J=11.5 Hz, 1H), 3.37 (bs, 4H), 3.25 (bs, 4H), 1.89-1.84 (m, 1H), 1.75-1.69 (m, 1H), 1.39 (d, J=7.0 Hz, 3H), 0.90 (t, J=7.5 Hz, 3H). 13C NMR (125 MHz, CDCl3, δC): 152.1, 135.7, 134.7, 133.9, 133.0, 131.3, 120.0, 127.0, 123.6, 118.5, 116.7, 115.5, 107.8, 74.8, 68.6, 68.4, 52.7, 50.7, 49.3, 35.4, 28.5, 19.3, 10.8. HRMS (ESI) calcd for C33H36BrCl2N5O4: 716.1406; found 716.1422. HPLC Purity: 95.7%, tR=13.3 min.

1-sec-butyl-4-(4-(4-(4-(((2R,4R)-2-(2,4-dichlorophenyl)-2-ethyl-1,3-dioxolan-4-yl)methoxy)phenyl)piperazin-1-yl)phenyl)-1H-1,2,4-triazol-5(4H)-one (compound 59). 1H NMR (500 MHz, CDCl3, δH): 7.61 (s, 1H), 7.57 (d, J=8.0 Hz, 1H), 7.43 (d, J=9.0 Hz, 2H), 7.40 (d, J=2.0 Hz, 1H), 7.23 (dd, J=8.5, 2.0 Hz, 1H), 7.03 (d, J=9.0 Hz, 2H), 6.95 (bs, 2H), 6.89 (d, J=9.0 Hz, 2H), 4.33-4.27 (m, 2H), 4.12 (dd, J=9.5, 5.0 Hz, 1H), 3.98 (dd, J=8.5, 4.5 Hz, 1H), 3.96 (dd, J=9.5, 6.5 Hz, 1H), 3.86 (dd, J=8.5, 7.0 Hz, 1H), 3.37 (bs, 4H), 3.24 (bs, 4H), 2.18-2.09 (m, 2H), 1.89-1.83 (m, 1H), 1.75-1.69 (m, 1H), 1.39 (d, J=7.0 Hz, 3H), 0.90 (t, J=7.5 Hz, 3H), 0.89 (t, J=7.0 Hz, 3H). 13C NMR (125 MHz, CDCl3, δC): 152.1, 137.4, 134.5, 133.9, 132.8, 131.2, 129.8, 126.8, 123.6, 118.5, 116.7, 115.2, 111.2, 73.7, 69.3, 67.1, 52.7, 50.7, 49.3, 30.7, 28.5, 19.3, 10.8, 7.7. HRMS (ESI) calcd for C34H39Cl2N5O4: 652.2457; found 652.2426. HPLC Purity: 95.0%, tR=13.4 min.

4-(4-(4-(4-(((2R,4R)-2-benzyl-2-(2,4-dichlorophenyl)-1, 3-dioxolan-4-yl)methoxy)phenyl)piperazin-1-yl)phenyl)-1-sec-butyl-1H-1,2,4-triazol-5(4H)-one (compound 60). 1H NMR (500 MHz, CDCl3, δH): 7.62 (s, 1H), 7.46-7.42 (m, 4H), 7.43-7.42 (m, 3H), 7.22 (bs, 5H), 7.16 (dd, J=8.5, 2.0 Hz, 1H), 7.03 (d, J=9.0 Hz, 2H), 6.93 (bs, 2H), 6.73 (d, J=9.0 Hz, 2H), 4.32-4.26 (m, 2H), 3.79-3.77 (m, 2H), 3.68 (dd, J=9.5, 5.0 Hz, 1H), 3.45 (d, J=14.0, 1H), 3.37 (bs, 4H), 3.34 (d, J=14.0 Hz, 1H), 3.32-3.28 (m, 1H), 3.25 (bs, 4H), 1.89-1.84 (m, 1H), 1.75-1.69 (m, 1H), 1.39 (d, J=6.5 Hz, 3H), 0.90 (t, J=7.2 Hz, 3H). 13C NMR (125 MHz, CDCl3, δC): 152.1, 137.7, 135.2, 134.6, 133.9, 132.9, 131.3, 131.1, 129.5, 127.7, 123.6, 116.7, 115.3, 110.1, 74.0, 68.4, 67.2, 52.7, 49.2, 43.7, 36.5 28.5, 19.3, 10.8. HRMS (ESI) calcd for C39H41Cl2N5O4: 714.2614; found 714.2590. HPLC Purity: 95.1%, tR=14.8 min.

1-sec-butyl-4-(4-(4-(4-(((2R,4R)-2-(cyclopentylmethyl)-2-(2,4-dichlorophenyl)-1,3-dioxolan-4-yl)methoxy)phenyl)piperazin-1-yl)phenyl)-1H-1,2,4-triazol-5(4H)-one (compound 61). 1H NMR (500 MHz, CDCl3, δH): 7.62 (s, 1H), 7.58 (d, J=8.0 Hz, 1H), 7.43 (d, J=9.0 Hz, 2H), 7.39 (d, J=2.5 Hz, 1H), 7.22 (dd, J=8.5, 2.0 Hz, 1H), 7.03 (d, J=9.0 Hz, 2H), 6.95 (bs, 2H), 6.89 (d, J=9.0 Hz, 2H), 4.31-4.27 (m, 2H), 4.12 (dd, J=9.2, 4.5 Hz, 1H), 3.99-3.95 (m, 2H), 3.84 (dd, J=8.0, 7.0 Hz, 1H), 3.37 (bs, 4H), 3.24 (bs, 4H), 2.24-2.16 (m, 2H), 1.90-1.81 (m, 2H), 1.75-1.69 (m, 3H), 1.57-1.53 (m, 2H), 1.44-1.41 (m, 2H), 1.39 (d, J=7.0 Hz, 3H), 1.14-1.06 (m, 2H), 0.90 (t, J=7.5 Hz, 3H). 13C NMR (125 MHz, CDCl3, δC): 152.1, 137.8, 134.5, 133.9, 133.0, 131.2, 129.8, 126.6, 123.6, 118.5, 116.7, 115.5, 111.1, 73.6, 69.1, 66.8, 52.7, 50.7, 49.3, 43.6, 35.4, 33.6, 33.5, 28.5, 25.1, 25.0, 19.3, 10.8. HRMS (ESI) calcd for C38H45Cl2N5O4: 706.2927; found 706.2915. HPLC Purity: 95.4%, tR=15.2 min.

1-sec-butyl-4-(4-(4-(4-(((4R)-2-(2,4-dichlorophenyl)-1, 3-dioxolan-4-yl)methoxy)phenyl)piperazin-1-yl)phenyl)-1H-1,2,4-triazol-5(4H)-one (Mixture of trans and cis) (compound 62). Trans compound: 1H NMR (500 MHz, CDCl3, δH): 7.62 (s, 1H), 7.57 (d, J=8.5 Hz, 1H), 7.43 (d, J=8.5 Hz, 2H), 7.40 (t, J=2.0 Hz, 1H), 7.28 (t, J=2.0 Hz, 1H), 7.27 (bs, 1H), 7.03 (d, J=9.0 Hz, 2H), 6.95 (bs, 1H), 6.92-6.88 (m, 2H), 6.27 (s, 1H), 4.66-4.60 (m, 1H), 4.34 (dd, J=8.2, 6.7 Hz, 1H), 4.31-4.27 (m, 1H), 4.18-4.15 (m, 1H), 4.14-4.07 (m, 1H), 4.03 (dd, J=8.5, 6.5 Hz, 1H), 3.37 (bs, 4H), 3.25 (bs, 4H), 1.90-1.84 (m, 1H), 1.75-1.69 (m, 1H), 1.39 (d, J=6.5 Hz, 3H), 0.91 (t, J=7.2 Hz, 3H). 13C NMR (125 MHz, CDCl3, δC): 152.1, 135.8, 135.7, 134.4, 134.3, 133.9, 129.6, 128.8, 127.4, 127.2, 123.6, 118.5, 116.7, 115.5, 100.7, 76.5, 74.7, 68.7, 68.6, 67.9, 52.7, 50.7, 28.5, 19.3, 10.8. Cis compound: 1H NMR (500 MHz, CDCl3, δH): 7.62 (s, 1H), 7.57 (d, J=8.5 Hz, 1H), 7.43 (d, J=8.5 Hz, 2H), 7.40 (t, J=2.0 Hz, 1H), 7.29 (d, J=2.0 Hz, 1H), 7.27 (bs, 1H), 7.03 (d, J=9.0 Hz, 2H), 6.95 (bs, 1H), 6.92-6.88 (m, 2H), 6.16 (s, 1H), 4.66-4.60 (m, 1H), 4.31-4.27 (m, 1H), 4.21 (dd, J=8.2, 6.7 Hz, 1H), 4.18-4.15 (m, 1H), 4.14-4.07 (m, 1H), 4.03 (dd, J=8.5, 6.5 Hz, 1H), 3.37 (bs, 4H), 3.25 (bs, 4H), 1.90-1.84 (m, 1H), 1.75-1.69 (m, 1H), 1.39 (d, J=6.5 Hz, 3H), 0.91 (t, J=7.2 Hz, 3H). 13C NMR (125 MHz, CDCl3, δC): 152.1, 135.8, 135.7, 134.4, 134.3, 133.9, 129.6, 128.8, 127.4, 127.2, 123.6, 118.5, 116.7, 115.5, 100.7, 76.5, 74.7, 68.7, 68.6, 67.9, 52.7, 50.7, 28.5, 19.3, 10.8. HRMS (ESI) calcd for C32H35Cl2N5O4: 624.2144; found 624.2114. HPLC Purity: 95.9%, tR=13.7 min.

1-(sec-butyl)-4-(4-(4-(4-(((2S,4R)-2-(2,4-dichlorophenyl)-2-(morpholinomethyl)-1,3-dioxolan-4-yl)methoxy)phenyl)piperazin-1-yl)phenyl)-1H-1,2,4-triazol-5(4H)-one (compound 63). 1H NMR (500 MHz, CDCl3, δH): 7.63 (s, 1H), 7.61 (d, J=9.0 Hz, 1H), 7.45 (d, J=8.5 Hz, 2H), 7.41 (d, J=1.5 Hz, 1H), 7.25 (dd, J=8, 1.5 Hz, 1H), 7.06 (d, J=9.0 Hz, 2H), 6.98 (d, J=9.0 Hz, 2H), 6.92 (d, J=8.5 Hz, 2H), 4.36-4.41 (m, 1H), 4.28-3.34 (m, 1H), 4.14-4.18 (m, 1H), 4.05-4.10 (m, 2H), 3.89 (t, J=7.0 Hz, 1H), 3.57 (t, J=4 Hz, 4H), 3.36-3.40 (m, 4H), 3.26 (t, J=5 Hz, 4H), 2.59 (t, J=4 Hz, 4H), 1.95-1.85 (m, 1H), 1.79-1.70 (m, 1H), 1.42 (d, J=7 Hz, 3H), 0.93 (t, J=7 Hz, 3H). 13C NMR (125 MHz, CDCl3, δC): 152.6, 151.1, 146.5, 135.3, 133.6, 131.6, 130.6, 127.2, 126.6, 124.3, 119.3, 117.5, 116.2, 75.2, 68.4, 56.0, 53.9, 51.9, 50.5, 31.1, 29.9, 20.8, 12.4. HRMS (ESI) calcd mass for C37H44Cl2N6O5: 723.2828; found 723.2826. HPLC Purity: 96.2%, tR=5.0 min.

1-(sec-butyl)-4-(4-(4-(4-(((2S,4R)-2-(2,4-dichlorophenyl)-2-((dimethylamino)methyl)-1,3-dioxolan-4-yl)methoxy)phenyl)piperazin-1-yl)phenyl)-1H-1,2,4-triazol-5(4H)-one (compound 64). 1H NMR (500 MHz, CDCl3, δH): 8.41 (s, 1H), 7.74-7.75 (m, 2H), 7.59 (d, J=9 Hz, 2H), 7.19 (d, J=9 Hz, 2H), 7.06 (d, J=9 Hz, 2H), 7.00 (d, J=9 Hz, 2H), 4.53-4.48 (m, 1H), 4.23-4.18 (m, 3H), 4.10-4.03 (m, 4H), 3.43-3.38 (m, 4H), 3.27-3.24 (m, 4H), 2.59 (s, 6H), 1.84-1.78 (m, 1H), 1.76-1.70 (m, 1H), 1.38 (d, J=6.5 Hz, 3H), 0.88 (t, J=6.5 Hz, 3H). 13C NM R (125 MHz, CDCl3, δC): 152.8, 150.2, 146.5, 135.5, 134.2, 130.2, 127.0, 126.6, 124.3, 119.3, 117.5, 116.2, 77.2, 72.2, 68.4, 60.7, 50.4, 47.6, 29.9, 20.8, 12.4. HRMS (ESI) calcd for C36H40Cl2N8O4: 681.2723; found 681.2714. HPLC Purity: 97.1%, tR=4.7 min.

1-(sec-butyl)-4-(4-(4-(4-(((2S,4R)-2-(2,4-dichlorophenyl)-2-((4-methylpiperazin-1-yl)methyl)-1,3-dioxolan-4-yl)methoxy)phenyl)piperazin-1-yl)phenyl)-1H-1,2,4-triazol-5(4H)-one (compound 65). 1H NMR (500 MHz, CDCl3, δH): 8.03 (s, 1H), 7.62 (s, 1H), 7.58 (d, J=8.5 Hz, 1H), 7.43 (d, J=7.5 Hz, 2H), 7.38 (s, 1H), 7.23 (d, J=8.5 Hz, 1H), 7.04 (d, J=8 Hz, 2H), 6.96 (d, J=8 Hz, 2H), 6.90 (d, J=8 Hz, 2H), 4.36-4.34 (m, 1H), 4.32-4.28 (m, 1H), 4.15-4.12 (m, 1H), 4.06-4.02 (m, 2H), 3.87 (t, J=7.5 Hz, 1H), 3.60-3.58 (m, 4H), 3.37-3.36 (m, 4H), 3.25-3.22 (m, 4H), 3.02 (s, 2H), 2.70-2.67 (m, 4H), 2.33 (s, 3H), 1.89-1.84 (m, 1H), 1.75-1.69 (m, 1H), 1.41 (d, J=6.5 Hz, 3H), 0.91 (t, J=7.5 Hz, 3H). 13C NM R (125 MHz, CDCl3, δC): 153.5, 152.6, 151.1, 146.5, 137.4, 135.2, 133.7, 131.6, 130.6, 127.2, 126.6, 124.3, 119.3, 117.5, 116.2, 75.2, 70.1, 68.2, 63.6, 55.8, 54.3, 53.9, 51.9, 50.5, 46.7, 29.9, 20.8, 12.4. HRMS (ESI) calcd for C38H47Cl2N7O4: 736.7291; found 736.7252. HPLC Purity: 96.3%, tR=7.5 min.

1-(sec-butyl)-4-(4-(4-(4-(((2S,4R)-2-(2,4-dichlorophenyl)-2-(piperazin-1-ylmethyl)-1,3-dioxolan-4-yl)methoxy)phenyl)piperazin-1-yl)phenyl)-1H-1,2,4-triazol-5(4H)-one (compound 66). 1H NMR (500 MHz, CDCl3, δH): 7.62 (s, 1H), 7.60 (d, J=8.5 Hz, 2H), 7.44 (d, J=9 Hz, 2H), 7.39 (d, J=1.5 Hz, 1H), 7.24 (dd, J=8.5, 2.0 Hz, 1H), 7.04 (d, J=8.5 Hz, 2H), 6.96 (d, J=9 Hz, 2H), 6.90 (d, J=9 Hz, 2H), 4.39-4.34 (m, 1H), 4.32-4.27 (m, 1H), 4.16-4.13 (m, 1H), 4.08-4.03 (m, 2H), 3.89 (t, J=7.5 Hz, 1H), 3.56 (t, J=4.5 Hz, 4H), 3.39-3.35 (m, 4H), 3.26-3.23 (m, 4H), 2.99 (d, J=3 Hz, 3H), 2.57 (t, J=4.5 Hz, 4H), 2.19 (s, 1H), 1.90-1.85 (m, 1H), 1.76-1.70 (m, 1H), 1.41 (d, J=6.5 Hz, 3H), 0.92 (t, J=7.5 Hz, 3H). 13C NMR (125 MHz, CDCl3, δC): 153.5, 151.1, 146.5, 137.4, 135.2, 133.6, 131.6, 130.6, 127.2, 126.6, 124.3, 119.3, 117.5, 116.2, 75.2, 70.0, 68.4, 68.2, 64.4, 56.0, 53.9, 51.9, 50.5, 29.9, 20.8, 12.4. HRMS (ESI) calcd for C37H45Cl2N7O4: 722.7049; found 722.7043. HPLC Purity: 95.1%, tR=5.1 min.

4-(4-(4-(6-(((2S,4R)-2-((1H-1,2,4-triazol-1-yl)methyl)-2-(2,4-dichlorophenyl)-1,3-dioxolan-4-yl)methoxy)pyridin-3-yl)piperazin-1-yl)phenyl)-2-(sec-butyl)-2,4-dihydro-3H-1,2,4-triazol-3-one (compound 100). 1H NMR (500 MHz, CDCl3, δH): 8.12 (s, 1H), 7.76 (s, 1H), 7.74 (d, J=2.0 Hz, 1H), 7.51 (s, 1H), 7.45 (d, J=8.5 Hz, 1H) 7.35-7.29 (m, 4H), 7.12 (dd, J=8.0, 2.0 Hz, 1H), 6.97 (d, J=8.5 Hz, 2H), 6.67 (d, J=9.0 Hz, 1H), 4.71 (q, J=14.5 Hz, 2H), 4.29-4.25 (m, 1H), 4.20-4.15 (m, 1H), 4.13-4.09 (m, 1H), 4.04-4.00 (m, 1H), 3.81 (t, J=7.0 Hz, 1H), 3.65-3.61 (m, 1H), 3.31-3.29 (m, 4H), 3.20-3.15 (m, 4H), 1.78-1.71 (m, 1H), 1.65-1.56 (m, 1H), 1.29 (d, J=7.0 Hz, 3H), 0.79 (t, J=7.0 Hz, 3H). 13C NMR (125 MHz, CDCl3, δC): 158.3, 152.0, 151.3, 136.0, 134.9, 134.2, 133.8, 133.2, 131.4, 130.4, 129.7, 127.2, 123.6, 117.2, 111.3, 107.6, 74.8, 67.2, 64.9, 53.8, 52.8, 50.6, 49.3, 41.0, 28.5, 19.3, 10.8. HRMS (ESI) calcd for C34H37Cl2N9O4: 706.2424; found 706.2422. HPLC Purity: 98.2%, tR=10.7 min.

4-(4-(4-(5-(((2S,4R)-2-((1H-1,2,4-triazol-1-yl)methyl)-2-(2,4-dichlorophenyl)-1,3-dioxolan-4-yl)methoxy)pyridin-2-yl)piperazin-1-yl)phenyl)-2-(sec-butyl)-2,4-dihydro-3H-1,2,4-triazol-3-one (compound 101). 1H NMR (500 MHz, CDCl3, δH): 8.09 (s, 1H), 7.78 (s, 1H), 7.76 (d, J=3.0 Hz, 1H), 7.51 (s, 1H), 7.47 (d, J=8.5 Hz, 1H), 7.36 (d, J=2.0 Hz, 1H), 7.32 (d, J=9.0 Hz, 2H), 7.16 (dd, J=8.5, 2 Hz, 1H), 7.06 (dd, J=8.5, 2 Hz, 1H), 6.92 (d, J=9.0 Hz, 2H), 6.61 (d, J=9.0 Hz, 1H), 4.71 (q, J=14.5 Hz, 2H), 4.26-4.22 (m, 1H), 4.19-4.15 (m, 1H), 3.82-3.79 (m, 1H), 3.71-3.65 (m, 2H), 3.51 (t, J=5.5 Hz, 4H), 3.45-3.42 (m, 1H), 3.23 (t, J=5.5 Hz, 4H), 1.78-1.71 (m, 1H), 1.63-1.57 (m, 1H), 1.28 (d, J=6.5 Hz, 3H), 0.79 (t, J=6.5 Hz, 3H). 13C NMR (125 MHz, CDCl3, δC): 152.0, 151.4, 150.5, 147.9, 136.1, 134.0, 133.1, 131.5, 129.6, 127.3, 126.0, 123.6, 116.7, 107.7, 74.6, 68.5, 67.2, 53.6, 52.7, 48.9, 46.3, 41.0, 28.4, 19.28, 10.8. HRMS (ESI) calcd for C34H37Cl2N9O4: 706.2424; found 706.2415. HPLC Purity: 95.4%, tR=6.3 min.

4-(6-(4-(4-(((2S,4R)-2-((1H-1,2,4-triazol-1-yl)methyl)-2-(2,4-dichlorophenyl)-1,3-dioxolan-4-yl)methoxy)phenyl)piperazin-1-yl)pyridin-3-yl)-2-(sec-butyl)-2,4-dihydro-3H-1,2,4-triazol-3-one (compound 102). 1H NMR (500 MHz, CDCl3, δH): 8.27-8.26 (m, 2H), 7.91 (s, 1H), 7.75 (dd, J=8.5 Hz, 4 Hz, 1H), 8.60-8.57 (m, 2H), 7.48 (d, J=4.0 Hz, 1H), 7.28 (m, 1H), 6.98-6.96 (m, 2H), 6.82-6.76 (m, 3H), 4.85 (q, J=14.5 Hz, 2H), 4.39-4.26 (m, 2H), 3.94-3.90 (m, 1H), 3.82-3.75 (m, 7H), 3.50-3.46 (m, 1H), 3.21-3.18 (m, 4H), 1.90-1.81 (m, 1H), 1.77-1.68 (m, 1H), 1.41 (d, J=7.0 Hz, 3H), 0.91 (t, J=7.0 Hz, 3H). 13C NMR (125 MHz, CDCl3, δC): 158.3, 152.1, 142.3, 136.1, 134.1, 133.8, 133.1, 133.0, 131.4, 129.6, 127.3, 121.3, 118.7, 115.3, 107.6, 107.1, 74.7, 67.6, 53.7, 52.8, 50.6, 45.3, 41.0, 28.5, 19.3, 10.8. HRMS (ESI) calcd for C34H37Cl2N9O4: 706.2424; found 706.2417. HPLC Purity: 95.6%, tR=10.5 min.

4-(5-(4-(4-(((2S,4R)-2-((1H-1,2,4-triazol-1-yl)methyl)-2-(2,4-dichlorophenyl)-1,3-dioxolan-4-yl)methoxy)phenyl)piperazin-1-yl)pyridin-2-yl)-2-(sec-butyl)-2,4-dihydro-3H-1,2,4-triazol-3-one (compound 103). 1H NMR (500 MHz, CDCl3, δH): 8.35 (s, 1H), 8.27-8.20 (m, 2H), 8.10 (d, J=4.0 Hz, 1H), 7.80-7.95 (brs, 1H), 7.60 (dd, J=12.0 Hz, 1H), 7.48 (d, J=4.0 Hz, 1H), 7.42 (dd, J=8.0, 2.2 Hz, 1H), 7.28 (m, 1), 6.99 (d, J=8.0 Hz, 2H), 6.83 (d, J=8.0 Hz, 2H), 4.84 (q, J=14.5 Hz, 2H), 4.40-4.25 (m, 2H), 3.94-3.90 (m, 1H), 3.84-3.78 (m, 2H), 3.50-3.46 (m, 1H), 3.41-3.35 (m, 4H), 3.28-3.26 (m, 4H), 1.91-1.84 (m, 1H), 1.77-1.67 (m, 1H), 1.41 (d, J=7.0 Hz, 3H), 0.90 (t, J=7.0 Hz, 3H). 13C NMR (125 MHz, CDCl3, δC): 151.1, 145.7, 140.2, 136.1, 134.0, 133.1, 132.5, 131.5, 129.6, 127.3, 125.7, 118.7, 115.3, 113.7, 107.6, 74.7, 67.6, 53.6, 52.5, 50.7, 48.9, 28.4, 19.3, 10.8. HRMS (ESI) calcd for C34H37Cl2N9O4: 706.2424; found 706.2420. HPLC Purity: 98.2%, tR=10.6 min.

4-(4-(4-(4-(((2S,4R)-2-((1H-1,2,4-triazol-1-yl)methyl)-2-(2,4-dichlorophenyl)-1,3-dioxolan-4-yl)methoxy)phenyl)piperazin-1-yl)-3-fluorophenyl)-2-(sec-butyl)-2,4-dihydro-3H-1,2,4-triazol-3-one (compound 104). 1H NMR (500 MHz, CDCl3, δH): 8.12 (s, 1H), 7.79 (s, 1H), 7.67 (d, J=8.5 Hz, 1H), 7.53 (s, 1H), 7.47 (d, J=8.5 Hz, 1H), 7.36 (d, J=2.0 Hz, 1H), 7.29-7.26 (m, 1H), 7.20-7.13 (m, 2H), 6.95 (t, J=9.0 Hz, 2H), 6.71 (d, J=9.0 Hz, 2H), 4.73 (q, J=14.5 Hz, 2H), 4.28-4.23 (m, 1H), 4.19-4.15 (m, 1H), 3.80 (t, J=7.0 Hz, 1H), 3.72-3.66 (m, 2H), 3.40-3.36 (m, 1H), 3.26-3.14 (m, 8H), 1.77-1.69 (m, 1H), 1.64-1.56 (m, 1H), 1.28 (d, J=7.5 Hz, 3H), 0.78 (t, J=7.5 Hz, 3H). 13C NMR (125 MHz, CDCl3, δC): 156.4, 154.4, 151.7, 136.1, 134.0, 133.3, 133.2, 131.5, 130.1, 129.6, 128.1, 127.3, 119.5, 117.9, 115.4, 111.0, 110.8, 107.7, 74.7, 73.7, 67.7, 67.4, 53.7, 52.9, 41.0, 28.4, 19.3, 10.8. HRMS (ESI) calcd for C35H37Cl2FN8O4: 723.2377; found 723.2365. HPLC Purity: 99.0%, tR=10.3 min.

4-(4-(4-(6-(((2S,4R)-2-((1H-1,2,4-triazol-1-yl)methyl)-2-(2,4-dichlorophenyl)-1,3-dioxolan-4-yl)methoxy)pyridin-3-yl)piperazin-1-yl)-3-fluorophenyl)-2-(sec-butyl)-2,4-dihydro-3H-1,2,4-triazol-3-one (compound 105). 1H NMR (500 MHz, CDCl3, δH): 8.13 (s, 1H), 7.76-7.73 (m, 2H), 7.61 (d, J=0.5 Hz, 1H), 7.49 (d, J=8.0 Hz, 1H) 7.34-7.31 (m, 3H), 7.18-7.15 (m, 1H), 7.13 (dd, J=8.5 Hz, 2 Hz, 1H), 6.95 (t, J=9.0 Hz, 1H), 6.60 (d, J=9.0 Hz, 1H), 4.71 (q, J=14.5 Hz, 2H), 4.29-4.26 (m, 1H), 4.18-4.09 (m, 2H), 4.03-3.99 (m, 1H), 3.83-3.79 (m, 1H), 3.64-3.61 (m, 1H), 3.32-3.14 (m, 8H), 1.77-1.70 (m, 1H), 1.63-1.57 (m, 1H), 1.27 (d, J=7.0 Hz, 3H), 0.78 (t, J=7.0 Hz, 3H). 13C NMR (125 MHz, CDCl3, δC): 156.3, 154.3, 151.5, 145.4, 136.1, 135.8, 134.1, 133.3, 133.0, 132.3, 131.3, 130.0, 129.6, 129.5, 128.5, 127.9, 127.1, 119.5, 117.8, 111.1, 110.9, 110.7, 107.5, 74.77, 73.57, 69.3, 67.1, 66.7, 64.7, 61.6, 53.8, 52.7, 50.2, 40.7, 28.3, 19.2, 10.7. HRMS (ESI) calcd for C34H36Cl2FN9O4: 724.2330; found 724.2328. HPLC Purity: 95.3%, tR=11.2 min.

4-(4-(4-(5-(((2S,4R)-2-((1H-1,2,4-triazol-1-yl)methyl)-2-(2,4-dichlorophenyl)-1,3-dioxolan-4-yl)methoxy)pyridin-2-yl)piperazin-1-yl)-3-fluorophenyl)-2-(sec-butyl)-2,4-dihydro-3H-1,2,4-triazol-3-one (compound 106). 1H NMR (500 MHz, CDCl3, δH): 8.10 (s, 1H), 7.78 (s, 1H), 7.77 (d, J=3.0 Hz, 1H), 7.55 (s, 1H), 7.47 (d, J=8.0 Hz, 1H), 7.36 (d, J=2.0 Hz, 1H), 7.29 (dd, J=8.0, 2.5 Hz, 1H), 7.16-7.13 (m, 2H), 7.06 (dd, J=9.0, 3.0 Hz, 1H), 6.93 (t, J=9.0 Hz, 1H), 6.60 (d, J=9.0 Hz, 1H), 4.72 (q, J=14.5 Hz, 2H), 4.26-4.22 (m, 1H), 4.19-4.14 (m, 1H), 3.83-3.79 (m, 1H), 3.71-3.65 (m, 2H), 3.52 (t, J=5.5 Hz, 4H), 3.45-3.42 (m, 1H), 3.11 (t, J=5.5 Hz, 4H), 1.79-1.70 (m, 1H), 1.64-1.56 (m, 1H), 1.28 (d, J=7.0 Hz, 3H), 0.78 (t, J=7.0 Hz, 3H). 13C NMR (125 MHz, CDCl3, δC): 156.4, 154.4, 151.6, 151.4, 147.9, 139.3, 136.1, 133.9, 133.3, 133.1, 131.5, 129.6, 127.3, 119.5, 117.9, 111.0, 110.8, 108.5, 107.7, 74.6, 68.5, 67.2, 53.6, 52.8, 50.3, 46.5, 41.0, 28.4, 19.3, 10.8. HRMS (ESI) calcd for C34H36Cl2FN9O4: 724.2330; found 724.2326. HPLC Purity: 96.0%, tR=7.2 min.

Aqueous solubility test. In a 1.5 mL microcentrifuge tube, 2 ul of 10 mM compound stock solution in DMSO was added to 1 mL 0.001N HCl aqueous buffer to obtain saturated solution. The resulting mixture was shaken under 600 rpm for 24 h at room temperature. Then the tube was centrifuged at 13,000 rpm for 5 min to remove the undissolved compound. 100 ul of the supernatant was injected to an Agilent 6120 LC/MS for analysis. The mass spectrometry data was collected under SIM/Scan mode. The ions of compound Exact Mass+1 and Exact Mass+23 were monitored as selected ion monitoring (SIM) for peak area integration. Solubility was calculated according to the concentration standard curve of each compound.

HUVEC Culture and Proliferation Assays. HUVEC (Lonza) were grown in EGM-2 bullet kit media (Lonza) and used at passage eight or lower. The H thymidine incorporation assays were conducted as previously described. Briefly, cells were seeded on 96-well plate at a concentration of 2000 cells/well and allowed to settle overnight. Drugs were added to each well in triplicate. After 24 hours, cells were treated with 1 μCi of [3H] thymidine for 6 h. Then cells were harvested and transferred to filtermats. The scintillation were counted and IC50 were determined using Prism software (version 6.0).

CYP3A4 enzyme assay. CYP3A4 enzyme activity was tested using Vivid™ CYP3A4 Green Screening Kit (ThermoFisher, #P2857) using the manufacturer's protocol. Briefly, CYP3A4 baculosomes and drugs were incubated 10 min at 37° C. Then Vivid® Substrates were added and the fluorescence (ex/em:485/520) were read every 1 min for 60 minute.

Tube formation assay. A 24-well plate were coated with 250 ul matrigel (BD, #CB-40234C) per well. 70000 HUVEC were added to the plate with 500 μL media with different drugs. After 24 h, 2 uM calcein AM was added and incubated for 15 min. after replaced with new media, the tube network was photographed using fluorescent microscopy. The total tube length was calculated using image J.

Filipin staining. 2000 HUVECs were plated in chamber slide with 1 ml media and allowed to settle overnight. Cells were treated with 0.1 uM drug or DMSO for 14 hours. The the cells were fixed with 4% paraformaldehyde for 15 min. After washed, cells were incubated with 500 ul 50 ug/ml filipin solution for 1 hour in the dark. Then the cells were washed twice with PBS, mounted and covered with coverslip. The images were taken using confocal microscope under 360/460 nm.

Western blot. HUVEC cells were treated with different concentration of compound 48 for 24 hours. Then cells were lysed using RIPA buffer and the protein concentration were measured and normalized. After electrophoresis and transfer onto 0.45 um nitrocellulose membranes, the membranes were bolted with 5% BSA for 1 h and then incubated overnight at 4° C. Secondary antibody was applied to each membrane for 1 hour. Bolts were imaged using Syngene PXi imaging system after adding chemiluminescent substrate. The following antibodies were used for the assay: AMPKα (1:1,000, cell signaling, #2532s), phosphor-AMPKα (1:1,000, cell signaling #2535s), ACC (1:1,000, cell signaling #3662s), phosphor-ACC (1:1,000, cell signaling, #3661s), mTOR (1:1,000, cell signaling, #2972S), phosphor-mTOR (1:1,000, cell signaling, #9234s), p70 S6 Kinase (1:1,000, senta cruz, #sc-8418), phosphor-p70 S6 Kinase (1:1,000, cell signaling, #3662s), anti-Rabbit IgG (1:10000, GE lifesciences, #NA934V).

Immunofluorescence assay. HUVECs (5000) were seeded in 4-well chamber slide (Nunc™ Lab-Tek™ II) with 1 mL media and cultured overnight. Cells were treated with 2 M drugs or DMSO for 24 h. The media was then aspirated and washed 3 times with PBS. Cells were fixed with 4% paraformaldehyde for 15 min, washed three times with PBS, permeabilized with 0.1% Triton X and washed again. 2% BSA blocking buffer was applied to the cells for 1 h. The primary antibodies of VEGFR2 (1:50, cell signaling, #2479) and GM130 (1:1000, BD, #610823) were incubated overnight at 4° C. After washing 3 times with 0.5% BSA in PBS, secondary antibody solutions (1:1000 goat anti-rabbit Alexa Fluor 488, Invitrogen, #A11008 and 1:1000 goat anti-mouse Alexa Fluor 594, Invitrogen, A11005) were applied at room temperature for 1 h in the dark. After washing 3 times, slides were incubated in 0.1 μg/mL DAPI solution for 5 min and rinsed 2 times with PBS. The coverslip was mounted with Immunount (Fisher) and sealed with nail polish. Confocal images were taken using Zeiss LSM700 confocal microscope with 20× lenses.

Molecular docking. The binding mode of itraconazole and 17 to NPC1 (PDB: 5131) were simulated using AutoDock Vina3. The PDB structures for itraconazole and 17 were generated with Babel and pdbqt files of both protein and ligand were generated in AutoDock Tools. The grid box configuration was set as follows: center_x=28.5, center_y=51, center_z=44.5; size_x=24, size_y=24, size_z=22. PyMOL software was used to visualize the ligand-protein interactions.

Although the disclosure has been described with reference to the above examples, it will be understood that modifications and variations are encompassed within the spirit and scope of the disclosure. Accordingly, the disclosure is limited only by the following claims.

What is claimed is:

1. A compound having a structure according to Formula (I):

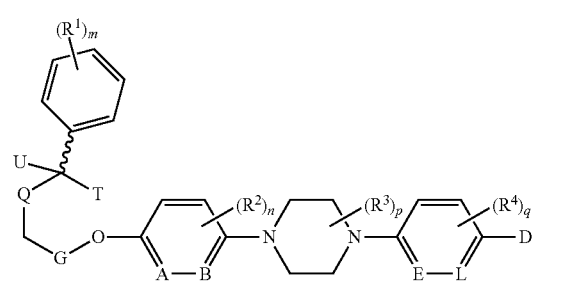

or an optically pure stereoisomer or pharmaceutically acceptable salt thereof,
wherein,
U is

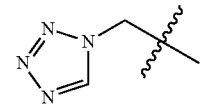 [SMILES: *Cn1cnnn1]

$R^1$, $R^2$, $R^3$, and $R^4$ are each independently selected from the group consisting of alkoxy, alkyl, alkynyl, amino, amido, halogen, hydroxyl, haloalkyl, perhaloalkyl, perhaloalkoxy, nitro, and cyano, wherein alkoxy, alkyl, and alkynyl are optionally substituted with halogen, hydroxyl, or nitro group;

A is $CR^5$ or N;
B is $CR^6$ or N;
E is $CR^7$ or N;
L is $CR^8$ or N;

R⁵, R⁶, R⁷, and R⁸ are each independently selected from the group consisting of hydrogen, alkoxy, alkyl, alkynyl, amino, halogen, hydroxyl, haloalkyl, perhaloalkyl, perhaloalkoxy, nitro, and cyano, wherein alkoxy, alkyl, and alkynyl are optionally substituted with halogen, hydroxyl, or nitro group;

G, Q, and T together with the atom(s) to which they are attached joined together to form dioxolane

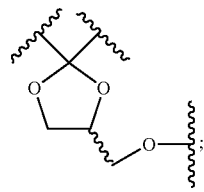 [SMILES: *OCC1COC(*)(*)O1]

m is an integer between 0 and 5;
n and q are each independently an integer between 0 and 2;
p is an integer between 0 and 4;
D is selected from the group consisting of:

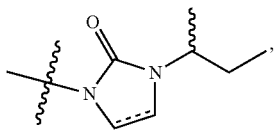

-continued

[structures with R¹⁰, I–J, and K–S(O)₂–NH groups]

wherein,
------- is a single or double bond;
R¹⁰ is selected from the group consisting of hydrogen, alkyl, arylalkyl, alkoxyalkyl, arylalkoxy, alkynylalkyl, alkylalkynylalkyl, alkenylalkyl, alkylalkenylalkyl, cycloalkyl, cyanoalkyl, cycloalkylalkyl, heteroalkyl, heterocycloalkyl, heteroaryl, heteroarylalkyl, heterocycloalkylalkyl, and alkylsulfonyl, any of which can be optionally substituted with halogen, hydroxyl, or nitro group;
I is (CH₂)r or NH;
J is (CH₂)s or NH;
K is (CH₂)t or NH; and
r, s, and t are each independently an integer between 0 and 4.

2. The compound of claim 1, selected from:

| Structure | Compound Number |
|---|---|
| [structure] | 8 |
| [structure] | 9 |
| [structure] | 10 |

| Structure | Compound Number |
|---|---|
| 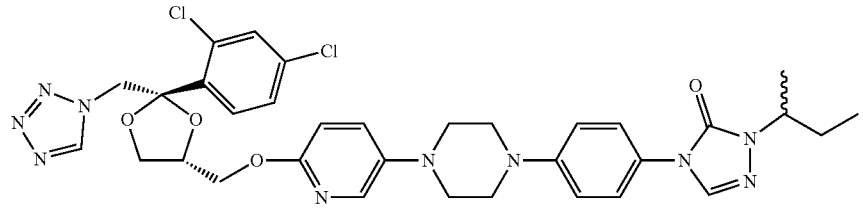 | 11 |
| 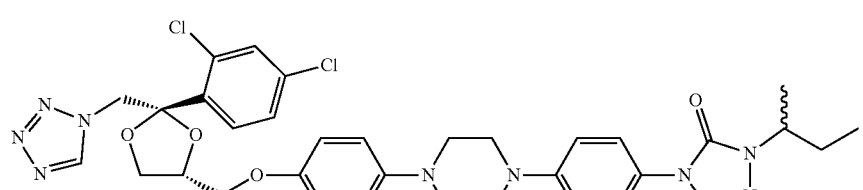 | 12 |
| 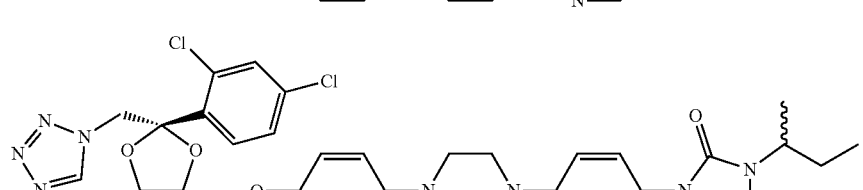 | 13 |
| 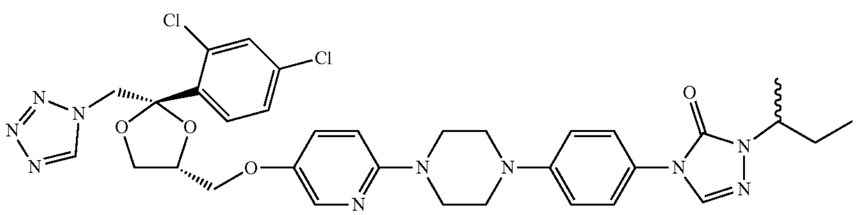 [SMILES: CCC(C)n1ncn(-c2ccc(N3CCN(c4cnc(OC[C@@H]5CO[C@@](Cn6cnnn6)(c6ccc(Cl)cc6Cl)O5)nc4)CC3)cc2)c1=O] | 14 |
| 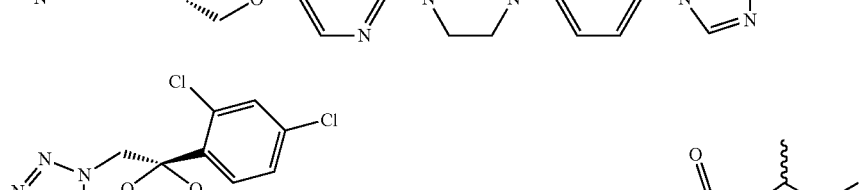 | 15 |
| 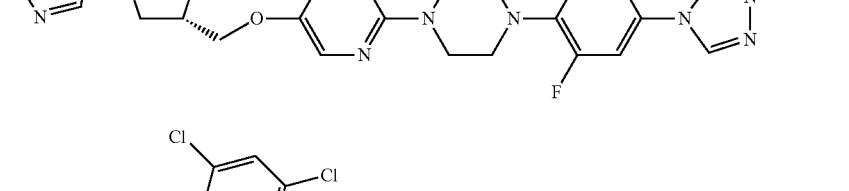 | 16 |
| 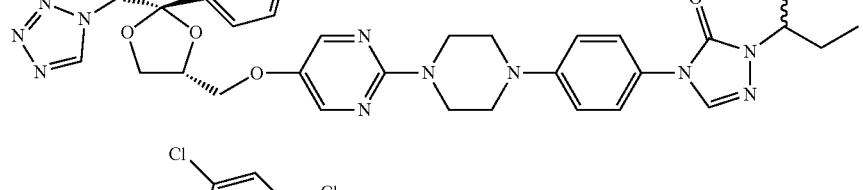 | 17 |

| Structure | Compound Number |
|---|---|
| 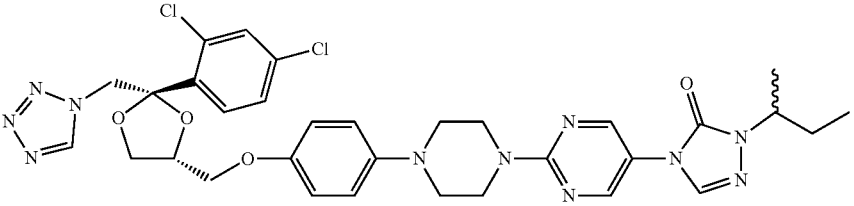 | 18 |
| 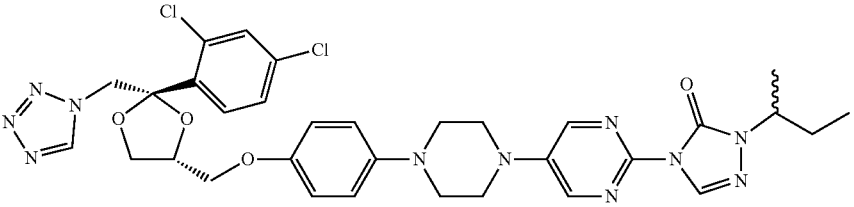 [SMILES: CCC(C)n1ncn(-c2cnc(N3CCN(c4ccc(OC[C@@H]5CO[C@@](Cn6cnnn6)(c6ccc(Cl)cc6Cl)O5)cc4)CC3)nc2)c1=O] | 19 |
| 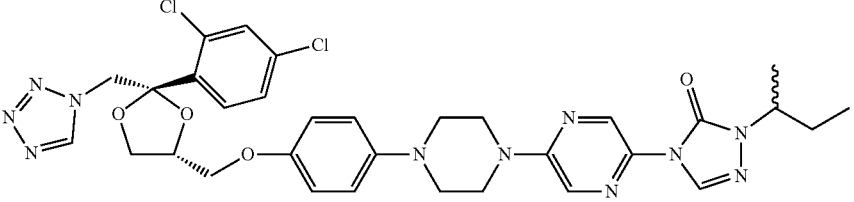 | 20 |
| 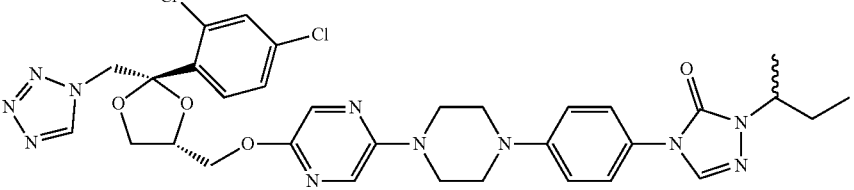 | 21 |
| 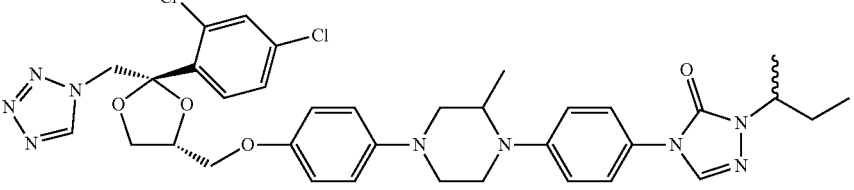 | 22 |
| 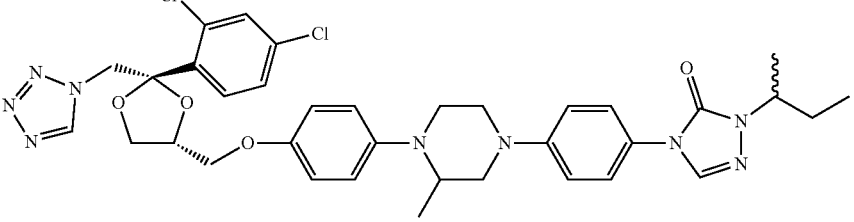 | 23 |
| 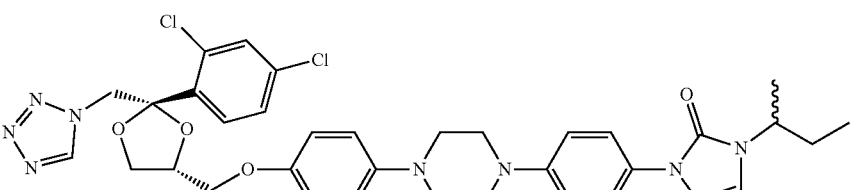 | 24 |

| Structure | Compound Number |
|---|---|
| 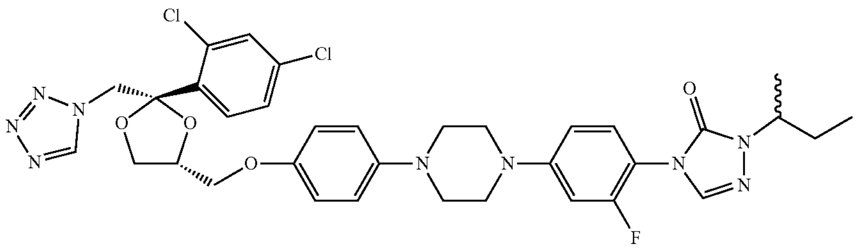 [SMILES: CCC(C)n1ncn(-c2ccc(N3CCN(c4ccc(OC[C@@H]5CO[C@@](Cn6cnnn6)(c6ccc(Cl)cc6Cl)O5)cc4)CC3)cc2F)c1=O] | 25 |
| 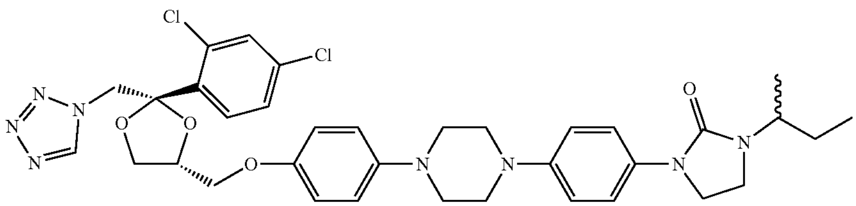 [SMILES: CCC(C)N1CCN(c2ccc(N3CCN(c4ccc(OC[C@@H]5CO[C@@](Cn6cnnn6)(c6ccc(Cl)cc6Cl)O5)cc4)CC3)cc2)C1=O] | 26 |
| 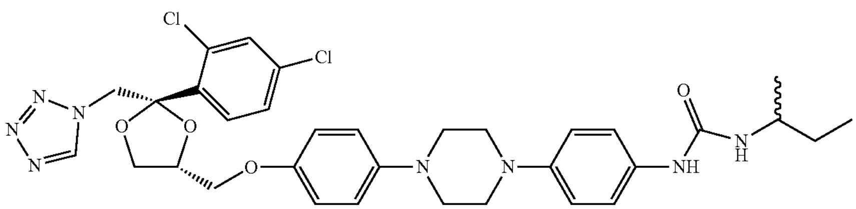 | 27 |
| 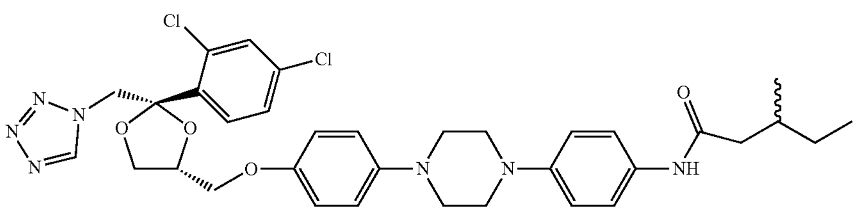 [SMILES: CCC(C)CC(=O)Nc1ccc(N2CCN(c3ccc(OC[C@@H]4CO[C@@](Cn5cnnn5)(c5ccc(Cl)cc5Cl)O4)cc3)CC2)cc1] | 28 |
| 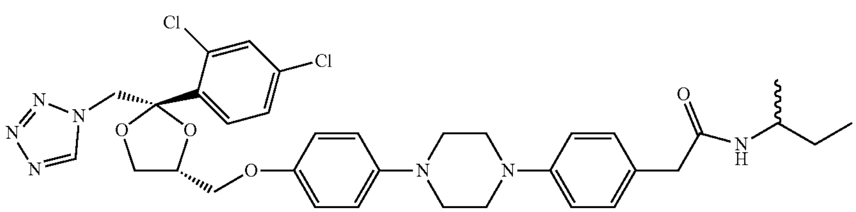 [SMILES: CCC(C)NC(=O)Cc1ccc(N2CCN(c3ccc(OC[C@@H]4CO[C@@](Cn5cnnn5)(c5ccc(Cl)cc5Cl)O4)cc3)CC2)cc1] | 29 |
| 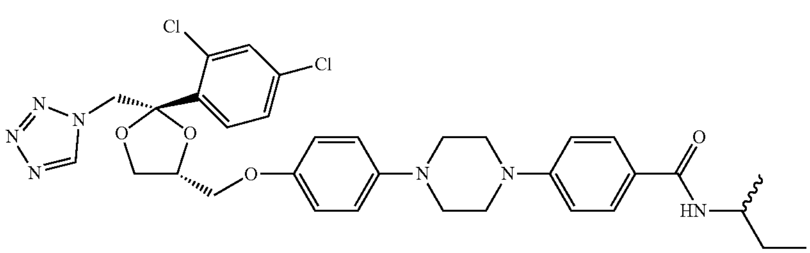 [SMILES: CCC(C)NC(=O)c1ccc(N2CCN(c3ccc(OC[C@@H]4CO[C@@](Cn5cnnn5)(c5ccc(Cl)cc5Cl)O4)cc3)CC2)cc1] | 30 |
| 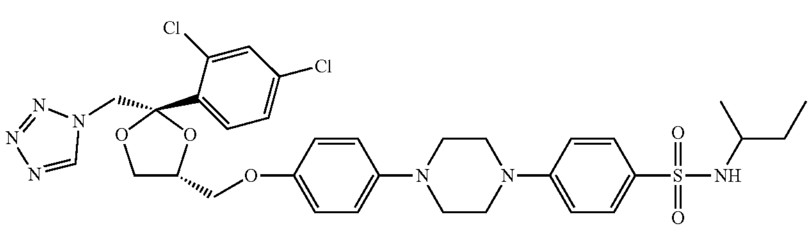 [SMILES: CCC(C)NS(=O)(=O)c1ccc(N2CCN(c3ccc(OC[C@@H]4CO[C@@](Cn5cnnn5)(c5ccc(Cl)cc5Cl)O4)cc3)CC2)cc1] | 31 |

-continued
| Structure | Compound Number |
|---|---|
| 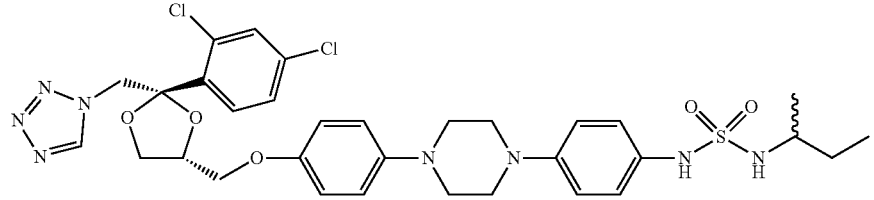 [SMILES: CCC(C)NS(=O)(=O)Nc1ccc(N2CCN(c3ccc(OC[C@@H]4CO[C@@](Cn5cnnn5)(c5ccc(Cl)cc5Cl)O4)cc3)CC2)cc1] | 32 |
| 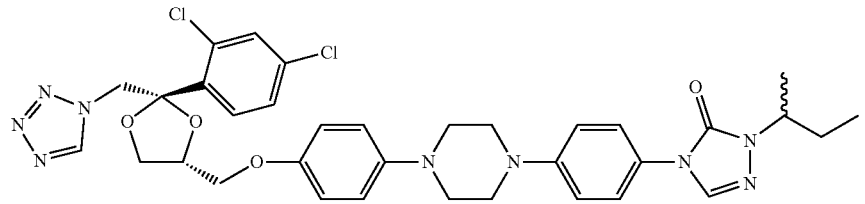 | 48 |
| 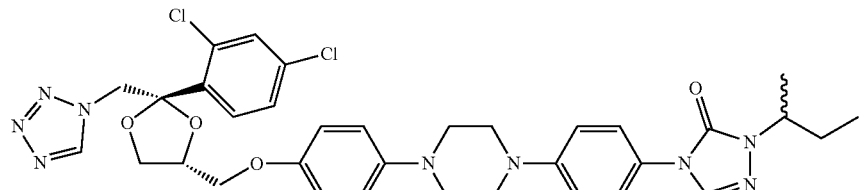 | 49 |
| 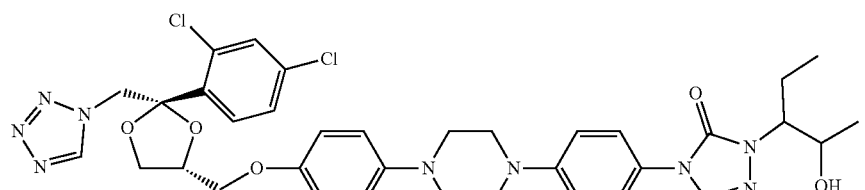 | 82 |
| 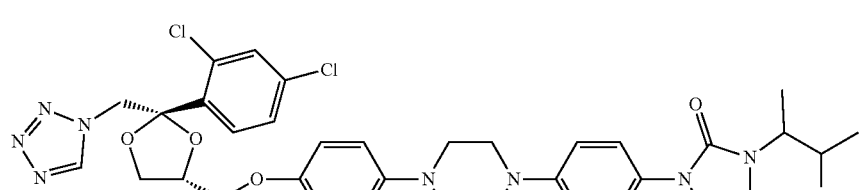 | 83 |
| 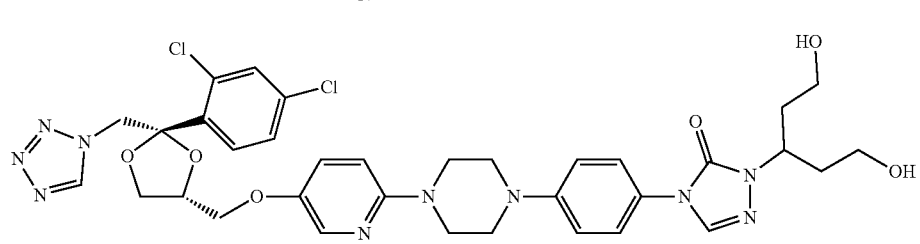 [SMILES: O=c1n(-c2ccc(N3CCN(c4ccc(OC[C@@H]5CO[C@@](Cn6cnnn6)(c6ccc(Cl)cc6Cl)O5)cn4)CC3)cc2)cnn1C(CCO)CCO] | 84 |
| 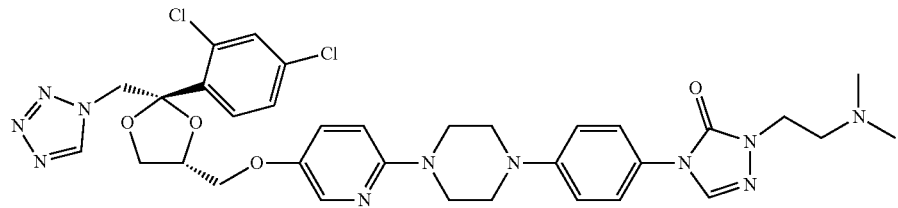 [SMILES: CN(C)CCn1ncn(-c2ccc(N3CCN(c4ccc(OC[C@@H]5CO[C@@](Cn6cnnn6)(c6ccc(Cl)cc6Cl)O5)cn4)CC3)cc2)c1=O] | 85 |

| Structure | Compound Number |
|---|---|
| 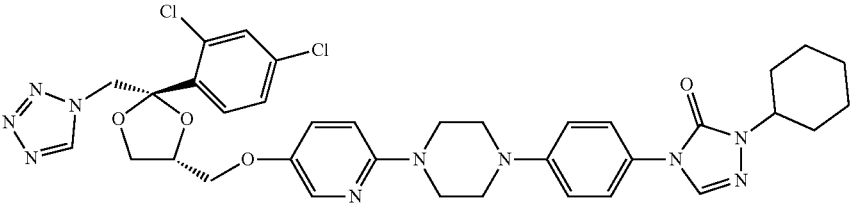 | 86 |
| 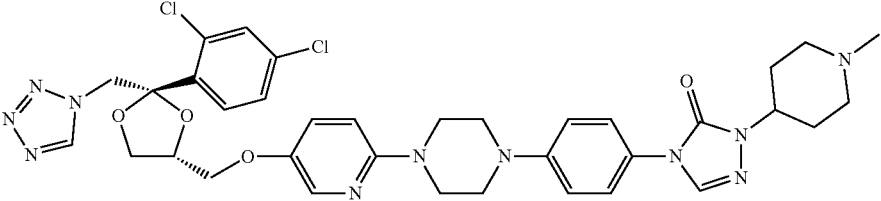 [SMILES: CN1CCC(n2ncn(-c3ccc(N4CCN(c5ccc(OC[C@@H]6CO[C@@](Cn7cnnn7)(c7ccc(Cl)cc7Cl)O6)cn5)CC4)cc3)c2=O)CC1] | 87 |
| 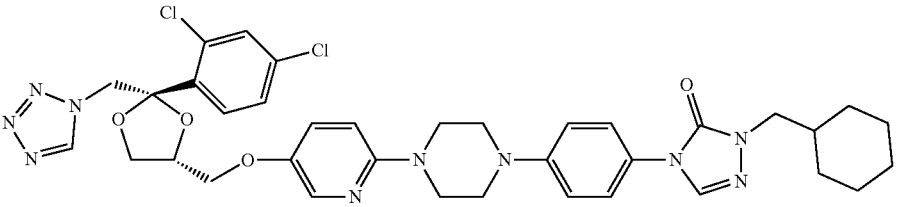 [SMILES: O=c1n(-c2ccc(N3CCN(c4ccc(OC[C@@H]5CO[C@@](Cn6cnnn6)(c6ccc(Cl)cc6Cl)O5)cn4)CC3)cc2)cnn1CC1CCCCC1] | 88 |
| 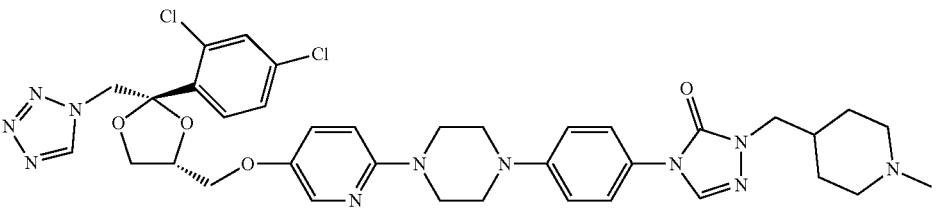 [SMILES: CN1CCC(Cn2ncn(-c3ccc(N4CCN(c5ccc(OC[C@@H]6CO[C@@](Cn7cnnn7)(c7ccc(Cl)cc7Cl)O6)cn5)CC4)cc3)c2=O)CC1] | 89 |
| 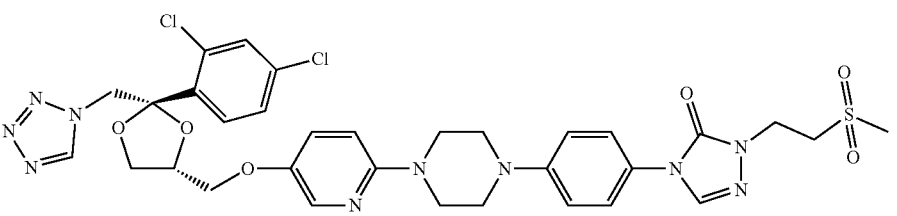 | 90 |
| 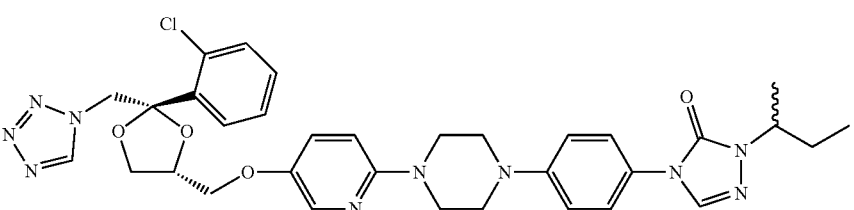 | 91 |
| 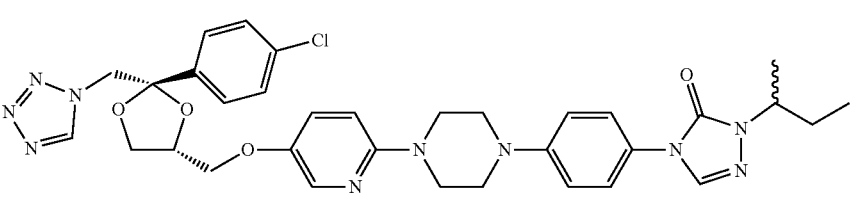 [SMILES: CCC(C)n1ncn(-c2ccc(N3CCN(c4ccc(OC[C@@H]5CO[C@@](Cn6cnnn6)(c6ccc(F)cc6)O5)cn4)CC3)cc2)c1=O] | 92 |

-continued

| Structure | Compound Number |
|---|---|
| (structure) | 93 |
| (structure) | 94 |
| (structure) | 95 |
| (structure) | 96 |
| (structure) | 97 |
| (structure) | 98 |
| (structure) | 107 |

| Structure | Compound Number |
|---|---|
| 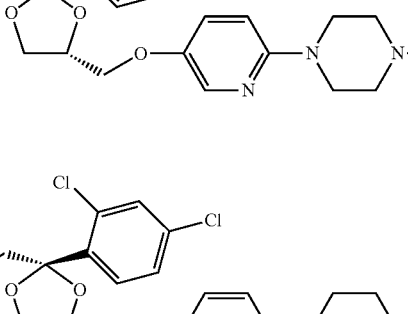 | 108 |
| 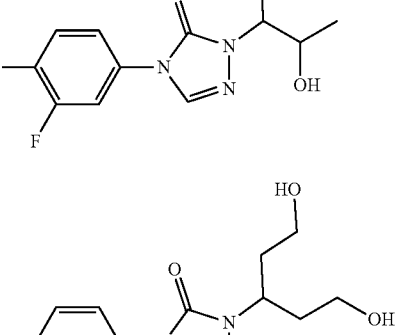 | 109 |
| 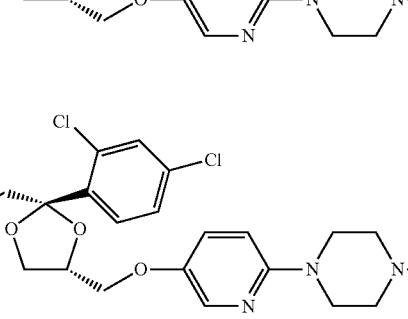 | 110 |
| 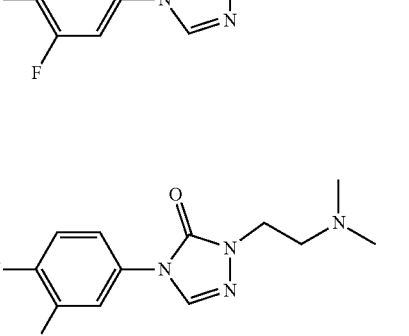 | 111 |
| 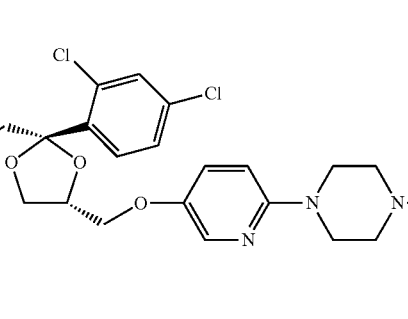 | 112 |
| 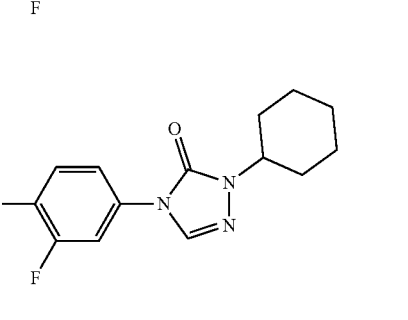 | 113 |

-continued

| Structure | Compound Number |
|---|---|
| 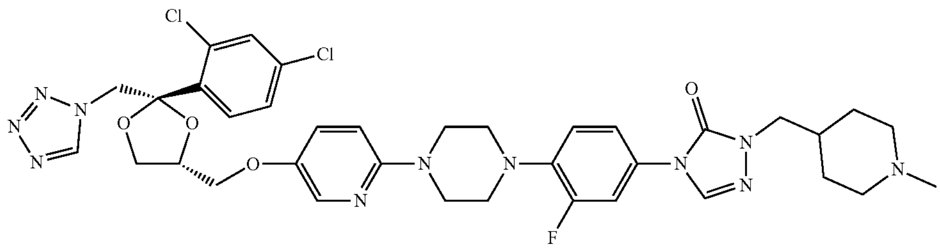 [SMILES: CN1CCC(Cn2ncn(-c3ccc(N4CCN(c5ccc(OC[C@@H]6CO[C@@](Cn7cnnn7)(c7ccc(Cl)cc7Cl)O6)cn5)CC4)c(F)c3)c2=O)CC1] | 114 |
| 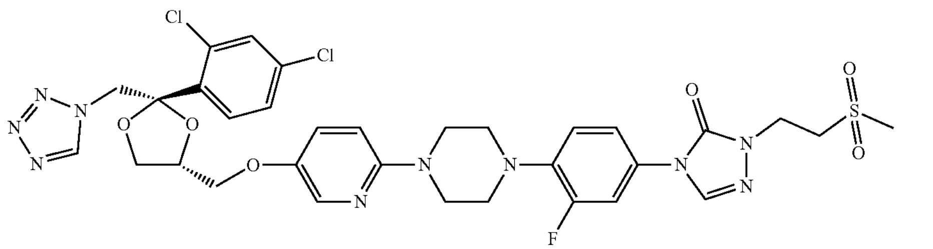 [SMILES: CS(=O)(=O)CCn1ncn(-c2ccc(N3CCN(c4ccc(OC[C@@H]5CO[C@@](Cn6cnnn6)(c6ccc(Cl)cc6Cl)O5)cn4)CC3)c(F)c2)c1=O] | 115 |
| 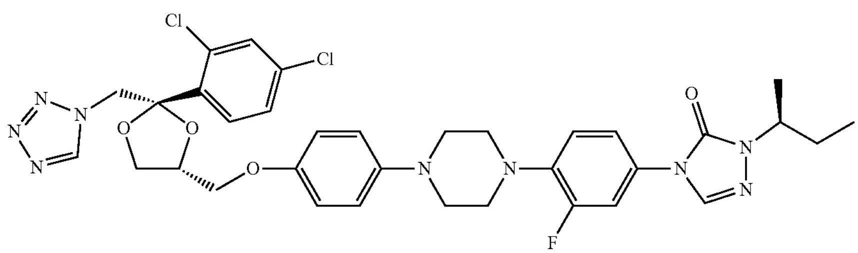 [SMILES: CC[C@H](C)n1ncn(-c2ccc(N3CCN(c4ccc(OC[C@@H]5CO[C@@](Cn6cnnn6)(c6ccc(Cl)cc6Cl)O5)cc4)CC3)c(F)c2)c1=O] | 128 |
| 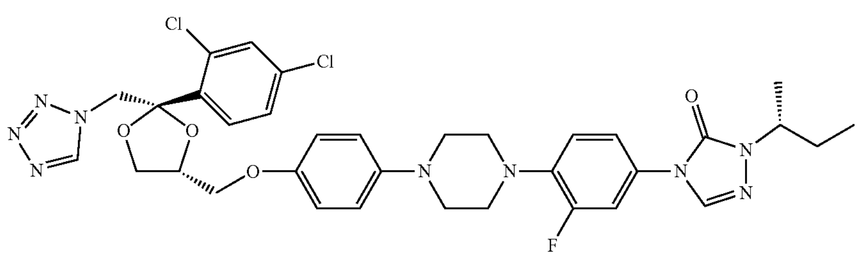 | 129 |
| 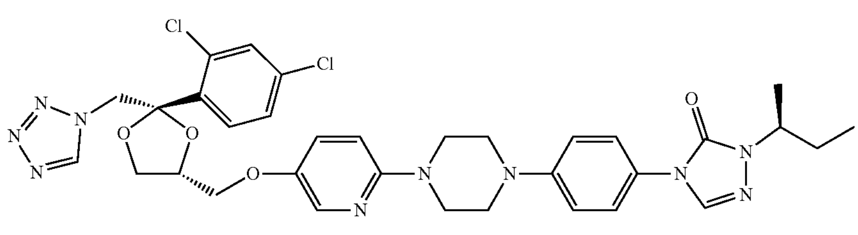 | 130 |
| 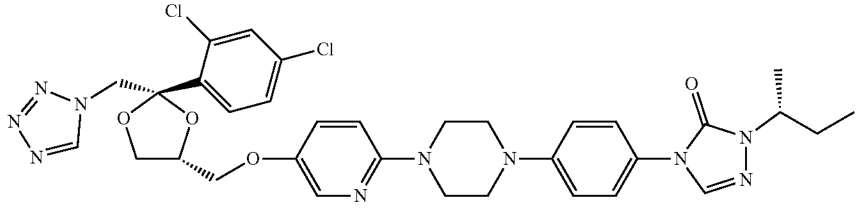 [SMILES: CC[C@@H](C)n1ncn(-c2ccc(N3CCN(c4ccc(OC[C@@H]5CO[C@@](Cn6cnnn6)(c6ccc(Cl)cc6Cl)O5)cn4)CC3)cc2)c1=O] | 131 |

| Structure | Compound Number |
|---|---|
| (structure) | 132 |
| (structure) | 133 |
| (structure) | 134 |
| (structure) | 135 | or a pharmaceutically acceptable salt, hydrate, solvate, or prodrug thereof.

3. A method of treating a disease in a subject, the method comprising administering an effective amount of the compound according to claim 1.

4. The method according to claim 3, wherein the disease is cancer.

5. The method according to claim 4, wherein the cancer is selected from the group consisting of central nervous system (CNS) cancer, lung cancer, breast cancer, colorectal cancer, prostate cancer, stomach cancer, liver cancer, cervical cancer, esophageal cancer, bladder cancer, Non-Hodgkin lymphoma, leukemia, pancreatic cancer, kidney cancer, endometrial cancer, head and neck cancer, lip cancer, oral cancer, thyroid cancer, brain cancer, ovary cancer, renal cancer, melanoma, gallbladder cancer, laryngeal cancer, multiple myeloma, nasopharyngeal cancer, Hodgkin lymphoma, testis cancer and Kaposi sarcoma.

6. The method according to claim 3, wherein the disease is dependent on angiogenesis.

7. The method according to claim 6, wherein the disease is selected from the group consisting of macular degeneration, diabetic retinopathy, hemangiomas, colon polyps, precancerous skin lesions, uveitis, ocular melanoma, corneal neovascularization, primary pterygium, HSV stromal keratitis, HSV-1-induced corneal lymphangiogenesis, retinopathy of prematurity, retinal vein occlusion, corneal graft rejection, neovascular glaucoma, and rubeosis.

8. The method according to claim 3, wherein the compound is formulated in a delayed release preparation, a slow release preparation, an extended release preparation, or a controlled release preparation.

9. The method according to claim 3, wherein the compound is provided in a dosage form selected from an injectable dosage form, infusible dosage form, inhalable dosage form, edible dosage form, oral dosage form, topical dosage form, and combinations thereof.

10. The method according to claim 9, wherein the dosage form comprises an enteric coating.

11. The method according to claim 3, comprising administering a chemotherapeutic agent.

12. The method according to claim 11, wherein the compound is administered prior to, simultaneously with, or following the administration of the chemotherapeutic agent.

13. A pharmaceutical formulation, comprising the compound according to claim 1, and a pharmaceutically acceptable carrier.

* * * * *